United States Patent
Yoda et al.

(10) Patent No.: US 10,974,166 B2
(45) Date of Patent: Apr. 13, 2021

(54) PROTEIN HAVING AFFINITY FOR IMMUNOGLOBULIN, AFFINITY SEPARATION AGENT AND COLUMN FOR LIQUID CHROMATOGRAPHY USING THE SAME

(71) Applicant: Mitsubishi Chemical Corporation, Tokyo (JP)

(72) Inventors: Shoya Yoda, Kanagawa (JP); Satoru Misawa, Kanagawa (JP); Risa Nakata, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 195 days.

(21) Appl. No.: 15/669,498

(22) Filed: Aug. 4, 2017

(65) Prior Publication Data

US 2017/0333811 A1    Nov. 23, 2017

Related U.S. Application Data

(63) Continuation of application No. PCT/JP2016/053116, filed on Feb. 2, 2016.

(30) Foreign Application Priority Data

| Feb. 5, 2015 | (JP) | ............................. JP2015-021577 |
| Feb. 5, 2015 | (JP) | ............................. JP2015-021578 |

(51) Int. Cl.

| *B01D 15/08* | (2006.01) |
| *B01D 15/38* | (2006.01) |
| *C12N 15/00* | (2006.01) |
| *C07K 1/22* | (2006.01) |
| *C07K 17/12* | (2006.01) |
| *C07K 14/31* | (2006.01) |
| *C12N 15/09* | (2006.01) |
| *B01J 20/24* | (2006.01) |
| *B01J 20/289* | (2006.01) |
| *B01J 20/32* | (2006.01) |
| *G01N 30/02* | (2006.01) |
| *C07K 1/00* | (2006.01) |

(52) U.S. Cl.
CPC ......... *B01D 15/08* (2013.01); *B01D 15/3809* (2013.01); *B01J 20/24* (2013.01); *B01J 20/289* (2013.01); *B01J 20/321* (2013.01); *B01J 20/3204* (2013.01); *B01J 20/3212* (2013.01); *B01J 20/3219* (2013.01); *B01J 20/3274* (2013.01); *C07K 1/22* (2013.01); *C07K 14/31* (2013.01); *C07K 17/12* (2013.01); *C12N 15/09* (2013.01); *G01N 30/02* (2013.01); *C07K 1/00* (2013.01); *C12N 15/00* (2013.01)

(58) Field of Classification Search
CPC ..... B01D 15/08; B01D 15/3809; C12N 15/00
See application file for complete search history.

(56) References Cited

U.S. PATENT DOCUMENTS

| 5,143,844 | A  | 9/1992  | Abrahmsen et al. |
| 2005/0143566 | A1 | 6/2005  | Hober |
| 2006/0194950 | A1 | 8/2006  | Hober et al. |
| 2006/0194955 | A1 | 8/2006  | Hober et al. |
| 2009/0299035 | A1 | 12/2009 | Iwakura et al. |
| 2010/0022760 | A1 | 1/2010  | Hober et al. |
| 2010/0048876 | A1 | 2/2010  | Hall et al. |
| 2010/0286373 | A1* | 11/2010 | Majima .................. B01J 20/286 530/387.2 |
| 2011/0112276 | A1 | 5/2011  | Hober |
| 2012/0238724 | A1 | 9/2012  | Hober |
| 2012/0289680 | A1 | 11/2012 | Hall et al. |
| 2013/0046056 | A1 | 2/2013  | Spector et al. |
| 2013/0184438 | A1 | 7/2013  | Hober et al. |
| 2014/0107315 | A1 | 4/2014  | Yoshida et al. |
| 2014/0135476 | A1 | 5/2014  | Hall et al. |
| 2014/0296434 | A1 | 10/2014 | Spector et al. |
| 2015/0080558 | A1 | 3/2015  | Spector et al. |
| 2015/0252085 | A1 | 9/2015  | Spector et al. |

(Continued)

FOREIGN PATENT DOCUMENTS

| JP | 2005-538693 A | 12/2005 |
| JP | 2010-504754 A | 2/2010 |

(Continued)

OTHER PUBLICATIONS

Rosander et al. "An IgG-binding protein a homolog in *Staphylococcus hyicus*" Veterinary Microbiology 149 (2011) 273-276 (Year: 2011).*

(Continued)

*Primary Examiner* — Daniel E Kolker
*Assistant Examiner* — James L Rogers
(74) *Attorney, Agent, or Firm* — Oblon, McClelland, Maier & Neustadt, L.L.P.

(57) ABSTRACT

One embodiment of the present invention is a protein having affinity for an immunoglobulin, which is a protein having two or more domains derived from any of the amino acid sequences of E, D, and A domains of protein A, and in the amino acid sequence of at least one of the domains, one or more lysines are included, and the C-terminal lysine is deleted or substituted, or a protein having affinity for an immunoglobulin, which is a protein having two or more domains derived from any of B, C, and Z domains of protein A, and in the amino acid sequence of at least one of the domains, one or more lysines are included, and lysine at position 4 and the C-terminal lysine are deleted or substituted.

7 Claims, 5 Drawing Sheets

Specification includes a Sequence Listing.

(56) References Cited

U.S. PATENT DOCUMENTS

| | | |
|---|---|---|
| 2016/0152668 A1 | 6/2016 | Hober |
| 2016/0168194 A1 | 6/2016 | Spector et al. |
| 2016/0168209 A1 | 6/2016 | Yoshida et al. |
| 2016/0200797 A1 | 7/2016 | Hall et al. |
| 2016/0215027 A1* | 7/2016 | Majima .................... C07K 1/22 |
| 2017/0080358 A1 | 3/2017 | Hober |

FOREIGN PATENT DOCUMENTS

| | | |
|---|---|---|
| JP | 2012-254981 A | 12/2012 |
| JP | 2013-256484 A | 12/2013 |
| WO | 2008/044692 A1 | 4/2008 |
| WO | 2012/133349 A1 | 10/2012 |
| WO | 2014/046278 A1 | 3/2014 |

OTHER PUBLICATIONS

Ljungberg et al. "The interaction between different domains of Staphylococcal Protein A and human polyclonal IgG, IgA, IgM and F(ab')2: separation of affinity from specificity" Molecular Immunology, vol. 30. No. 14, pp. 1279-1285, 1993 (Year: 1993).*

Japanese Office Action dated Aug. 27, 2019, in Patent Application No. 2016-573393, 5 pages (with unedited computer generated English translation).

Ljungberg, U. K. et al., "The Interaction Between Different Domains of Staphylococcal Protein A and Human Polyclonal IgG, IgA, IgM and F(ab')2: Separation of Affinity From Specificity". Molecular Immunology, vol. 30, No. 14, 1993, pp. 1279-1285.

Extended European Search Report dated Feb. 5, 2018 in Patent Application No. 16746642.4.

Office Action dated Nov. 28, 2018 in European Patent Application No. 16 746 642.4.

Tashiro et al.-"Structures of bacterial immunoglobulin-binding domains and their complexes with immunoglobulins", Current Opinion in Structural Biology, 1995, 5, pp. 471-481.

Hober et al."Protein A chromatography for antibody purification", Journal of Chromatography B, 848(2007), pp. 40-47.

European Summons to attend oral proceedings dated Jan. 24, 2020, in Patent Application No. 16 746 642.4, 5 pages.

* cited by examiner

Fig. 1

PROTEIN HAVING AFFINITY FOR IMMUNOGLOBULIN, AFFINITY SEPARATION AGENT AND COLUMN FOR LIQUID CHROMATOGRAPHY USING THE SAME

TECHNICAL FIELD

The present invention relates to a protein which specifically binds to an immunoglobulin, an affinity separation agent using the protein as an immunoglobulin-binding affinity ligand, and further a column for liquid chromatography.

BACKGROUND ART

An antibody has a function to specifically bind to a substance called "antigen", and also has a function to detoxify and remove a factor having antigenicity in cooperation with another biomolecule or a cell. The name of "antibody" is a name that centers on the function to bind to such an antigen, and is called "immunoglobulin" as a substance.

Recently, as the progress of genetic engineering, protein engineering, and cell engineering, a pharmaceutical product utilizing the function of an antibody called "antibody preparation" has been actively developed. The antibody preparation acts on a target molecule more specifically than conventional preparations, and therefore is expected to further reduce adverse effects, and also to obtain a high therapeutic effect, and actually contributes to the improvement of various pathological conditions.

On the other hand, the antibody preparation is administered to a living body at a high dose, and therefore, it is said that the effect of the purity thereof on the quality is large as compared with other recombinant protein pharmaceutical products. Due to this, in order to produce an antibody with high purity, a method such as affinity chromatography utilizing an adsorption material using a molecule which specifically binds to an antibody as a ligand is generally employed.

What has been developed as an antibody preparation is basically a monoclonal IgG antibody, which is produced in a large amount using a recombinant cultured cell technique or the like, and purified by utilizing a protein having affinity for an IgG antibody.

As an immunoglobulin-binding protein having affinity for an IgG antibody, protein A is well known. Protein A is a kind of cell wall protein produced by a Gram-positive bacterium, *Staphylococcus aureus*, and is constituted by a signal sequence S, five immunoglobulin-binding domains (E domain, D domain, A domain, B domain, and C domain), and an XM region which is a cell wall-binding domain (NPL 1). In an initial purification step (capture step) in an antibody preparation production step, a column for affinity chromatography formed by immobilizing Protein A as a ligand on a water-insoluble support is generally used.

In order to improve the performance of this column for affinity chromatography, recently, various developments on Protein A to serve as a ligand have been conducted, and an attempt to use recombinant Protein A modified by protein engineering has been made.

For example, as the recombinant Protein A, Protein A in which the XM region with no immunoglobulin-binding activity has been removed (rProtein A Sepharose (registered trademark), manufactured by GE health care, Japan), Protein A having Z domain which is a modified domain obtained by introducing a mutation into B domain disclosed in PTL 1, and the like are known.

The Z domain is a modified domain obtained by introducing a mutation into the B domain such that glycine at position 29 is substituted with alanine, and is known to have higher alkali resistance than the B domain. In this manner, in order to improve the ligand function, recombinant Protein A having enhanced alkali resistance, and recombinant Protein A capable of eluting an antibody at a weak acidic pH have been developed.

In PTL 2, in order to enhance alkali resistance, an affinity chromatography ligand including a deletion of 3 to 5 successive amino acids at the N t nus of C, B, and Z domains of Protein A is disclosed.

In PTL 3, in order to enhance alkali stability, an affinity chromatography ligand having a sequence in which Asn-Lys-Phe-Asn at positions 3-6 of a domain C unit of Protein A is deleted is disclosed.

In PTL 4, in order to enhance alkali resistance, an immunoglobulin-binding protein in which asparagine at positions 3 and 6 of B and Z domains of Protein A is substituted with another amino acid is disclosed.

In PTL 5, in order to enable antibody desorption at a weak acidic pH, an antibody recognition and binding protein having a sequence in which lysine and cysteine residues are not included in E, D, A, B, and C domains of Protein A is disclosed.

CITATION LIST

Patent Literature

PTL 1: U.S. Pat. No. 5,143,844
PTL 2: JP-A-2012-254981
PTL 3: JP-T-2010-504754
PTL 4: JP-T-2005-538693
PTL 5: JP-A-2013-256484

Non Patent Literature

NPL 1: Hober S. et. al, J. Chromatogr. B., 2007, Vol. 848, p. 40-47

SUMMARY OF INVENTION

Technical Problem

As a result of studies conducted by the present inventors, they found for the first time that there is a problem that Protein A to serve as a ligand is cleaved by the action of a protease produced by a host microorganism used when producing recombinant Protein A or a protease produced by a recombinant cultured cell when purifying an IgG antibody produced by the cultured cell, and therefore, the immunoglobulin-binding activity is largely decreased.

It was revealed that particularly in a step of purifying recombinant Protein A from a culture solution, the cleavage by a protease is significantly problematic when the recombinant Protein A is adsorbed on an ion exchange resin or the culture solution is allowed to pass through an ion exchange resin while increasing the pH, and when a condensation or desalting step or the like is performed before purification or after purification, and further when a step of purifying an immunoglobulin from the culture solution containing the immunoglobulin using a separating agent having the recombinant Protein A immobilized thereon is performed.

One of the above-mentioned proteases is a serine protease. The recombinant Protein A disclosed in PTL 1 to PTL 4 does not have resistance to a serine protease, and therefore has a problem in that it is used as a ligand in a column for affinity chromatography.

Further, according to the studies conducted by the present inventors, it was newly found that the recombinant Protein A which does not include lysine and cysteine disclosed in PTL 5 has a problem such that the immunoglobulin-binding activity is not sufficient, and in particular, when it is multimerized, the immunoglobulin-binding activity is lower than that of a wild type, and it cannot sufficiently perform its function as a ligand in a column for affinity chromatography in the first place.

Further, as another protease which causes the above problem, thermolysin is known. Thermolysin is a metalloproteinase derived from a bacterium of the genus *Bacillus*, and its activity increases in an environment at a relatively high temperature or in an environment at a high pH. The recombinant Protein A disclosed in PTL 1, and PTL 3 to PTL 5 does not have resistance to thermolysin, and therefore, the protein in an intact form cannot be collected, and has a problem in that it is used as a ligand in a column for affinity chromatography.

Further, according to the studies conducted by the present inventors, it was newly found that although the recombinant Protein A disclosed in PTL 2 includes those having resistance to thermolysin, it has a problem such that the immunoglobulin-binding activity decreases, and therefore, it cannot sufficiently perform its function as a ligand in a column for affinity chromatography in the first place.

In view of this, an object of the present invention is to provide a protein which has resistance to a protease, and has a sufficient immunoglobulin-binding activity, and therefore can be favorably used as an affinity ligand.

In particular, a first object of the present invention is to provide a protein which has resistance to particularly a serine protease among proteases, has a sufficient immunoglobulin-binding activity, and can be favorably used as an affinity ligand.

Further, a second object of the present invention is to provide a protein which has resistance to particularly thermolysin among proteases, has a sufficient immunoglobulin-binding activity, and can be favorably used as an affinity ligand.

Solution to Problem

The present inventors conducted intensive studies for achieving the above first object, and as a result, they found that when lysine is not included in a region where a domain and a domain are ligated in the amino acid sequence of a specific domain of Protein A, the resistance to a serine protease is improved, and thus completed the present invention.

Further, the present inventors conducted intensive studies for achieving the above second object, and as a result, they found that when a hydrophobic amino acid is not included in a region where a domain and a domain are ligated in the amino acid sequence of a specific domain of Protein A, the resistance to thermolysin is improved, and thus completed the present invention.

That is, the above objects are achieved by the following configurations.

[1] A protein having affinity for an immunoglobulin, which is a protein having two or more domains derived from any of E, D, and A domains of Protein A represented by SEQ ID NOS: 1 to 3, wherein in the amino acid sequence of at least one domain of the domains, one or more lysines are included, and the C-terminal lysine is deleted or substituted.

[2]-(1) A protein having affinity for an immunoglobulin, which is a protein having two or more domains derived from any of B, C, and Z domains of Protein A represented by SEQ ID NOS: 4 to 6, wherein in the amino acid sequence of at least one domain of the domains, one or more lysines are included, and lysine at position 4 and the C-terminal lysine are deleted or substituted.

[2]-(2) A protein having affinity for an immunoglobulin, which is a protein having two or more domains derived from any of B, C, and Z domains of Protein A represented by SEQ ID NOS: 4 to 6, wherein in the amino acid sequence of at least one of the domains, one or more lysines are included, and when the C-terminal lysine of each domain and a sequence at positions 1-5 in the amino acid sequence of each domain are defined as a ligation site sequence (first ligation element), the C-terminal lysine and lysine at position 4 in at least one of the ligation site sequences (first ligation elements) are deleted or substituted.

[3] The protein according to [1] or [2], wherein, of the lysine at position 4 and the C-terminal lysine Which are deleted or substituted, the lysine at position 4 and/or the C-terminal lysine are/is deleted.

[4] The protein according to any one of [1] to [3], wherein when the C-terminal lysine of each domain and a sequence at positions 1-5 in the amino acid sequence of each domain are defined as a ligation site sequence (first ligation element), at least one of the ligation site sequences (first ligation elements) is composed of one or more amino acids.

[5] The protein according to any one of [1] to [4], wherein, of the lysine at position 4 and the C-terminal lysine which are deleted or substituted, the lysine at position 4 and/or the C-terminal lysine are/is substituted with a hydrophilic amino acid.

[6] The protein according to any one of [1] to [5], which has three or more domains.

[7] The protein according to any one of [1] to [6], wherein when the C-terminal lysine of each domain and a sequence at positions 1-5 in the amino acid sequence of each domain are defined as a ligation site sequence (first ligation element), in all the ligation site sequences (first ligation elements), lysine is deleted or substituted.

[8] The protein according to any one of [1] to [7], wherein all the domains included in the protein are derived from any one of the amino acid sequences of E, D, A, B, C, and Z domains of Protein A represented by SEQ ID NOS: 1 to 6.

[9] The protein according to any one of [1] to [8], wherein when the C-terminal lysine of each domain and a sequence at positions 1-5 in the amino acid sequence of each domain are defined as a ligation site sequence (first ligation element), the ligation site sequence (first ligation element) does not include lysine.

[10] The protein according to any one of [1] to [9], wherein when the C-terminal lysine of each domain and a sequence at positions 1-5 in the amino acid sequence of each domain are defined as a ligation site sequence (first ligation element), the ligation site sequence (first ligation element) does not include arginine.

[11] An affinity separation agent, where the protein according to any one of [1] to [10] as an affinity ligand is immobilized on a support composed of a water-insoluble base material.

[12] A column for liquid chromatograph, comprising: the affinity separation agent according to [11]; and at least one container.

[13] A protein having affinity for an immunoglobulin, which is a protein having two or more domains derived from any of A, B, C, and Z domains of Protein A represented by SEQ ID NOS: 3 to 6, wherein when a sequence at positions 1-5 in the amino acid sequence of each domain is defined as a ligation element (second ligation element), at least one ligation element (second ligation element) is a mutated ligation element (mutated second ligation element) which is composed of one or more amino acids, and is constituted by an amino acid other than a hydrophobic amino acid.

[14] The protein according to [13], wherein the mutated ligation element (mutated second ligation element) is composed of a sequence at positions 1-5 in the amino acid sequence of the A, B, or C domain, and alanine at position 1 and/or phenylalanine at position 5 in the amino acid sequence of at least one mutated ligation element are/is deleted.

[15] The protein according to [13], wherein the mutated ligation element (mutated second ligation element) is composed of a sequence at positions 1-5 in the amino acid sequence of the Z domain, and valine at position 1 and/or phenylalanine at position 5 in the amino acid sequence of at least one mutated ligation element are/is deleted.

[16] The protein according to [13] or [14], wherein the mutated ligation element (mutated second ligation element) is composed of a sequence at positions 1-5 in the amino acid sequence of the A, B, or C domain, and alanine at position 1 and/or phenylalanine at position 5 in the amino acid sequence of at least one mutated ligation element are/is substituted with an amino acid other than a hydrophobic amino acid.

[16] The protein according to [13] or [15], wherein the mutated ligation element (mutated second ligation element) is composed of a sequence at positions 1-5 in the amino acid sequence of the Z domain, and valine at position 1 and/or phenylalanine at position 5 in the amino acid sequence of at least one mutated ligation element are/is substituted with an amino acid other than a hydrophobic amino acid.

[18] The protein according to [16] or [17], wherein the amino acid other than a hydrophobic amino acid substituted in the mutated ligation element (mutated second ligation element) is a hydrophilic amino acid.

[19] The protein according to any one of [13] to [18], wherein the mutated ligation element (mutated second ligation element) is composed of two or more amino acids.

[20] The protein according to any one of [13] to [19], which has three or more domains.

[21] The protein according to any one of [13] to [20], wherein all the ligation elements (second ligation elements) are mutated ligation elements (mutated second ligation elements).

[22] The protein according to any one of [13] to [21], wherein all the domains included in the protein are derived from any one type of the amino acid sequences of A, B, C, and Z domains of Protein A represented by SEQ ID NOS: 3 to 6.

[23] The protein according to any one of [13] to [22], wherein the C-terminal lysine in the amino acid sequence of at least one domain is deleted or substituted.

[24] The protein according to [23], wherein, in the domain in which the mutated ligation element (mutated second ligation element) is bound on the C-terminal side, the C-terminal lysine in the amino acid sequence of the domain is deleted or substituted.

[25] The protein according to any one of [13] to [24], wherein the mutated ligation element (mutated second ligation element) does not include lysine.

[26] The protein according to any one of [13] to [25], wherein the mutated ligation element (mutated second ligation element) does not include arginine.

[27] A method for producing the protein according to any one of [13] to [26], wherein the protein is produced by transforming a bacterium of the genus *Brevibacillus* using a vector including a DNA encoding the protein according to any one of [13] to [26], and culturing the transformant.

[28] An affinity separation agent, where the protein according to any one of [13] to [26] as an affinity ligand is immobilized on a support composed of a water-insoluble base material.

[29] A column for liquid chromatograph, comprising the affinity separation agent according to [28]; and at least one container which packs the affinity separation agent According to the embodiments of the present invention, a protein which has resistance to a specific protease, and has a sufficient immunoglobulin-binding activity can be provided. By using such a protein of the present invention, an affinity ligand which has an excellent immunoglobulin-binding activity or an affinity separation agent which has excellent durability can be produced.

In particular, according to the first embodiment of the present invention, a protein which has resistance to a protease, particularly a serine protease, and has a sufficient immunoglobulin-binding activity can be provided. By using such a protein of the present invention, an affinity ligand which has an excellent immunoglobulin-binding activity or an affinity separation agent which has excellent durability can be produced.

Further, according to the second embodiment of the present invention, a protein which has resistance to a protease, particularly thermolysin, and has an ability to bind to an immunoglobulin can be provided. By using such a protein of the present invention, an affinity ligand which has an excellent ability to bind to an immunoglobulin or an affinity separation agent which has excellent durability can be produced.

BRIEF DESCRIPTION OF DRAWINGS

Figure 1:
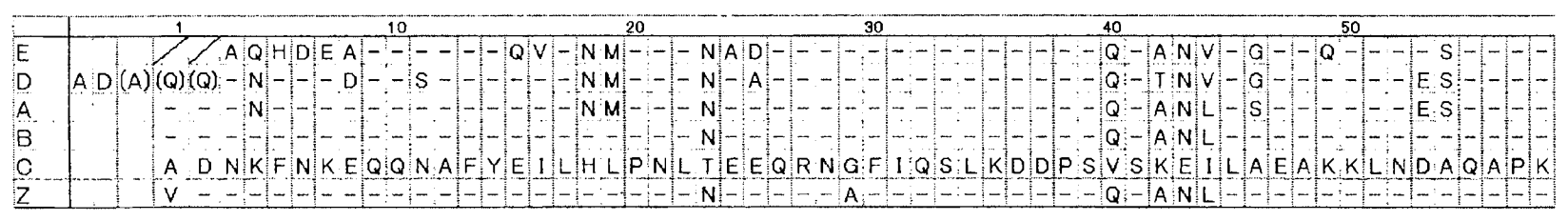

FIG. 1 is a table for comparison of the amino acid sequences of E, D, A, B, C and Z domains of Protein A of *Staphylococcus*. Incidentally, the symbol "- (hyphen)" indicates that it is the same amino acid residue as that of C domain, and the symbol "/ (slash)" indicates that the amino acid is deleted.

DESCRIPTION OF EMBODIMENTS

Figure 2:
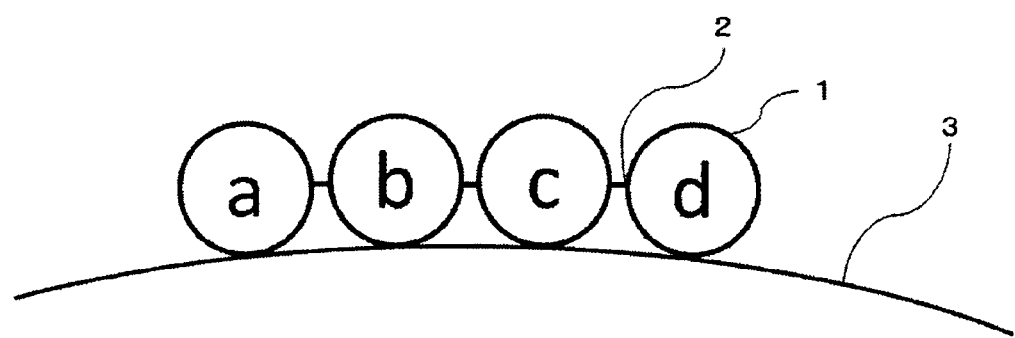
FIG. 2 is a schematic view in the case where a tetramer protein is immobilized on a support as a ligand, and a non-immobilized domain is not formed.

Hereinafter, embodiments of the present invention will be described in detail.

Incidentally, the embodiments of the present invention relate to a protein which has resistance to a specific protease, and has a sufficient immunoglobulin-binding activity.

A first embodiment of the present invention relates to a protein which has resistance to a protease, particularly a serine protease, and has a sufficient immunoglobulin-binding activity.

Further, a second embodiment of the present invention relates to a protein which has resistance to a protease, particularly thermolysin, and has an ability to bind to an immunoglobulin.

Incidentally, in this description, the term "protein" includes any molecules having a polypeptide structure, and fragmented polypeptide chains and polypeptide chains linked through a peptide bond are also included in the term "protein".

Further, the "domain" is a higher-order structural unit of a protein, and refers to a unit of a protein which is constituted by a sequence of several tens to several hundreds of amino acid residues and is sufficient for expressing a certain physicochemical or biochemical function.

First Embodiment of the Invention

<Protein>

The protein of the first aspect in the first embodiment of the present invention is characterized in that the protein has two or more domains derived from any of E, D, and A domains of Protein A represented by SEQ ID NOS: 1 to 3, and in the amino acid sequence of at least one domain of the domains, one or more lysines are included, and the C-terminal lysine is deleted or substituted.

The protein of the second aspect in the first embodiment of the present invention is characterized in that the protein has two domains derived from any of B, C, and Z domains of Protein A represented by SEQ ID NOS: 4 to 6, and in the amino acid sequence of at least one domain of the domains, one or more lysines are included, and lysine at position 4 and the C-terminal lysine are deleted or substituted.

The protein of the third aspect in the first embodiment of the present invention is characterized in that the protein has two or more domains derived from any of B, C, and Z domains of Protein A represented by SEQ ID NOS: 4 to 6, and in the amino acid sequence of at least one domain of the domains, one or more lysines are included, and when the C-terminal lysine of each domain and a sequence at positions 1-5 in the amino acid sequence of each domain are defined as a ligation site sequence (first ligation element), the C-terminal lysine and lysine at position 4 in at least one of the ligation site sequences (first ligation elements) are deleted or substituted.

Hereinafter, in this description, the proteins of the first aspect, the second aspect, and the third aspect in the first embodiment of the present invention are collectively referred to as "protein of the first embodiment of the present invention".

Protein A is a protein constituted by five immunoglobulin-binding domains in a connected form. A plurality of microorganisms express Protein A. and examples of the microorganism which expresses Protein A include *Staphylococcus*.

The E, D, A, B, C, and Z domains of Protein A represented by SIM ID NOS: 1 to 6 are immunoglobulin-binding proteins capable of binding to a region other than the complementarity-determining regions (CDRs) of an immunoglobulin, and all the domains bind to each region of the Fc region and the Fab region of an immunoglobulin, and particularly the region in the Fab region.

As shown in the sequence comparison table of FIG. 1, the E, D, A, B, C, and Z domains derived from Protein A have amino acid sequences with a high homology with one another, and have an amino acid sequence identity of 60% or more. Incidentally, the hyphen (-) indicates that it is the same amino acid residue as that of the C domain.

The "domain derived from any of the E, D, A, C, and Z domains of Protein A" refers to a domain having an amino acid sequence derived from the amino acid sequence of each of the wild-type domains, and a mutation other than the below-mentioned mutated ligation site sequence (mutated first ligation element) may be included in the amino acid sequence of each of the wild-type domains as long as it encodes a protein having an ability to bind to the Fc region.

That is, the amino acid sequence of any of the E, D, A, B, C, and Z domains of Protein A is the amino acid sequence before a mutation is introduced (wild-type amino acid sequence), and the amino acid sequence of the "domain derived from any of the E, D, A, B, C, and Z domains of Protein A" refers to the wild-type amino acid sequence of the E, D, A, B, C, or Z domain itself, or an amino acid sequence which includes the below-mentioned mutated ligation site sequence (mutated first ligation element) in the wild-type amino acid sequence, and/or is partially modified by substitution, insertion, deletion, or chemical modification of an amino acid.

Here, the Z domain of Protein A is a domain obtained by introducing mutations A1V and G29A into the B domain, and is not present in natural Protein A, however, in this description, the amino acid sequence represented by SEQ ID NO: 6 is referred to as "the wild-type amino acid sequence of the Z domain".

In this description, the position of a specific amino acid in an amino acid sequence is specified by sequentially numbering amino acids by defining the N-terminal position in the wild-type amino acid sequence as position 1. In general, the N-terminal position in the amino acid sequence of each domain is defined as position 1. The amino acid at position 4 which is the fourth amino acid from the N terminus of each of the B, C, and Z domains of Protein A is lysine. Here, as shown in FIG. 1, the E domain is treated by assuming that the amino acid residues at positions 1 and 2 are deleted based on the region with a high homology with the other domains. Further, as shown in FIG. 1, the D domain is treated by assuming that the third to fifth amino acid residues from the N terminus are inserted based on the region with a high homology with the other domains.

In this description, with respect to an amino acid, when an amino acid is not expressed by its formal name, the amino acid is expressed by a commonly used one letter abbreviation. Further, with respect to the expression of a mutation in which an amino acid is substituted, the mutation is expressed as follows: the amino acid of the wild-type or non-mutated type is attached before the number of the position of the substation, and the amino acid after the mutation is attached after the number of the position of the substation. For example, a mutation in which glycine (Gly) at position 29 is substituted with alanine (Ala) is expressed by "G29A".

The protein of the first embodiment of the present invention is a multimer protein (multi-domain protein) having two or more domains, each of which is the "domain derived from any of E, D, A, B, C, and Z domains of Protein A" described above as a single domain. The protein has preferably 3 or more domains, more preferably 4 or more domains, and preferably 10 or less domains, more preferably 8 or less domains, further more preferably 6 or less domains.

Such a multimer protein may be a homopolymer such as a homodimer or a homotrimer, which is a connected body of a single immunoglobulin-binding domain, or may be a heteropolymer such as a heterodimer or a heterotrimer, which is a connected body of different types of immunoglobulin-binding domains. It is preferred that all the domains included in the protein of the first embodiment of the present invention are homopolymers derived from any one type of the E, D, A, C, and Z domains of Protein A represented by SEQ ID NOS: 1 to 6.

In the protein of the first embodiment of the present invention, the C terminus and the N terminus of two or more domains are ligated to form a ligation site sequence (first ligation element). Here, in this description, the "ligation site sequence (first ligation element)" refers to the C-terminal lysine in the amino acid sequence of each domain and a sequence at positions 1-5 at the N terminus ligated thereto.

That is, a sequence of 6 amino acid residues in total including one amino acid residue on the C-terminal side and 5 amino acid residues on the N-terminal side at a site where two domains are ligated becomes the ligation site sequence (first ligation element). Here, the amino acid sequence on the N-terminal side is based on the amino acid sequence conserved in the B, C, and Z domains and refers to the 5 amino acid residues of the sequence.

Therefore, as shown in FIG. 1, the E domain has a sequence in which two amino acid residues from the N terminus are deleted in the sequence on the N-terminal side to serve as the basis, and therefore, in the case where the E domain is included, the ligation site sequence (first ligation element) is assumed to refer to a sequence of 4 amino acid residues in total including one amino acid residue on the C-terminal side and 3 amino acid residues on the N-terminal side.

Further, as shown in FIG. 1, the D domain has a sequence in which three amino acid residues shown in the parentheses are inserted into the sequence on the N-terminal side to serve as the basis, and therefore, in the case where the present protein includes the D domain, 9 amino acid residues in total including one amino acid residue on the C-terminal side and 8 amino acid residues on the N-terminal side are included in a ligation portion between domains. However, it is considered that the 3 amino acid residues "AQQ" inserted on the N-terminal side of the D domain do not particularly affect the effect of the present invention, and therefore, in this description, the amino acid sequence conserved in the B, C, and Z domains is used as the basis, and the amino acid sequence at positions 1-5 from the N terminus of the D domain included in the ligation site sequence (first ligation element) is assumed to refer to 5 amino acid residues shown below.

In an n-mer protein, n−1 ligation site sequences (first ligation elements) are present.

As shown in FIG. 1, in any of the E, D, A, B, C, and Z domains of Protein A, the C-terminal amino acid is always lysine (K). Therefore, the above-mentioned ligation site sequence (first ligation element) always includes lysine (K).

Further, the sequences shown below are sequences at positions 1-5 in the amino acid sequences of the E, D, A, B, C, and Z domains of Protein A. In the E domain, amino acid residues at positions 1 and 2 are not present, and 3 amino acids are included, and lysine (K) is not included. Any of the sequences of the D, A, B, C, and Z domains is composed of 5 amino acids, the D and A domains do not include lysine (K), and the B, C, and Z domains include lysine (K) at position 4.

| | |
|---|---|
| E domain | A Q H |
| D domain | A D N N F |
| A domain | A D N N F |
| B domain | A D N K F |
| C domain | A D N K F |
| Z domain | V D N K F |

The proteins of the first and third aspects in the first embodiment of the present invention are characterized in that at least one ligation site sequence (first ligation element) is a mutated ligation site sequence (mutated first ligation element) partially modified by substitution, insertion, deletion, or chemical modification of an amino acid, and is an amino acid sequence including no lysine which is present in the wild-type amino acid sequence. The mutated ligation site sequence (mutated first ligation element) preferably does not include lysine (K), more preferably is a sequence constituted by an amino acid other than lysine (K) and arginine (R), and preferably composed of one or more amino acids.

On the other hand, the protein of the second aspect in the first embodiment of the present invention is characterized in that in the amino acid sequence of at least one of the B, C, and Z domains, lysine at position 4 and the C-terminal lysine are deleted or substituted. Therefore, by ligating a plurality of the domains, the mutated ligation site sequence (mutated first ligation element) of the third aspect is formed. In addition, a domain located closest to the N terminus or the C terminus of the protein is the domain, the terminal portion does not form the mutated ligation site sequence, however, in the below-mentioned affinity separation agent obtained by immobilizing an affinity ligand on a support, by immobilizing the domain of the protein on the N-terminal side or the C-terminal side on the support, the binding of the protein to the support and the binding of the immobilized domain to another domain can be stably maintained.

Here, the "mutation" in the first embodiment of the present invention means partial modification by substitution, insertion, deletion, or chemical modification of an amino acid performed for a wild-type amino acid sequence, and the "mutated ligation site sequence (mutated first ligation element)" refers to a sequence formed by inserting a specific "mutation" into the ligation site sequence (first ligation element) of a wild-type amino acid sequence. Further, a "mutated domain" refers to a domain formed by inserting a specific "mutation" into the wild-type amino acid sequence of each domain.

At least one of the ligation site sequences (first ligation elements) included in the proteins of the first and third aspects in the first embodiment of the present invention may be a mutated ligation site sequence (mutated first ligation element). However, in the case of a trimer or higher-order multimer protein, it is preferred that two or more of them are mutated ligation site sequences (mutated first ligation elements), and in the case of an n-mer protein, it is more preferred that (n−1) of them are mutated ligation site sequences (mutated first ligation elements), that is, all the ligation site sequences (first ligation elements) are mutated ligation site sequences (mutated first ligation elements).

Therefore, it is preferred that in the protein of the first embodiment of the present invention, in all the ligation site sequences (first ligation elements), lysine is deleted or substituted.

In the below-mentioned affinity separation agent, in order for the ligand immobilized on the support not to be cleaved by a protease, it is preferred that in the protein of the first embodiment of the present invention, lysine at position 4 of the domain closest to the N terminus or the C-terminal lysine of the domain closest to the C terminus is deleted or substituted.

Therefore, at least one of the domains included in the protein of the second aspect in the first embodiment of the present invention may be a domain (mutated domain) in which lysine at position 4 or the C-terminal lysine is deleted or substituted, however, it is preferred that the domain closest to the N terminus or the domain closest to the C terminus of the protein is a mutated domain, and the below-mentioned immobilized domain is a mutated domain. In addition, in the case of a trimer or higher-order multimer protein, it is preferred that the immobilized domain and two or more of domains ligated thereto are mutated domains, and in the case of an n-mer protein, it is preferred that the immobilized domain and (n−2) or more domains ligated thereto are mutated domains, and it is most preferred that all the domains are mutated domains.

The ligation site sequence (first ligation element) is composed of one amino acid residue at the C terminus and a sequence at positions 1-5 in the amino acid sequence of each domain, but is preferably composed of one or more amino acids by performing modification for this sequence through substitution, insertion, deletion, or chemical modification, and is preferably a sequence constituted by an amino acid other than lysine (K) and arginine (R).

According to the studies conducted by the present inventors, it was revealed that a site which is likely to be cleaved by a serine protease such as trypsin or plasmin is on the C-terminal side of lysine (K) at a specific position present in the wild-type amino acid sequence in the ligation site sequence (first ligation element). Based on this, it was found that by forming a mutated ligation site sequence (mutated first ligation element) constituted by amino acids so that specific lysine (K) which is present in the ligation site sequence (first ligation element) is not included, the cleavage of the protein by a serine protease can be significantly suppressed.

Specifically, a mutated ligation site sequence (mutated first ligation element) can be formed by deleting and/or substituting K in the ligation site sequence (first ligation element) of the wild-type amino acid sequence. It is preferred to form a mutated ligation site sequence (mutated first ligation element) constituted by amino acids other than K, and it is more preferred to form a mutated ligation site element constituted by amino acids other than K and R.

In addition, according to the studies conducted by the present inventors, it was found that K and R present other than in the ligation site sequence (first ligation element) of the wild-type amino acid sequence are less likely to be cleaved by a serine protease, and therefore may be present in each domain of the protein of the first embodiment of the present invention, and also in order for the protein of the first embodiment of the present invention to have a sufficient immunoglobulin-binding activity, the protein is required to include one or more lysines in at least one domain.

As for the lysine present other than in the ligation site sequence (first ligation element), lysine in the wild-type amino acid sequence is preferably conserved, preferably, two or more lysines are conserved, more preferably, three or more lysines are conserved, and most preferably, four or more lysines are conserved at the same positions as in the wild-type amino acid sequence. As the K to be conserved, it is most preferred that lysine at position 35 is conserved.

The reason why lysine present other than in the ligation site sequence (first ligation element) is required for the protein to have a sufficient immunoglobulin-binding activity has not yet been made clear, however, it is considered that lysine near the antibody recognition site of the wild-type Protein A electrostatically interacts with an antibody. Due to this, lysine which is not present in the wild-type amino acid sequence may be included by a mutation such as substitution or insertion within the range in which the function of the antibody recognition site of the wild-type Protein A is not impaired, however, it is preferred that lysine which is not present in the wild-type amino acid sequence is not included.

Hereinafter, specific examples of the mutated ligation site sequence (mutated first ligation element) will be described.

In the case where a mutated ligation site sequence (mutated first ligation element) is formed by deleting some of the amino acids of the ligation site sequence (first ligation element), it is essential that the mutated ligation site sequence (mutated first ligation element) be composed of one or more amino acids. According to the studies conducted by the present inventors, it was revealed that in the case where all the 6 amino acids included in the ligation site sequence (first ligation element) are deleted, the ability to bind to a target immunoglobulin is significantly decreased, and when the protein is used as an affinity ligand, the ability to bind to the immunoglobulin is insufficient.

In general, an immunoglobulin is larger than each domain, and the number of immunoglobulins capable of binding to each domain is limited due to the steric hindrance of the bound immunoglobulin molecules. Due to this, it is presumed that when each domain and an immunoglobulin are bound to each other, if the ligation site sequence (first ligation element) is not present and adjacent domains are located too close to each other, a space enabling an immunoglobulin to bind thereto is lacking, and thus, the number of immunoglobulins to be bound per domain is decreased. When the mutated ligation site sequence (first ligation element) is composed of preferably one or more amino acids, more preferably two or more amino acids, an ability to bind to a target immunoglobulin is likely to be further enhanced, and therefore such a case is preferred.

In the protein of the first aspect in the first embodiment of the present invention, the ligation site sequence (first ligation element) is composed of the C-terminal lysine (K) of any of the domains of Protein A and a sequence at positions 1-5 in the amino acid sequence of each of the E, D, and A domains. Due to this, in the ligation site sequence (first ligation element) of the wild-type amino acid sequence, one K is included. Therefore, the mutated ligation site sequence (mutated first ligation element) is preferably a sequence formed by deleting the C-terminal lysine (K) of the domain to be ligated.

For example, in the case where a ligation site sequence (first ligation element) formed by ligating two A domains of Protein A is changed into a mutated ligation site sequence (mutated first ligation element), a sequence which is formed by deleting the C-terminal lysine (K) and therefore is composed of five amino acids: alanine (A), aspartic acid (D), asparagine (N), asparagine (N), and phenylalanine (F), a sequence which is formed by deleting A at position 1 and F at position 5 in addition to the C-terminal K and therefore is composed of three amino acids: D, N, and N, and the like can be exemplified as preferred examples.

In the proteins of the second and third aspects in the first embodiment of the present invention, the ligation site sequence (first ligation element) is composed of the C-terminal lysine (K) of any of the domains of Protein A and a sequence at positions 1-5 in the amino acid sequence of each of the B, C, and Z domains. Due to this, in the ligation site sequence (first ligation element) of the wild-type amino acid sequence, two Ks are included at the C terminus and at position 4. Therefore, the mutated ligation site sequence (first ligation element) is preferably a sequence formed by deleting the C-terminal lysine (K) and the lysine (K) at position 4 of the domain to be ligated.

For example, in the case where a ligation site sequence (first ligation element) formed by ligating B domains of Protein A is changed into a mutated ligation site sequence (mutated first ligation element), a sequence which is formed by deleting two amino acids: the C-terminal lysine (K) and lysine (K) at position 4 and therefore is composed of four amino acids: alanine (A), aspartic acid (D), asparagine (N), and phenylalanine (F), a sequence which is formed by deleting V at position 1 and F at position 5 in addition to the C-terminal K and K at position 4 and therefore is composed of two amino acids: D and N, and the like can be exemplified as preferred examples. Further, in the case where either one of Ks included in the ligation site sequence (first ligation element) is substituted by the below-mentioned method, only the C-terminal K may be deleted or only K at position 4 may be deleted.

The substitution of an amino acid means a mutation in which the original amino acid is deleted and a different amino acid is added at the same position. The different amino acid to be added is not particularly limited, and for example, a natural constituent amino acid of a protein, a natural non-constituent amino acid of a protein, and an unnatural amino acid can be exemplified. Among these, from the viewpoint of production by genetic engineering, a natural amino acid can be preferably used.

However, in the case where a mutated ligation site sequence (mutated first ligation element) is formed by substituting an amino acid in the ligation site sequence (first ligation element), it is necessary to form a sequence such that lysine (K) is not included in the mutated ligation site sequence (mutated first ligation element). Further, when the sequence is a sequence which does not include arginine (R) either, the resistance to a protease which recognizes arginine is also improved, and therefore, such a case is preferred.

Therefore, the amino acid to be introduced by the substitution is not particularly limited as long as it is an amino acid other than lysine (K) and arginine (R), but is preferably any of hydrophilic amino acids such as asparagine (N), aspartic acid (D), glutamine (Q), glutamic acid (E), and histidine (H); and neutral amino acids such as cysteine (C), glycine (G), methionine (M), serine (S), threonine (T), and tyrosine (Y). Among these, the amino acid is more preferably any of the above-mentioned hydrophilic amino acids.

Further, from the viewpoint that the stability under an alkaline condition is improved, aspartic acid (D), glutamine (Q), glutamic acid (E), and histidine (H) are preferred.

In the protein of the first aspect in the first embodiment of the present invention, in the ligation site sequence (first ligation element) of the wild-type amino acid sequence, one K is included, and the mutated ligation site sequence (mutated first ligation element) is preferably a sequence formed by substituting the C-terminal lysine (K) of the domain to be ligated.

For example, in the case where a ligation site sequence (first ligation element) formed by ligating two A domains of Protein A is changed into a mutated ligation site sequence (mutated first ligation element), a sequence formed by substituting the C-terminal lysine (K) with an amino acid other than lysine (K) and arginine (R) is preferred.

Specifically, a sequence formed by substituting the C-terminal lysine (K) with asparagine (N), aspartic acid (D), or histidine (H), a sequence formed by substituting A at position 1 and F at position 5 with asparagine (N), aspartic acid (D), or histidine (H) in addition to the C-terminal lysine (K), and the like can be exemplified as preferred examples.

In the protein of the second aspect in the first embodiment of the present invention, in the ligation site sequence (first ligation element) of the wild-type amino acid sequence, two Ks are included at the C terminus and at position 4, and the mutated ligation site sequence (mutated first ligation element) is preferably a sequence formed by substituting the C-terminal lysine (K) and lysine (K) at position 4 of the domain to be ligated.

For example, in the case where a ligation site sequence (first ligation element) formed by ligating two B domains of Protein A is changed into a mutated ligation site sequence (mutated first ligation element), a sequence formed by substituting the C-terminal lysine (K) and lysine (K) at position 4 with an amino acid other than lysine (K) and arginine (R) is preferred. Specifically, a sequence formed by substituting the C-terminal lysine (K) and lysine (K) at position 4 with asparagine (N), aspartic acid (D), or histidine (H), a sequence formed by substituting V at position 1 and F at position 5 with asparagine (N), aspartic acid (D), or histidine (H) in addition to the C-terminal K and K at position 4, and the like can be exemplified as preferred examples.

Further, in the case where either one of the Ks included in the ligation site sequence (first ligation element) is deleted by the above-mentioned method, only the C-terminal K may be substituted or only K at position 4 may be substituted.

In the mutated ligation site sequence (mutated first ligation element), in addition to the 5 amino acids included in the wild-type amino acid sequence, an additional amino acid sequence may be inserted.

In the protein in the first embodiment of the present invention, when a mutated ligation site sequence (mutated first ligation element) is formed by deleting or substituting the C-terminal lysine (K) and/or lysine (K) at position 4, the resistance to a serine protease can be enhanced. Further, in the protein of the first embodiment of the present invention, when a mutated ligation site sequence (mutated first ligation element) composed of four amino acids is formed by deleting the terminal lysine (K) and/or lysine (K) at position 4, the resistance to a serine protease such as trypsin or plasmin can be further enhanced, and therefore, such a case is preferred.

Further, although the reason is not clear, when a mutated ligation site sequence (mutated first ligation element) composed of preferably three amino acids, more preferably two amino acids is formed by deleting several amino acids in addition to K in the ligation site sequence (first ligation element) of the wild-type amino acid sequence, the resistance to a serine protease is likely to be further enhanced, and therefore, such a case is preferred. This is presumed to be because by decreasing the length of the ligation site sequence (first ligation element), a physical contact with the protease is suppressed.

The protein in the first embodiment of the present invention may have resistance to another protease in addition to resistance to a serine protease. For example, in the case where the mutated ligation site sequence (mutated first ligation element) is composed of an amino acid other than a hydrophobic amino acid, it has resistance to thermolysin, and therefore, such a case is preferred.

The modification of the amino acid sequence to be introduced other than the mutated ligation site sequence (mutated first ligation element) is not particularly limited, and may be any as long as it has decreased affinity for the Fab region of an immunoglobulin and has affinity for an immunoglobulin comparable to or higher than the protein having a wild-type amino acid sequence.

The amino acid sequence of a portion other than the mutated ligation site sequence (mutated first ligation element) may be any as long as it has a sequence identity of preferably 85% or more, more preferably 90% or more with any of the wild-type amino acid sequences of the E, D, A, B, C, and Z domains of Protein A, and as a result, the protein in the first embodiment of the present invention has an ability to bind to the Fc region.

Each domain of the protein obtained by introducing a mutation has an amino acid sequence identity of preferably 85% or more, more preferably 90% or more with any of the wild-type amino acid sequences of the E, D, A, B, C, and Z domains of Protein A.

Specific examples of the above-mentioned protein include proteins composed of any of amino acid sequences represented by SEQ ID NOS: 48 to 57.

The protein in the first embodiment of the present invention is characterized by having resistance to a protease, particularly a serine protease. The serine protease includes trypsin, plasmin, and the like as examples and is a protease which is generally produced and accumulated in a microorganism such as E. coli or cultured cells such as CHO cells.

For example, in the case where the protein in the first embodiment of the present invention is prepared, in general, as described later, a transformant using a microorganism such as E. coli as a host is utilized, and the protein is accumulated inside or outside the cells of the transformant, and collected. When the target protein is accumulated and collected, the protein is sometimes affected by a protease produced by a microorganism to be used as a host.

Further, in the case where an affinity separation agent is prepared by using the protein in the first embodiment of the present invention as an immunoglobulin-binding affinity ligand, and used for purifying an immunoglobulin, the protein is sometimes affected by a protease contained in a culture supernatant of CHO cells or the like having produced the immunoglobulin to be allowed to pass through the affinity separation agent.

According to the studies conducted by the present inventors, it was found that in the case of a multimer protein having a wild-type amino acid sequence, when the multimer protein is accumulated and collected, during cultivation and in a step of purification, condensation, or the like after collection, the protein is cleaved due to the effect of a protease, and therefore, a target multimer protein cannot be obtained.

It was also revealed that in the case where an affinity separation agent is prepared by using a multimer protein having a wild-type amino acid sequence as a ligand, the multimer protein to serve as a ligand is cleaved due to the effect of a protease when it is used for purification of an immunoglobulin, and does not sufficiently exhibit its immunoglobulin-binding property. It was revealed for the first time that this is due to the effect of a serine protease produced by a microorganism such as E. coli, cultured cells such as CHO cells, or the like among the proteases, and a specific portion in the amino acid sequence of each domain is cleaved.

In consideration of the results of these studies, the protein in the first embodiment of the present invention formed by adding a specific modification to the ligation site sequence (first ligation element) can be accumulated and collected without being cleaved by a serine protease during cultivation and in a step of purification, condensation, or the like after collection.

Further, in the case where an affinity separation agent is prepared by using the multimer protein in the first embodiment of the present invention as a ligand, the protein exhibits a sufficient immunoglobulin-binding property without being affected by a serine protease, and therefore, a target immunoglobulin can be purified.

From the viewpoint that an advantage that a ligand can stably function without being affected by a protease when it is used in a step of purification of an immunoglobulin or the like is remarkably exhibited, the protein in the first embodiment of the present invention preferably includes one or more non-immobilized domains which are not bound to a support, more preferably two or more non-immobilized domains, and in the case of an n-mer protein, it is preferred that the (n−1) or more domains are non-immobilized domains, and it is most preferred that all the n domains are non-immobilized domains.

In order for the protein in the first embodiment of the present invention to include a non-immobilized domain, which will be described in detail later, in the amino acid sequence of at least one or more domains, an amino acid residue which is useful for immobilization is introduced by substitution, insertion, or the like of an amino acid, or an amino acid which is useful for immobilization is deleted, a tag for immobilization is introduced, etc., whereby such a protein can be prepared.

By including a non-immobilized domain in the protein in the first embodiment of the present invention, the protein can be immobilized on a support by adjusting the orientation, and a higher immunoglobulin-binding property can be exhibited, and therefore, such a case is preferred.

Further, even if the affinity separation agent in the first embodiment of the present invention is repeatedly used, the immunoglobulin-binding property of the ligand is not decreased, and therefore, an immunoglobulin can be efficiently purified.

Due to this, the protein in the first embodiment of the present invention has a sufficiently high binding activity to the Fc region of an immunoglobulin and therefore can be favorably used as an affinity ligand, and also can be repeatedly used as the ligand stably, and thus is industrially advantageous.

Here, in this description, whether or not the protein has resistance to a serine protease is confirmed by the following method. When a solution obtained by adding 2 µL of a 1 to 10 mg/mL serine protease solution to 10 µL of a 2 mg/mL ligand solution is heated to 37° C. for 15 hours, the larger the amount of the uncleaved ligand, the more preferred the protein. The concentration of the serine protease solution may be set as appropriate according to the type of the protease, and for example, is set to preferably 1 mg/mL in the case of trypsin, and is set to preferably 10 mg/mL in the case of plasmin.

As the protein which has resistance to a serine protease, the uncleaved ligand is maintained at 80% or more, preferably 85% or more, more preferably 90% or more. Incidentally, whether or not the ligand is cleaved is confirmed by commonly used electrophoresis (SDS-PAGE).

Second Embodiment of the Invention

<Protein>

The protein in the second embodiment of the present invention is characterized in that the protein has two or more domains derived from any of A, B, C, and Z domains of Protein A represented by SEQ ID NOS: 3 to 6, and at least one ligation element (second ligation element) which ligates each domain is a mutated ligation element (mutated second ligation element) which is composed of one or more amino acids, and is constituted by an amino acid other than a hydrophobic amino acid.

Protein A is a protein constituted by five immunoglobulin-binding domains in a connected form. A plurality of microorganisms express Protein A, and examples of the microorganism which expresses Protein A include *Staphylococcus*.

The A, B, C, and Z domains of Protein A represented by SEQ ID NOS: 3 to 6 are immunoglobulin-binding proteins capable of binding to a region other than the complementarity-determining regions (CDRs) of an immunoglobulin, and all the domains bind to each region of the Fc region and the Fab region of an immunoglobulin, and particularly the Fv region in the Fab region.

As shown in the sequence comparison table of FIG. 1, the A, B, C. and Z domains derived from Protein A have amino acid sequences with a high homology with one another, and have an amino acid sequence identity of 80% or more. Incidentally, the hyphen (-) indicates that it is the same amino acid residue as that of the C domain.

The "domain derived from any of the A, B, C, and Z domains of Protein A" refers to a domain having an amino acid sequence derived from the amino acid sequence of each of the wild-type domains, and a mutation other than e below-mentioned mutated ligation element (mutated second ligation element) may be included in the amino acid sequence of each of the wild-type domains as long as it encodes a protein having an ability to bind to the Fc region.

That is, the amino acid sequence of any of the A, B, C, and Z domains of Protein A is the amino acid sequence before a mutation is introduced (wild-type amino acid sequence), and the amino acid sequence of the "domain derived from any of the A, B, C, and Z domains of Protein A" refers to the wild-type amino acid sequence of the A, B, C, or Z domain itself, or an amino acid sequence which includes the below-mentioned mutated ligation element (mutated second ligation element) in the wild-type amino acid sequence, and/or is partially modified by substitution, insertion, deletion, or chemical modification of an amino acid.

Here, the Z domain of Protein A is a domain obtained by introducing mutations A1V and G29A into the B domain, and is not present in natural Protein A, however, in this description, the amino acid sequence represented by SEQ ID NO: 6 is referred to as "the wild-type amino acid sequence of the Z domain".

The protein in the second embodiment of the present invention is a multimer protein (multi-domain protein) having two or more domains, each of which is the "domain derived from any of A, B, C, and Z domains of Protein A" described above as a single domain. The protein has preferably 3 or more domains, more preferably 4 or more domains, and preferably 10 or less domains, more preferably 8 or less domains, further more preferably 6 or less domains.

Such a multimer protein may be a homopolymer such as a homodimer or a homotrimer, which is a connected body of a single immunoglobulin-binding domain, or may be a heteropolymer such as a heterodimer or a heterotrimer, which is a connected body of different types of immunoglobulin-binding domains. It is preferred that all the domains included in the protein in the second embodiment of the present invention are homopolymers derived from any one type of the amino acid sequences of the A, B, C, and Z domains of Protein A represented by SEQ ID NOS: 3 to 6.

In the protein in the second embodiment of the present invention, the C terminus and the N terminus of two or more domains are ligated to form a ligation element (second ligation element). Here, in the second embodiment of the present invention, the "ligation element (second ligation element)" refers to a sequence at positions 1-5 in the amino acid sequence of each domain.

That is, in a domain to which another domain is ligated at the N-terminal side, a sequence at positions 1-5 in the amino acid sequence of the domain becomes the ligation element (second ligation element). Therefore, in an n-mer protein, (n–1) ligation elements (second ligation elements) are present.

The sequences shown below are sequences at positions 1-5 in the amino acid sequences of the A, B, C, and Z domains of Protein A. Any of the sequences is composed of 5 amino acids, and includes alanine (A) and/or phenylalanine (F), each of which is a hydrophobic amino acid.

| | |
|---|---|
| A domain | A D N N F |
| B domain | A D N K F |
| C domain | A D N K F |
| Z domain | V D N K F |

The protein in the second embodiment of the present invention is characterized in that at least one ligation element (second ligation element) is a mutated ligation element (mutated second ligation element) partially modified by substitution, insertion, deletion, or chemical modification of an amino acid. The mutated ligation element (mutated second ligation element) is a sequence composed of one or more amino acids and constituted by an amino acid other than a hydrophobic amino acid.

At least one of the ligation elements (second ligation elements) included in the protein in the second embodiment of the present invention may be a mutated ligation element (mutated second ligation element). However, in the case of a trimer or higher-order multimer protein, it is preferred that two or more of them are mutated ligation elements (mutated second ligation elements), and in the case of an n-mer protein, it is more preferred that (n–1) of them are mutated ligation elements (mutated second ligation elements), that is, all the ligation elements (second ligation elements) are mutated ligation elements (mutated second ligation elements).

The ligation element (second ligation element) is composed of a sequence at positions 1-5 in the amino acid sequence of each domain, and a sequence which is obtained by performing modification for this sequence through substitution, insertion, deletion, or chemical modification, and therefore is composed of one or more amino acids and is constituted by an amino acid other than a hydrophobic amino acid is a mutated ligation element (mutated second ligation element).

According to the studies conducted by the present inventors, it was revealed that a site which is likely to be cleaved by thermolysin is on the N-terminal side of a hydrophobic amino acid in the ligation element (second ligation element). Based on this, it was found that by changing the ligation element (second ligation element) into a mutated ligation element (mutated second ligation element) constituted by an amino acid other than a hydrophobic amino acid, the cleavage of the protein by thermolysin can be significantly suppressed.

Specifically, it is preferred to form a mutated ligation element (mutated second ligation element) by deleting and/ or substituting A and F in the ligation element (second ligation element) of the wild-type amino acid sequence.

Here, in this description, the "hydrophobic amino acid" refers to alanine (A), isoleucine (I), leucine (L), phenylalanine (F), proline (P), tryptophan (W), or valine (V), and the "amino acid other than a hydrophobic amino acid" refers to a hydrophilic amino acid such as arginine (R), asparagine (N), aspartic acid (D), glutamine (Q), glutamic acid (E), histidine (H), or lysine (K); a natural neutral amino acid such as cysteine (C), glycine (G), methionine (M), serine (S), threonine (T), or tyrosine (Y); an unnatural neutral amino acid such as acetyllysine, azido-Z-lysine, glutamic acid 5-methyl ester, or aspartic acid 5-methyl ester.

Hereinafter, specific examples of the mutated ligation element (mutated second ligation element) will be described.

In the case where a mutated ligation element (mutated second ligation element) is formed by deleting some of the amino acids of the ligation element (second ligation element), it is essential that the mutated ligation element (mutated second ligation element) be composed of one or more amino acids. According to the studies conducted by the present inventors, it was revealed that in the case where all the 5 amino acids included in the ligation element (second ligation element) are deleted, the ability to bind to a target immunoglobulin is significantly decreased, and when the protein is used as an affinity ligand, the ability to bind to the immunoglobulin is insufficient. In particular, the difference remarkably appears depending on the condition for purification in which the protein is used as an affinity separation agent.

In general, an immunoglobulin is larger than each domain, and the number of immunoglobulins capable of binding to each domain is limited due to the steric hindrance of the bound immunoglobulin molecules. Due to this, it is presumed that when each domain and an immunoglobulin are bound to each other, if the ligation element (second ligation element) is not present and adjacent domains are too close to each other, a space enabling the immunoglobulin to bind thereto is lacking, and thus the number of immunoglobulins to be bound per domain is decreased. For the reason that the mutated ligation element (mutated second ligation element) has an excellent ability to bind to an immunoglobulin under various purification conditions, it is essential that the element be composed of one or more amino acids, and when the element is composed of two or more amino acids, the ability to bind to a target immunoglobulin is likely to be further enhanced, and therefore such a case is preferred.

In the case where the mutated ligation element (mutated second ligation element) is included in a domain derived from any of the A, B, and C domains of Protein A, the mutated ligation element (mutated second ligation element) is preferably an element which is composed of a sequence at positions 1-5 in the amino acid sequence of the A, B, or C domain, and is formed by deleting alanine at position 1 and/or phenylalanine at position 5.

For example, a sequence which is formed by deleting two amino acids: alanine (A) at position 1 and phenylalanine (F) at position 5 and therefore is composed of three amino acids: aspartic acid (D), asparagine (N), and lysine (K), a sequence which is formed by deleting K at position 4 in addition to A at position 1 and F at position 5 and therefore is composed of two amino acids: D and N, and the like can be exemplified as preferred examples. Further, in the case where a hydrophobic amino acid included in the ligation element (second ligation element) is substituted by the below-mentioned method, only A at position 1 may be deleted or only F at position 5 may be deleted.

In the case where the mutated ligation element (mutated second ligation element) is included in a domain derived from the Z domain of Protein A, the mutated ligation element (mutated second ligation element) is preferably an element which is composed of a sequence at positions 1-5 in the amino acid sequence of the Z domain, and is formed by deleting valine at position 1 and/or phenylalanine at position 5.

For example, a sequence which is formed by deleting two amino acids: valine (V) at position 1 and phenylalanine (F) at position 5 and therefore is composed of three amino acids: aspartic acid (D), asparagine (N), and lysine (K), a sequence which is formed by deleting K at position 4 in addition to V at position 1 and F at position 5 and therefore is composed of two amino acids: D and N, and the like can be exemplified as preferred examples. Further, in the case where some of the hydrophobic amino acids included in the ligation element (second ligation element) are substituted by the below-mentioned method, only V at position 1 may be deleted or only F at position 5 may be deleted.

The substitution of an amino acid means a mutation in which the original amino acid is deleted and a different amino acid is added at the same position. The different amino acid to be added is not particularly limited, and for example, a natural constituent amino acid of a protein, a natural non-constituent amino acid of a protein, and an unnatural amino acid can be exemplified. Among these, from the viewpoint of production by genetic engineering, a natural amino acid can be preferably used.

However, in the case where a mutated ligation element (mutated second ligation element) is formed by substituting an amino acid in the ligation element (second ligation element), it is necessary to form a sequence such that a hydrophobic amino acid is not included in the mutated ligation element (mutated second ligation element). Therefore, the amino acid to be introduced by the substitution is not particularly limited as long as it is an amino acid other than a hydrophobic amino acid, but is preferably any of hydrophilic amino acids such as arginine (R), asparagine (N), aspartic acid (D), glutamine (Q), glutamic acid (E), histidine (H), and lysine (K); and neutral amino acids such as cysteine (C), glycine (G), methionine (M), serine (S), threonine (T), and tyrosine (Y). Among these, the amino acid is more preferably any of the above-mentioned hydrophilic amino acids.

Further, from the viewpoint that the stability under an alkaline condition is improved, arginine (R), aspartic acid (D), glutamine (Q), glutamic acid (E), histidine (H), and lysine (K) are preferred.

In addition, from the viewpoint that the resistance to another protease, for example, the below-mentioned serine protease is improved, aspartic acid (D), glutamine (Q), glutamic acid (E), and histidine (H) are preferred.

In the case where the mutated ligation element (mutated second ligation element) is included in a domain derived from any of the A, B, and C domains of Protein A, the mutated ligation element (mutated second ligation element) is preferably an element which is composed of a sequence at positions 1-5 in the amino acid sequence of the A, B, or C domain, and is formed by substituting alanine at position 1 and/or phenylalanine at position 5 with an amino acid other than a hydrophobic amino acid.

For example, a sequence formed by substituting two amino acids: alanine (A) at position 1 and phenylalanine (F)

at position 5 with an amino acid other than a hydrophobic amino acid, a sequence formed by substituting K at position 4 with an amino acid other than a hydrophobic amino acid excluding K in addition to A at position 1 and F at position 5, and the like can be exemplified as preferred examples. Further, in the case where some of the hydrophobic amino acids included in the ligation element (second ligation element) are deleted by the above-mentioned method, only A at position 1 may be substituted or only F at position 5 may be substituted.

In the case where the mutated ligation element (mutated second ligation element) is included in a domain derived from the Z domain of Protein A, the mutated ligation element (mutated second ligation element) is preferably an element which is composed of a sequence at positions 1-5 in the amino acid sequence of the Z domain, and is formed by substituting valine at position 1 and/or phenylalanine at position 5 with an amino acid other than a hydrophobic amino acid.

For example, a sequence formed by substituting two amino acids: valine (V) at position 1 and phenylalanine (F) at position 5 with an amino acid other than a hydrophobic amino acid, a sequence formed by substituting K at position 4 with an amino acid other than a hydrophobic amino acid excluding K in addition to V at position 1 and F at position 5, and the like can be exemplified as preferred examples. Further, in the case where some of the hydrophobic amino acids included in the ligation element (second ligation element) are deleted by the above-mentioned method, only V at position 1 may be substituted or only F at position 5 may be substituted.

In the mutated ligation element (mutated second ligation element), in addition to the 5 amino acids included in the wild-type amino acid sequence, an additional amino acid sequence may be inserted. For example, it is also possible to form a mutated ligation element (mutated second ligation element) composed of 6 or more amino acids by further inserting an amino acid other than a hydrophobic amino acid into a sequence formed by substituting some of the hydrophobic amino acids included in the ligation element (second ligation element) by the above-mentioned method.

In addition, from a sequence formed by deleting some of the hydrophobic amino acids included in the ligation element (second ligation element) by the above-mentioned method, further some or all of the amino acids are deleted, and then, an arbitrary mutated ligation element (mutated second ligation element) composed of an amino acid other than a hydrophobic amino acid can also be inserted. Further, chemical modification such as acetylation of a lysine residue or hydroxylation of a proline residue, or the like can be also performed within the range in which the binding property to an antibody or the like is not affected.

However, if the conformation of a protein to be obtained is largely changed, the affinity for a target immunoglobulin or the ability to bind thereto may be changed, and therefore, it is preferred that an additional amino acid sequence is not further inserted into the ligation element (second ligation element) of the wild-type amino acid sequence.

The amino acid constituting the mutated ligation element (mutated second ligation element) in which a mutation is introduced by substitution, insertion, or the like is not particularly limited as long as it is an amino acid other than a hydrophobic amino acid, but is preferably a hydrophilic amino acid such as arginine (R), asparagine (N), aspartic acid (D), glutamine (Q), glutamic acid (E), histidine (H), or lysine (K), more preferably asparagine (N), aspartic acid (D), or histidine (H).

The modification of the amino acid sequence to be introduced other than the mutated ligation element (mutated second ligation element) is not particularly limited, and may be any as long as it has affinity for an immunoglobulin and an ability to bind thereto comparable to or higher than the protein having a wild-type amino acid sequence.

The amino acid sequence of a portion other than the mutated ligation element (mutated second ligation element) ay be any as long as it has a sequence identity of preferably 85% or more, more preferably 90% or more with any of the wild-type amino acid sequences of the A, B, C, and Z domains of Protein A, and as a result, the protein in the second embodiment of the present invention has an ability to bind to the Fc region.

Each domain of the protein obtained by introducing a mutation has an amino acid sequence identity of preferably 85% or more, more preferably 90% or more with any of the wild-type amino acid sequences of the A, B, C, and Z domains of Protein A.

As a useful index of characteristics of the ligand other than affinity for an immunoglobulin and an ability to bind thereto, alkali resistance and weak acidic elutability can be exemplified. Modification of an amino acid sequence other than the mutated ligation element (mutated second ligation element) for improving these can be achieved in the present invention, and can be said to be a preferred embodiment.

The "alkali resistance" refers to a property in which when a protein is immersed in an alkaline solution such as 0.1 N NaOH or 0.5 N NaOH, the protein maintains high affinity for an immunoglobulin and a high ability to bind thereto. According to this, when a separating agent is formed by using a protein having alkali resistance as an affinity ligand, even if washing with an alkaline solution is repeated, a high separation and purification ability can be maintained. Incidentally, the C domain and the Z domain have been known to have high alkali resistance in the first place, and are preferred sequences in terms of alkali resistance.

Further, the "weak acidic elutability" refers to a property in which when an immunoglobulin is adsorbed and purified using a separating agent formed by immobilizing an affinity ligand, the immunoglobulin which is generally eluted at an acidic pH can be eluted under a milder condition of a higher pH. According to this, it is possible to suppress denaturation such as protein aggregation when performing elution. A mutation for imparting weak acidic elutability described in PTL 5, WO 2010/118699, or the like can be also achieved in the present invention, and can be said to be a preferred embodiment.

Specific examples of the above-mentioned protein include proteins composed of any of amino acid sequences represented by SEQ ID NOS: 105 to 115.

The protein in the second embodiment of the present invention is characterized by having resistance to a protease, particularly thermolysin. In the case where the protein in the second embodiment of the present invention is produced, in general, as described later, a transformant using a microorganism as a host is utilized, and the protein is accumulated inside or outside the cells of the transformant, and collected. When the target protein is accumulated and collected, the protein is sometimes affected by a protease produced by a microorganism to be used as a host.

According to the studies conducted by the present inventors, it was found that in the case of a multimer protein having a wild-type amino acid sequence is accumulated and collected by the above-mentioned method, during cultivation and in a step of purification, condensation, or the like after collection, the protein is cleaved due to the effect of a protease, and therefore, a target multimer protein cannot be obtained. It was revealed for the first time that this is due to the effect of thermolysin produced by a bacterium of the genus *Bacillus* or the like among the proteases, and a specific portion in the amino acid sequence of each domain is cleaved.

In consideration of the results of these studies, the protein in the second embodiment of the present invention formed by adding a specific modification to the ligation element (second ligation element) can be accumulated and collected without being cleaved by thermolysin during cultivation and in a step of purification, condensation, or the like after collection. Due to this, the protein in the second embodiment of the present invention has a sufficiently high binding activity to the Fc region of an immunoglobulin, and therefore can be favorably used as an affinity ligand, and also can be produced with high efficiency, and thus is industrially advantageous.

Here, in this description, whether or not the protein has resistance to thermolysin is confirmed by the following method. When a solution obtained by adding 2 µL of a 1 mg/mL thermolysin solution to 10 µL of a 2 mg/mL ligand solution is heated to 37° C. for 15 hours, the larger the amount of the uncleaved ligand, the more preferred the protein. For example, it is preferred that the uncleaved ligand is maintained at 80% or more, preferably 85% or more, more preferably 90% or more. Incidentally, whether or not the ligand is cleaved is confirmed by commonly used electrophoresis (SDS-PAGE).

The protein in the second embodiment of the present invention has resistance to thermolysin because of having the mutated ligation element (mutated second ligation element), but is preferably an amino acid sequence further having resistance to another protease. Examples of another protease include serine proteases such as trypsin and plasmin.

In the case where an IgG antibody produced in recombinant cultured cells is purified using an affinity separation agent in which the protein in the second embodiment of the present invention is used as a ligand, the ligand may be cleaved by a serine protease produced by the cultured cells, and a sufficient immunoglobulin-binding property may not be able to be exhibited. Therefore, the protein in the second embodiment of the present invention is preferably an amino acid sequence further having resistance to a serine protease.

Due to the above-mentioned reason, the protein is preferably a protein in which the C-terminal lysine in the amino acid sequence of at least one domain is deleted or substituted. According to the studies conducted by the present inventors, it was revealed that a site which is likely to be cleaved by a serine protease such as trypsin or plasmin is on the C-terminal side of the C-terminal lysine (K) present in the wild-type amino acid sequence of each domain. Based on this, it was found that by constituting the protein by an amino acid sequence which does not include the C-terminal lysine (K), to which the ligation element (second ligation element) is bound, of each domain by deletion or substitution, the cleavage of the protein by a serine protease can be significantly suppressed.

The protein is more preferably a protein in which in a domain to which the mutated ligation element (mutated second ligation element) is bound on the C-terminal side, the C-terminal lysine in the amino acid sequence of the domain is deleted or substituted.

The protein is more preferably a protein which does not include lysine also in the mutated ligation element (mutated second ligation element). As described previously, in the wild-type amino acid sequence of each of the B, C, and Z domains, lysine is included at position 4 in the ligation element (second ligation element).

According to the studies conducted by the present inventors, it was revealed that also lysine in the ligation element (second ligation element) is relatively likely to be cleaved by a serine protease, and therefore, in the mutated ligation element (mutated second ligation element), it is preferred to form an amino acid sequence which does not include lysine (K) by deletion or substitution. It is more preferred that the mutated ligation element (mutated second ligation element) does not include arginine (R).

Hereinafter, specific examples of the mutated ligation element having resistance to a serine protease will be described.

A case where the C-terminal lysine (K) of each domain and/or some of the amino acids of the ligation element (second ligation element) are deleted can be exemplified. In the case where the ligation element (second ligation element) is composed of a sequence at positions 1-5 in the amino acid sequence of the A domain, only the C-terminal K of each domain may be deleted.

On the other hand, in the case where the ligation element (second ligation element) is composed of a sequence at positions 1-5 in the amino acid sequence of any of the B, C, and Z domain, two Ks are included at the C terminus and at position 4, and it is preferred that at least the C-terminal K is deleted, and it is more preferred that also K in the ligation element (second ligation element) is deleted.

For example, in the case where the ligation element (second ligation element) formed by ligating two B domains of Protein A is a mutated ligation element (mutated second ligation element) formed by deleting a hydrophobic amino acid, a sequence which is formed by further deleting the C-terminal lysine (K) and therefore is composed of three amino acids: aspartic acid (D), asparagine (N), and lysine (K), a sequence which is formed by further deleting two amino acids: the C-terminal lysine (K) and lysine (K) at position 4 and therefore is composed of two amino acids: aspartic acid (D) and asparagine (N), and the like can be exemplified as preferred examples.

Further, in the case where either one of the C-terminal K and K included in the ligation element (second ligation element) is substituted by the below-mentioned method, only the C-terminal K may be deleted or only K at position 4 may be deleted.

In the case where the C-terminal K of each domain and/or some of the amino acids in the ligation element (second ligation element) are substituted, a method in which the original amino acid is deleted and a different amino acid is added at the same position can be exemplified. The different amino acid to be added is not particularly limited, and for example, a natural constituent amino acid of a protein, a natural non-constituent amino acid of a protein, and an unnatural amino acid can be exemplified. Among these, from the viewpoint of production by genetic engineering, a natural amino acid can be preferably used.

However, in the case where a mutated ligation element (mutated second ligation element) is formed by substituting an amino acid in the ligation element (second ligation element), it is necessary to constitute the element by an amino acid other than a hydrophobic amino acid, and it is preferred that the sequence is formed such that lysine (K) is not included in the mutated ligation element (mutated second ligation element). Further, when the sequence is a sequence which does not include arginine (R) either, the resistance to a protease which recognizes arginine is also improved, and therefore, such a case is preferred.

Therefore, the amino acid to be introduced by the substitution is not particularly limited as long as it is an amino acid other than a hydrophobic amino acid, lysine (K), and arginine (R), but is preferably any of hydrophilic amino acids such as asparagine (N), aspartic acid (D), glutamine (Q), glutamic acid (E), and histidine (H); and neutral amino acids such as cysteine (C), glycine (G), methionine (M), serine (S), threonine (T), and tyrosine (Y). Among these, the amino acid is more preferably any of the above-mentioned hydrophilic amino acids. Further, from the viewpoint that the stability under an alkaline condition is improved, aspartic acid (D), glutamine (Q), glutamic acid (E), and histidine (H) are preferred.

In the case where the ligation element (second ligation element) is composed of a sequence at positions 1-5 in the amino acid sequence of the A domain, only the C-terminal K of each domain may be substituted. On the other hand, in the case where the ligation element (second ligation element) is composed of a sequence at positions 1-5 in the amino acid sequence of any of the B, C, and Z domains, two Ks are included at the C terminus and at position 4, and it is preferred that at least the C-terminal K is substituted, and it is more preferred that also K in the ligation element (second ligation element) is substituted.

For example, in the case where the ligation element (second ligation element) formed by ligating two B domains of Protein A is a mutated ligation element (mutated second ligation element) formed by substituting a hydrophobic amino acid, the element is preferably an element formed by further substituting the C-terminal lysine (K) with an amino acid other than a hydrophobic amino acid, lysine (K), and arginine (R), more preferably an element formed by further substituting two amino acids: the C-terminal lysine (K) and lysine (K) at position 4 with an amino acid other than a hydrophobic amino acid, lysine (K), and arginine (R). Specifically, a sequence formed by substituting the C-terminal K and K at position 4 with asparagine (N), aspartic acid (D), or histidine (H) in addition to V at position 1 and F at position 5, and the like can be exemplified as preferred examples.

Further, in the case where either one of the C-terminal K and K included in the ligation element (second ligation element) is deleted by the above-mentioned method, only the C-terminal K may be substituted or only K at position 4 may be substituted.

By adding the above-mentioned mutation, the protein in the second embodiment of the present invention can have resistance to a serine protease. The serine protease includes trypsin, plasmin, and the like as examples and is a protease which is generally produced and accumulated in a microorganism such as *E. coli* or cultured cells such as CHO cells.

In the case where an affinity separation agent is prepared by using the protein in the second embodiment of the present invention as an immunoglobulin-binding affinity ligand, and used for purifying an immunoglobulin, the protein is sometimes affected by a protease contained in a culture supernatant of CHO cells or the like having produced an antibody to be allowed to pass through the affinity separation agent.

According to the studies conducted by the present inventors, it was revealed for the first time that a specific portion in the amino acid sequence of each domain is cleaved due to the effect of a serine protease. In consideration of the results of these studies, in the case where an affinity separation agent is prepared by using the protein in the second embodiment of the present invention modified into an amino acid sequence having resistance to a serine protease as a ligand, a sufficient immunoglobulin-binding property is exhibited without being affected by a serine protease, and thus, a target immunoglobulin can be purified.

Further, even if the affinity separation agent in the second embodiment of the present invention is repeatedly used, the immunoglobulin-binding property of the ligand is not decreased, and therefore, an immunoglobulin can be efficiently purified.

Due to this, the protein in the second embodiment of the present invention has a sufficiently high binding activity to the Fc region of an immunoglobulin and therefore can be favorably used as an affinity ligand, and also can be repeatedly used as the ligand stably, and thus is industrially advantageous.

Here, in this description, whether or not the protein has resistance to a serine protease is confirmed by the following method. When a solution obtained by adding 2 µL of a 1 to 10 mg/mL serine protease solution to 10 µL of a 2 mg/mL ligand solution is heated to 37° C. for 15 hours, the larger the amount of the uncleaved ligand, the more preferred the protein. The concentration of the serine protease solution may be set as appropriate according to the type of the protease, and for example, is set to preferably 1 mg/mL in the case of trypsin, and is set to preferably 10 mg/mL in the case of plasmin.

As the protein which has resistance to a serine protease, the uncleaved ligand is maintained at 80% or more, preferably 85% or more, more preferably 90% or more. Incidentally, whether or not the ligand is cleaved is confirmed by commonly used electrophoresis (SD S-PAGE).

<Method for Producing Protein>

A method for producing the proteins of the first embodiment and the second embodiment of the present invention (protein of the present invention) will be described below.

The protein of the present invention can be produced by preparing a DNA having a base sequence encoding the above-mentioned protein and translating the DNA. Specifically, the protein can be produced by utilizing a transformant obtained by transforming a microorganism to serve as a host using a vector including the DNA, or a cell-free protein synthesis system using the DNA.

The DNA having a base sequence encoding the protein of the present invention can be obtained by utilizing a conventionally used known method, for example, a polymerase chain reaction (hereinafter abbreviated as "PCR") method. In addition, the protein can be also synthesized by a known chemical synthesis method, and further, it can be also obtained from a genomic DNA library. In the base sequence constituting the DNA, a codon may be substituted with a degenerate codon, and it is not necessary that the base sequence be the same as the original base sequence as long as it encodes the same amino acid when it is translated.

As for a method for site-specifically introducing a mutation into the DNA encoding the protein of the present invention, as described below, it can be performed using a gene recombination technique, a PCR method, or the like.

That is, the introduction of a mutation by a gene recombination technique can be performed by, for example, a cassette mutation method in which in the case where an appropriate restriction enzyme recognition sequence is present on both sides of a target site where the mutation is desired to be introduced in a gene encoding the protein of the present invention, the portions of the restriction enzyme recognition sequence are cleaved with the restriction enzyme, a region including the site where the mutation is desired to be introduced is removed, and thereafter, a DNA fragment in which the mutation has been introduced is inserted only into the target site by chemical synthesis or the like.

Further, the introduction of a site-specific mutation by PCR can be performed by, for example, a double primer method in which PCR is performed using two types of synthetic oligoprimers including a complementary mutation in each of the + and − chains and also using a double-stranded plasmid encoding the protein as a template.

Further, it is also possible to prepare a DNA encoding the multimer protein by ligating the desired number of DNAs encoding the monomer protein (one domain) of the present invention in series. For example, as for the method for ligating the DNAs encoding the multimer protein, an appropriate restriction enzyme site is introduced into the DNA sequence, and a double-stranded DNA fragmented by the restriction enzyme can be ligated using a DNA ligase. The restriction enzyme site may be one type, however, a plurality of different types of restriction enzyme sites can be also introduced.

The method for preparing a DNA encoding the multimer protein is not limited to these ligation methods. For example, it is also possible to perform the preparation by applying the above-mentioned mutation introduction method to a DNA encoding Protein A (for example, WO 2006/004067).

Further, in the case where the base sequences encoding the respective monomer proteins are the same in the DNA encoding the multimer protein, homologous recombination may be induced in the host, and therefore, it is preferred that the sequence identity between the base sequences of the DNAs encoding the ligated monomer proteins is preferably 90% or less, more preferably 85% or less.

The vector includes a DNA including a base sequence encoding the above-mentioned protein or a partial amino acid sequence thereof and a promoter which can function in the host and is ligated so as to be able to act on the base sequence. In general, it can be obtained by ligating or inserting the DNA including a gene encoding the above-mentioned protein into an appropriate vector.

The vector for inserting the gene is not particularly limited as long as it can autonomously replicate in the host, and a plasmid DNA or a phage DNA can be used as the vector. For example, in the case where *E. coli* is used as the host, examples of the vector include pQE series vectors (manufactured by Qiagen, Inc.), pET series vectors (manufactured by Merck, Inc.), and pGEX series vectors (manufactured by GE Healthcare Japan Ltd.).

In the case where a bacterium of the genus *Brevibacillus* is used as the host for transformation, examples of the vector include those known as *Bacillus subtilis* vectors such as pUB110 and pHY500 (JP-A-2-31682), pNY700 (JP-A-4-278091), pNU211R2L5 (JP-A-7-170984), and pHT210 (JP-A-6-133782), and those known as shuttle vectors for *E. coli* and a bacterium of the genus *Brevibacillus* such as pNCMO2 (JP-A-2002-238569).

By introducing such a vector including a DNA encoding the protein of the present invention into a cell to serve as the host, a transformant can be obtained. Examples of a method for transfecting the vector into the host include a method using calcium ions, an electroporation method, a spheroplast method, a lithium acetate method, an Agrobacterium infection method, a particle gun method, and a polyethylene glycol method, but the method is not limited thereto.

Further, examples of a method for maintaining the vector in the host include a method for maintaining the vector independently of the genome (chromosome) in the cell by autonomous replication of the vector, and a method for maintaining the vector dependently on the replication of the genome by integrating the prepared gene into the genome (chromosome).

The cell to serve as the host is not particularly limited, however, in order to achieve mass production at low cost, preferably, *E. coli*, *Bacillus subtilis*, and bacteria (eubacteria) of the genus *Brevibacillus*, the genus *Staphylococcus*, the genus *Streptococcus*, the genus *Streptomyces*, the genus *Corynebacterium*, etc. can be favorably used. More preferably, gram-positive bacteria such as *Bacillus subtilis* and bacteria of the genus *Brevibacillus*, the genus *Staphylococcus*, the genus *Streptococcus*, the genus *Streptomyces*, the genus *Corynebacterium*, etc. may be used. Still more preferably, bacteria of the genus *Brevibacillus*, whose application example to the mass production of Protein A is known (WO 2006/004067) may be used.

Examples of the bacteria of the *Brevibacillus* include *Brevibacillus agri*, *B. borstelensis*, *B. brevis*, *B. centrosporus*, *B. choshinensis*, *B. formosus*, *B. invocatus*, *B. laterosporus*, *B. limnophilus*, *B. parabrevis*, *B. reuszeri*, and *B. thermoruber*, but the bacterium is limited thereto.

Preferred examples thereof include *Brevibacillus brevis* strain 47 (JCM6285), *Brevibacillus brevis* strain 47K (FERM BP-2308), *Brevibacillus brevis* strain 47-5Q (JCM8970), *Brevibacillus choshinensis* strain HPD31 (FERM BP-1087), and *Brevibacillus choshinensis* strain HPD31-OK (FERM BP-4573).

A mutant strain (or a derivative strain) such as a protease-deficient strain, a high-expression strain, or a sporulation-deficient strain of the bacterium of the genus *Brevibacillus* described above may be used according to the purpose such as improvement of the yield. Specifically, *Brevibacillus choshinensis* HPD31-OK which is a protease mutant strain derived from *Brevibacillus choshinensis* HPD31 (JP-A-6-296485) or *Brevibacillus choshinensis* HPD31-SP3 (WO 05/045005) which does not have a spore-forming ability derived from *Brevibacillus choshinensis* HPD31 can be used.

The protein of the present invention can be produced by utilizing a transformant or a cell-free protein synthesis system using the above-mentioned DNA.

In the case where the protein is produced using a transformant, the protein can be accumulated in the cells (including the inside of the periplasmic region) of the transformant or in the culture solution (outside of the cells) and collected. The accumulation of the protein in the cells is advantageous in that oxidation of the expressed protein can be prevented, and a side reaction with a medium component is not caused. The accumulation of the protein in the periplasmic region is advantageous in that degradation by an intracellular protease can be suppressed.

On the other hand, the secretion of the protein outside the cells of the transformant is advantageous in that a step of homogenization of cells or extraction is not needed, and therefore, the production cost can be kept low. However, in the case where the host also secretes a protease, a target protein may be degraded during cultivation.

As a specific method, in the case where the protein is accumulated in cultured cells (including the inside of periplasmic regions), for example, the cells are collected from a culture solution by a method such as centrifugation or filtration, and subsequently, the cells are homogenized by an ultrasonic homogenization method, a French press method, or the like, and/or a surfactant or the like is added to solubilize the protein, whereby the protein produced and accumulated in the cells can be collected. At this time, if a protease is eluted, the target protein may be degraded.

In the case where a recombinant protein is produced and secreted, a supernatant including the cultured cells and the produced and secreted protein is separated by a general separation method such as centrifugation or filtration after completion of cultivation, whereby the produced recombinant protein can be collected.

In the case where the protein of the present invention is produced by a cell-free protein synthesis system, the cell-free protein synthesis system is not particularly limited as long as it is a system for synthesizing the protein in vitro using a cell extract solution, and for example, a synthesis system derived from prokaryotic cells, plant cells, or higher animal cells, or the like can be used.

The protein of the present invention can be also produced by culturing the above-mentioned transformant in a culture medium, allowing the transformant to express the protein in the form of a fusion protein with another protein, collecting the fusion protein from the culture, cleaving the fusion protein with an appropriate protease, and collecting the desired protein.

A method for culturing the above-mentioned transformant in a culture medium can be performed according to a common method used for culturing a host. The culture medium used for culturing the obtained transformant is not particularly limited as long as the protein can be produced with high efficiency and high yield.

Specifically, a carbon source or a nitrogen source such as glucose, sucrose, glycerol, polypeptone, a meat extract, a yeast extract, or casamino acid can be used. Other than these, an inorganic salt such as a potassium salt, a sodium salt, a phosphate salt, a magnesium salt, a manganese salt, a zinc salt, or an iron salt is added as needed. In the case where an auxotrophic host cell is used, a nutritional substance necessary for its growth may be added to the culture medium. Further, an antibiotic such as penicillin, erythromycin, chloramphenicol, neomycin, or kanamycin may be added as needed.

The culture medium for culturing a transformant obtained using *E. coli* as a host is not particularly limited, however, examples thereof include LB medium (triptone: 1%, yeast extract: 0.5%, NaCl: 1%) and 2× YT medium (triptone: 1.6%, yeast extract: 1.0%, NaCl: 0.5%).

The culture medium for culturing a transformant obtained using a bacterium of the genus *Brevibacillus* as a host is not particularly limited, however, examples thereof include TM medium (peptone: 1%, meat extract: 0.5%, yeast extract: 0.2%, glucose: 1%, pH 7.0) and 2SL medium (peptone: 4%, yeast extract: 0.5%, glucose: 2%, pH 7.2).

Further, in order to suppress degradation or decrease in the molecular weight of the target protein by a protease derived from the host present inside or outside the cells, any of a variety of known protease inhibitors, that is, phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetraacetic acid (EDTA), and/or other commercially available protease inhibitors may be added at an appropriate concentration.

Further, in order to promote the correct folding of the protein of the present invention, for example, a molecular chaperone such as GroEL/ES, Hsp70/DnaK, Hsp90, or Hsp104/ClpB may be used. For example, the molecular chaperone can be coexpressed or can be made to coexist with the protein of the present invention by a method of fusing these into a fusion protein, or the like. In the case where the correct folding of the protein of the present is desired to be achieved, it is also possible to use a method of adding an additive which promotes the correct folding to the culture medium, a method of perform cultivation at a low temperature, or the like, but the method is not limited thereto.

The recombinant protein can be produced by performing aerobic cultivation at a cultivation temperature of 15° C. to 42° C., preferably 20° C. to 37° C. for several hours to several days under aeration and agitation conditions. In some cases, aeration is stopped and anaerobic cultivation may be performed.

The purification of the recombinant protein can be performed by any one or an appropriate combination of affinity chromatography, cation or anion exchange chromatography, gel filtration chromatography, and the like.

The confirmation whether the obtained purified substance is the target protein can be performed by a common method, for example, SDS-polyacrylamide gel electrophoresis, N-terminal amino acid sequence analysis, Western blotting, enzyme-linked immunosorbent assay (ELISA), or the like.

<Affinity Separation Agent>

An affinity separation agent of the present invention can be obtained by immobilizing the protein of the present invention as an affinity ligand on a support composed of a water-insoluble base material. Here, the term "affinity ligand" refers to a substance (functional group) which selectively captures (binds to) a target molecule from an assembly of molecules based on affinity between specific molecules, represented by binding between an antigen and an immunoglobulin, and refers to a protein which specifically binds to an immunoglobulin in this description. Also in the case where it is simply expressed as "ligand", the expression has the same meaning as the "affinity ligand" in this description.

Examples of the support composed of a water-insoluble base material used in the present invention include inorganic supports such as glass beads and silica gel; synthetic polymers such as crosslinked polyvinyl alcohol, crosslinked polyacrylate, crosslinked polyacrylamide and crosslinked polystyrene; organic supports composed of a polysaccharide such as crystalline cellulose, crosslinked cellulose, crosslinked agarose, or crosslinked dextran; and composite supports obtained by combining these supports such as organic-organic composite supports and organic-inorganic composite supports.

Examples of commercial products include GCL2000 (manufactured by Seikagaku Corporation) which is a porous cellulose gel, Sephacryl (registered trademark) S-1000 (manufactured by GE health care. Japan) which is prepared by covalently crosslinking allyl dextran with methylenebisacrylamide, Toyopearl (registered trademark) (manufactured by Tosoh Corporation) which is an acrylate-based support, Sepharose (registered trademark) CL4B (manufactured by GE health care, Japan) which is an agarose-based crosslinked support, and Cellufine (registered trademark) (manufactured by JNC Corporation) which is a cellulose-based crosslinked support. However, the water-insoluble support in the present invention is not limited to only these exemplified supports.

Further, in view of the purpose and method of usage of the affinity separation agent, the water-insoluble support used in the present invention preferably has a large surface area and is preferably a porous material having a large number of fine pores with a suitable size. The support may be in any form such as a bead, a monolith, a fiber, or a film (including a hollow fiber), and any form can be selected appropriately.

With respect to a method for immobilizing the ligand, for example, the ligand may be bound to the support by a conventional coupling method utilizing an amino group, a carboxyl group, a hydroxyl group, a carboamido group, a polyethyleneoxy group, or a thiol group of the ligand.

Examples of the coupling method include a method in which the support is activated by reacting the support with cyanogen bromide, epichlorohydrin, diglycidyl ether, tosyl chloride, tresyl chloride, hydrazine, sodium periodate, or the like (or a reactive functional group is introduced on the support surface), followed by a coupling reaction between the support and a compound to be immobilized as the ligand, whereby immobilization is achieved, and a method in which a condensation reagent such as carbodiimide or a reagent having a plurality of functional groups in the molecule such as glutaraldehyde is added to a system containing the support and a compound to be immobilized as the ligand to effect condensation and crosslinking, whereby immobilization is achieved.

Further, a spacer molecule composed of a plurality of atoms may be introduced between the ligand and the support, or the ligand may be directly immobilized on the support. Therefore, in order to achieve immobilization, the protein of the present invention may be chemically modified, or an amino acid residue useful for immobilization may be added to the protein.

In the case where an amino acid residue useful for immobilization is added, the added amino acid residue is referred to as "tag for immobilization". As the tag for immobilization, an arbitrary number (one or more) of amino acid residues can be added, and as the position where the tag is added, the N-terminal side and/or the C-terminal side of the ligand can be exemplified. Examples of the amino acid useful for immobilization include amino acids having a functional group useful for a chemical reaction for immobilization in a side chain, and for example, lysine (K) which contains an amino group in a side chain, and cysteine (C) which contains a thiol group in a side chain can be exemplified.

On the other hand, as a method for directly immobilizing the ligand to the support, a method in which an amino acid useful for immobilization is substituted or inserted at an arbitrary site of the amino acid sequence of the ligand can be exemplified.

In the nature of the present invention, the effect imparted to the protein in the present invention is also similarly imparted to the separating agent (matrix) formed by immobilizing the protein as the ligand, and even if the protein is modified or altered in any manner for immobilization, the separating agent is included in the scope of the present invention.

Examples of the immobilization form between the ligand and the support in the affinity separation agent of the present invention include multi-point fixing and single-point fixing. The multi-point fixing refers to a form in which immobilization is achieved by chemically binding a ligand main body and/or a tag for immobilization to the support at two or more points, and the "single-point fixing" refers to a form in which immobilization is achieved by chemically binding a ligand main body or a tag for immobilization to the support at one point.

In the case where the ligand is bound to the support and immobilized thereon, two or more domains included in the ligand are distinguished between an immobilized domain and a non-immobilized domain, respectively. Here, the "immobilized domain" refers to a domain which is bound to the support at a plurality of points or a single point, and the "non-immobilized domain" refers to a domain which is not bound to the support.

In the affinity separation agent of the present invention, from the viewpoint that an advantage that the ligand can stably function without being affected by a protease when the separating agent is used in a step of purifying an antibody or the like is significantly exhibited, the ligand includes preferably one or more non-immobilized domains, preferably two or more non-immobilized domains, and in the case of an n-mer ligand, preferably, (n−1) or more domains are non-immobilized domains, and most preferably, all the n domains are non-immobilized domains.

As an immobilized domain-non-immobilized domain pattern in the ligand immobilized on the support, the following four patterns can be exemplified:

(1) a case where all the domains in the ligand are immobilized domains;

(2) a case where one or more domains on the N-terminal side and/or on the C-terminal side in the ligand are immobilized domains;

(3) a case where one or more domains other than the domains at both termini in the ligand are immobilized domains; and (4) a case where a tag for immobilization is introduced at the N terminus and/or the C terminus of the ligand, and immobilized domains are not present.

Hereinafter, an explanation will be given with reference to FIGS. 2 to 5 which are schematic views in the case where a tetramer protein is immobilized on a support as a ligand as examples, however, the same can apply as long as the protein is a dimer or higher-order multimer protein. Incidentally, in FIGS. 2 to 5, four domains included in the tetramer are denoted by a to d, respectively, and the amino acid sequences corresponding to the first and second ligation elements are each shown by a solid line connecting a to d. Incidentally, the amino acid sequences of a to d may be the same as or different from one another, and in both cases where each of a and d is on the C-terminal side or the N-terminal side, the same can apply.

In the case of the above (1), a non-immobilized domain is not formed. For example, this is a case schematically shown in FIG. 2, and since all the domains a to d are bound to the support, even if the ligation element is cleaved due to the effect of a protease when the affinity separation agent is used in a purification step, the ligand can function while being kept bound to the support.

Figure 3A:
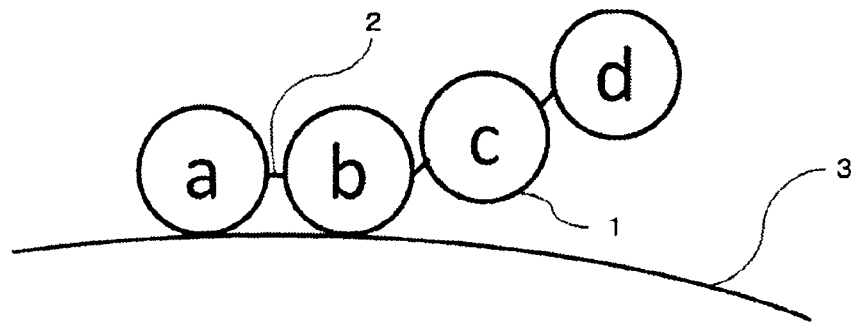
FIGS. 3A to 3C are schematic views in the case where a tetramer protein is immobilized on a support as a ligand, and one or more non-immobilized domains are present.
Figure 3B:
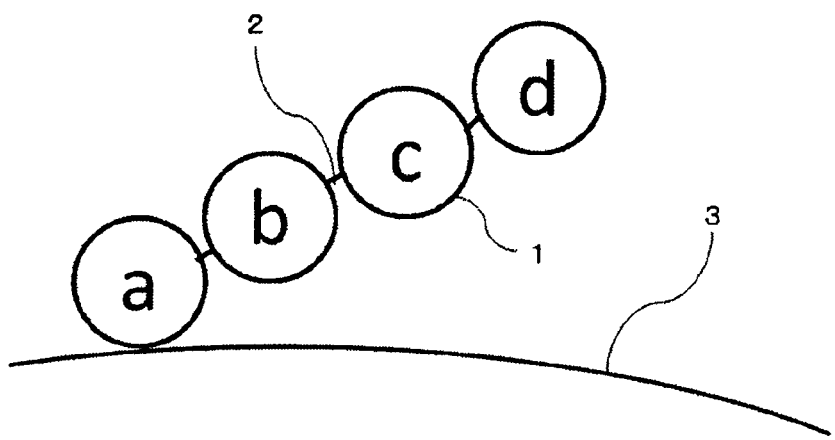
Figure 3C:
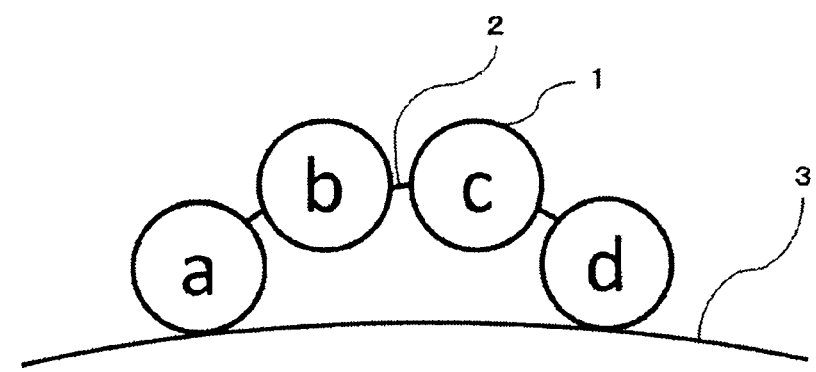

The case of the above (2) is a case where one or more non-immobilized domains are present and is schematically shown in FIGS. 3A to 3C. In FIG. 3A, two domains (a, b) from the N terminus or the C terminus of the ligand are immobilized domains which are bound to the support, and two domains (c, d) at the terminus on the opposite side are non-immobilized domains which are not bound to the support. In this case, the ligand can function even if the ligation element between a and b is cleaved, however, if the ligation element between b and c or between c and d is cleaved, c and d are detached from the support, and thus, do not function as the ligand, and therefore, such a case is not preferred.

In FIG. 3B, the domain (a) at the N terminus or the C terminus of the ligand is an immobilized domain which is bound to the support, and three domains (b, c, d) ligated thereto are non-immobilized domains which are not bound to the support. In this case, even if any ligation element between a and b, between b and c, or between c and d is cleaved, b to d are detached from the support, and thus, do not function as the ligand, and therefore, such a case is not preferred. Above all, if a ligation element between an immobilized domain and a non-immobilized domain like the ligation element between a and b is cleaved, the domains successively bound to the non-immobilized domain do not function, and therefore, such a case is particularly problematic.

In FIG. 3C, the domains (a, d) at the N terminus and the C terminus of the ligand are immobilized domains which are bound to the support, and the two domains (b, c) between them are non-immobilized domains which are not bound to the support. In this case, any two or more ligation elements between a and b, between b and c, or between c and d are cleaved, b and c are detached from the support, and thus, do not function as the ligand, and therefore, such a case is not preferred.

Figure 4A:
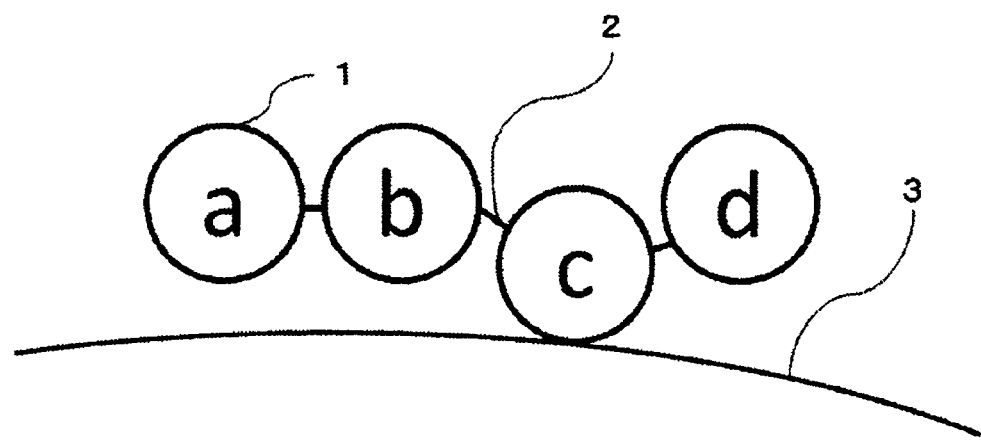
FIGS. 4A and 4B are schematic views in the case where a tetramer protein is immobilized on a support as a ligand, and one or more non-immobilized domains are present.
Figure 4B:
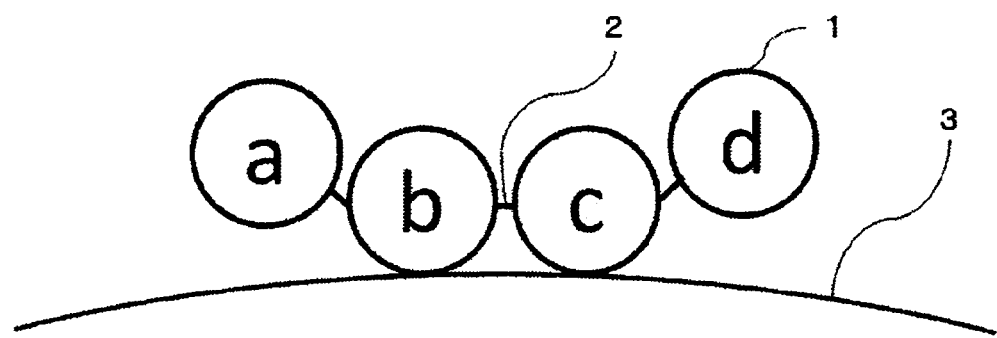

The case of the above (3) is a case where one or more non-immobilized domains are present and is schematically shown in FIGS. 4A and 4B. In FIG. 4A, one domain (c (the same apply to b)) present between the N terminus and the C terminus of the ligand is an immobilized domain which is bound to the support, and two domains (a, d) at both termini and one domain (b (the same apply to c)) ligated thereto are non-immobilized domains which are not bound to the support. In this case, even if any ligation element between a and b, between b and c, or between c and d is cleaved, a, b, and d are detached from the support, and thus, do not function as the ligand, and therefore, such a case is not preferred. Above all, the cleavage of the ligation element between an immobilized domain and a non-immobilized domain like the ligation element between b and c or between c and d is particularly problematic.

In FIG. 4B, two domains (b, c) present between the N terminus and the C terminus of the ligand are immobilized domains which are bound to the support, and two domains (a, d) at both termini are non-immobilized domains which are not bound to the support. In this case, even if the ligation element between b and c is cleaved, b and c can function as the ligand, however, if the ligation element between a and b or between c and d is cleaved, c and d are detached from the support, and thus, do not function as the ligand, and therefore, such a case is not preferred.

Figure 5A:
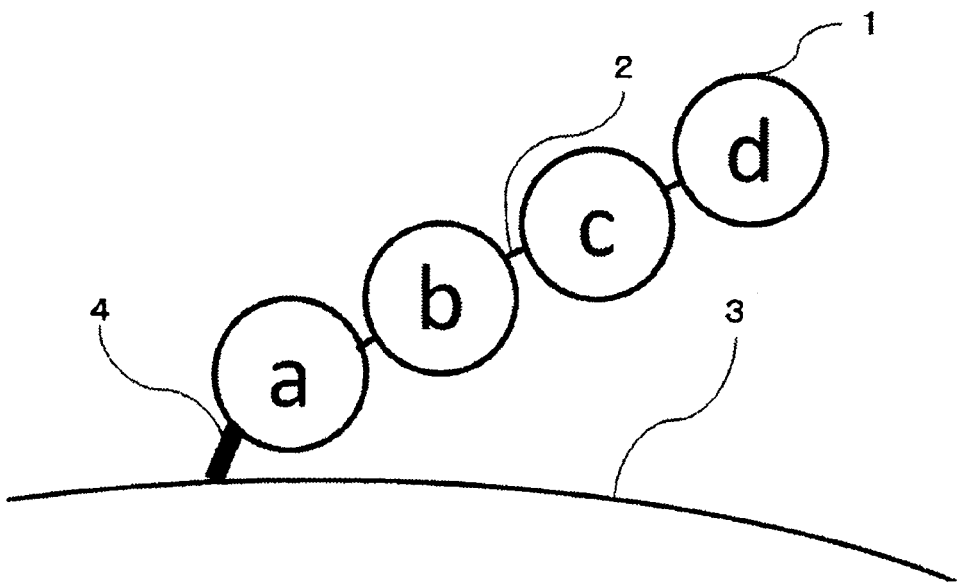
FIGS. 5A and 5B are schematic views in the case where a tetramer protein is immobilized on a support as a ligand, and a linkage to the support is formed by introducing a tag for immobilization and all the domains become non-immobilized domains.
Figure 5B:
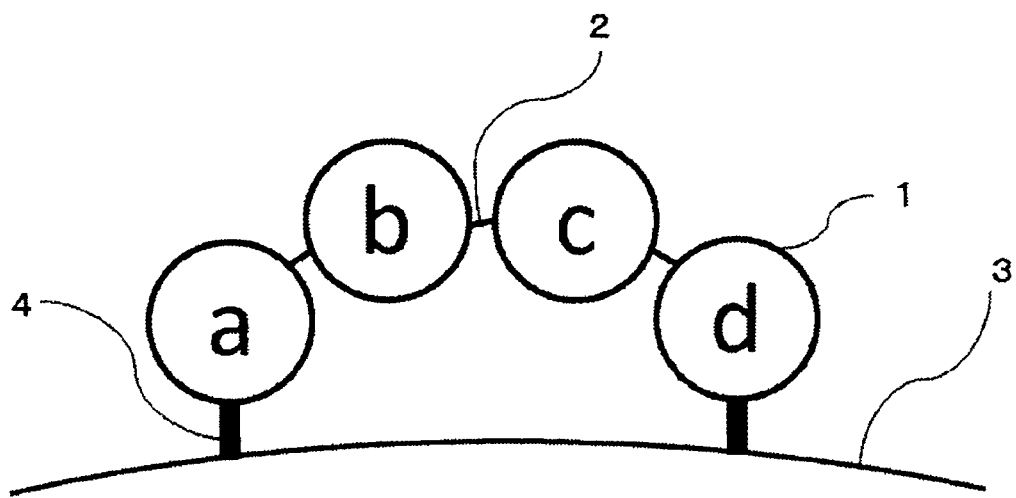

The case of the above (4) is a case where a linkage to the support is formed by introducing a tag for immobilization, and all the domains are non-immobilized domains, and is schematically shown in FIGS. 5A and 5B. In FIG. 5A, a tag for immobilization is introduced into a terminal sequence of the domain (a) at the N terminus or the C terminus of the ligand to effect binding to the support. In this case, even if any ligation element between a and b, between b and c, or between c and d is cleaved, b to d are detached from the support, and thus, do not function as the ligand, and therefore, such a case is not preferred. When the domain a having the tag for immobilization is regarded as an immobilized domain, the cleavage of the ligation element between a and b is particularly problematic in the same manner as described above with reference to FIG. 3B. In addition, if the terminal sequence of a is cleaved by a protease, all the domains are detached from the support, and thus, do not function as the ligand, and therefore, such a case is particularly problematic. Due to this, it is necessary to introduce a mutation for imparting resistance to a protease into a terminal sequence (at the C terminus or the N terminus) which ligates the tag for immobilization of a.

In FIG. 5B, a tag for immobilization is introduced into a terminal sequence of each of the domains (a, d) at the N terminus and the C terminus of the ligand to effect binding to the support. Also in this case, when the domains a and d having the tag for immobilization are regarded as immobilized domains, this case has the same problem as described above with reference to FIG. 3C. In addition, if the terminal sequences of a and d are cleaved by a protease, all the domains are detached from the support, and thus, do not function as the ligand, and therefore, such a case is particularly problematic. Due to this, it is necessary to introduce a mutation for imparting resistance to a protease into the terminal sequences (at the C terminus and the N terminus) which ligate the tag for immobilization of a and d.

Based on the above description, as for the position of the mutated ligation element in the proteins of the first and third aspects in the first embodiment and the second embodiment of the present invention, the element is preferably present between an immobilized domain and a non-immobilized domain or between a non-immobilized domain and a non-immobilized domain. It is more preferred that the element is present at least between an immobilized domain and a non-immobilized domain, and it is further more preferred that, the element is also present between a non-immobilized domain and a non-immobilized domain.

Further, in the case where a tag for immobilization is introduced into the ligand, a domain having the tag for immobilization is regarded as an immobilized domain, and a preferred embodiment may be considered within the above range.

As for the position of a domain in which lysine at position 4 and the C-terminal lysine are deleted or substituted (mutated domain) in the protein of the second aspect of the first embodiment of the present invention, it is preferred that at least the immobilized domain is a mutated domain, and it is more preferred that in addition thereto, the non-immobilized domain which is directly ligated to the immobilized domain is a mutated domain, it is further more preferred that among the successively ligated non-immobilized domains, a non-immobilized domain which is located closer to the immobilized domain is a mutated domain.

On the other hand, it is not particularly problematic when a terminus on the side which is not ligated to another domain is affected by a protease, and therefore, a non-immobilized domain which is farthest from the immobilized domain may not a mutated domain. However, if the non-immobilized domain which is farthest from the immobilized domain is a mutated domain, a ligation site to another domain is not affected by a protease, and therefore, such a case is preferred. Further, in the case where a tag for immobilization is introduced into the ligand, a domain having the tag for immobilization is regarded as an immobilized domain, and a preferred embodiment may be considered within the above range.

The site at which a linkage to the support is formed in the ligand is not particularly limited, but is preferably a terminus of the ligand sequence. By immobilizing the ligand at the terminus, the degree of freedom of the ligand is increased, and by maintaining a region capable of binding to an immunoglobulin wide, an ability to bind to an immunoglobulin can be maintained high. The site may be either of the N terminus and the C terminus as long as it is the terminus of the ligand.

The affinity separation agent of the present invention is preferably capable of binding to a protein including the Fc region of an immunoglobulin. Examples of the protein including the Fc region of an immunoglobulin to which the affinity separation agent binds include an antibody, an antibody derivative, a fragment antibody, and a fragment antibody derivative including the Fc region of an immunoglobulin. These proteins can be separated and purified by an affinity column chromatography purification method.

Incidentally, these proteins are generally produced using Chinese hamster ovary-derived CHO cells, mouse myeloma cells Sp2/O cells, NSO cells, methanol assimilating *Pichia* yeast, baker's yeast, *Aspergillus oryzae*, or the like, however, in the case where a protease is present in the culture solutions thereof, the affinity separation agent of the present invention can minimize the degradation due to the protease, and therefore is preferred.

Here, as the "antibody including the Fc region of an immunoglobulin", for example, IgG can be exemplified. The "antibody derivative" refers to an IgG derivative, and for example, a chimeric antibody in which some of the domains of human IgG are replaced for a domain of an IgG antibody of another species and fused thereto, and a humanized antibody in which a CDR portion of human IgG is replaced for a CDR portion of an antibody of another species and fused thereto can be exemplified.

As the "fragment antibody", for example, a protein composed only of the Fab region of human IgG can be exemplified. As the "fragment antibody derivative", for example, an artificial antibody in which the Fv region and the Fc region of human IgG are fused can be exemplified. Incidentally, as the name collectively referring to these antibody, antibody derivative, fragment antibody, and fragment antibody derivative, the expression of "antibody-like molecule" is used in this description.

By using the affinity separation agent of the present invention, a protein including the Fc region of an immunoglobulin can be separated. Specifically, a column for liquid chromatography including the affinity separation agent of the present invention and provided with at least one container which packs the affinity separation agent in can be formed.

Separation of a protein (the above-mentioned antibody, antibody derivative, fragment antibody, or fragment antibody derivative) including the Fc region can be achieved by the procedure according to an affinity column chromatography purification method using a Protein A column which has already been available as a commercial product (Reference Literature 1: Roque A. C. A. et al., "J. Chromatogr. A", 2007, Vol. 1160, pp. 44-55).

That is, after a buffer solution containing an antibody, an antibody derivative, a fragment antibody, or a fragment antibody derivative is adjusted to a neutral pH, the solution is allowed to pass through the column for liquid chromatography of the present invention, whereby the antibody, the antibody derivative, the fragment antibody, or the fragment antibody derivative is adsorbed thereon. Subsequently, an appropriate amount of a pure buffer solution is allowed to pass through the column for liquid chromatography to wash the inside of the column.

At this time point, the desired antibody, antibody derivative, fragment antibody, or fragment antibody derivative is adsorbed on the affinity separation agent of the present invention in the column. Subsequently, an acidic buffer solution (which may contain a substance that accelerates the dissociation from the matrix) adjusted to an appropriate pH is allowed to pass through the column to elute the desired antibody, antibody derivative, fragment antibody, or fragment antibody derivative, whereby high purity purification can be achieved.

The affinity separation agent of the present invention can be reused by allowing an appropriate strong acidic or strong alkaline pure buffer solution (which may be a solution containing an appropriate denaturing agent or an organic solvent) to such an extent that the function of the ligand compound or the base material of the support is not completely impaired to pass therethrough to effect washing.

In general, each domain constituting Protein A binds to the Fc region more strongly than to the Fab region (Reference Literature 1). Therefore, the "affinity for an immunoglobulin" of the protein of the present invention is essentially an expression showing affinity for the Fc region, and even if only the ability to bind to the Fab region changes, the strength of the affinity for an immunoglobulin does not largely change. In the protein of the present invention, the secondary affinity for the Fab region of the immunoglobulin-binding domain of Protein A is decreased, and therefore, an advantage that the effect of secondary binding on the interaction with immunoglobulin can be eliminated is exhibited.

On the other hand, the affinity for the Fc region is maintained, and therefore, the affinity for the entire immunoglobulin is maintained. As for the affinity for an immunoglobulin of the protein of the present invention, when the affinity for a human immunoglobulin G preparation is measured by the below-mentioned Biacore system, the affinity constant (KA) is preferably $10^6$ ($M^{-1}$) or more, more preferably $10^7$ ($M^{-1}$) or more.

The affinity for an immunoglobulin of the protein of the present invention can be measured by, for example, a biosensor such as Biacore (registered trademark) system (manufactured by GE health care, Japan) using a surface plasmon resonance principle, but the measurement method is not limited thereto.

The measurement conditions may be any conditions as long as a binding signal when Protein A binds to the Fc region of an immunogloulin can be detected, and the affinity can be easily evaluated by performing measurement at a temperature of 20° C. to 40° C. (constant temperature) and a neutral pH condition of 6 to 8.

Example of the target for which the protein of the present invention shows affinity include the Fab region, an immunoglobulin molecule including the Fc region without shortage, and derivatives thereof, however, the target is not limited thereto. The protein of the present invention has affinity also for a protein including a portion on the Fc region side, and the binding target is not necessarily a protein including the full Fc region. The conformation of an antibody has already been known, and therefore, it is possible to further modify (fragment or the like) the Fab region or the Fc region while maintaining the conformation of a region to which the protein of the invention bind by protein engineering, and the protein of the present invention can also bind to derivatives thereof.

Further, the ability to bind to an immunoglobulin of the affinity separation agent in which the protein of the present invention is immobilized can be comparatively evaluated based on, for example, a static adsorption capacity, by which how much the immunoglobulin the separating agent immersed in an excessive amount of immunoglobulin solution can adsorb is evaluated, or a dynamic adsorption capacity, by which the amount of an immunoglobulin solution which breaks through a column packing the separating agent in when the immunoglobulin solution is allowed to pass through the column is evaluated, or the like, however, the method is not limited thereto.

EXAMPLES

Hereinafter, the present invention will be described in further detail with reference to Examples, however, the invention is not limited to these Examples.

Examples of First Embodiment of the Invention

Preparation Example

1) Preparation of Wild-type Protein A Expression Plasmid

A DNA sequence (SEQ ID NO: 7) encoding a wild-type C domain dimer (WT), in which catatg (NdeI) was added on the 5' side and ctcgag (XhoI) was added on the 3' side, was chemically synthesized. The obtained DNA fragment was digested with the restriction enzymes NdeI and XhoI (both manufacture by Thermo Scientific), and the resulting material was purified and collected.

Incidentally, SEQ ID NO: 7 was determined by performing codon optimization for expression in *E. coli* based on the DNA sequence derived from *Staphylococcus aureus*.

As a protein expression vector, a vector pET22b (manufactured by Merck, Inc.) having a T7 promoter, and also having a 6× His tag and a stop codon downstream of the multicloning site was selected. pET22b was digested using the restriction enzymes NdeI and XhoI (both manufacture by Thermo Scientific), and the resulting material was purified and collected.

The DNA fragment of SEQ ID NO: 7 and the pET22b vector treated with the restriction enzymes were ligated using a DNA ligase (LigaFast Rapid DNA Ligation System, manufactured by Promega Corporation), whereby a WT expression vector was constructed.

By using the WT expression vector, *E. coli* JM109 (manufacture by TaKaRa Bio, Inc.) was transformed, and the plasmid DNA was amplified and extracted by a common procedure.

2) Preparation of Protein A Mutant (Mut) Expression Plasmid

An expression vector including each of the DNA sequences (SEQ ID NOS: 34 to 46) encoding Mut 1 to Mut 13, each of which is a protein having a mutation of deletion and/or substitution in part of the amino acid sequence of the wild-type C domain dimer was prepared. The Mut 1 to 13 expression vectors were prepared by the QuikChange method (QuikChange Lightning Site-Directed Mutagenesis Kit, manufactured by Agilent Technologies) using the combination of a template and a synthetic oligonucleotide primer set (SEQ ID NOS: 8 to 33) shown in Table 1. The QuikChange method was performed according to the protocol of Agilent Technologies.

[Table 1]

TABLE 1

| Mutant protein | Template | Sequence of synthetic oligonucleotide | SEQ ID NO |
|---|---|---|---|
| Mut 1 | WT expression vector | GCTGAACGATGCACAAGCTCCGGCAGACAACTTCAACAAGGAACAGCAAAATG<br>CATTTTGCTGTTCCTTGTTGAAGTTGTCTGCCGGAGCTTGTGCATCGTTCAGC | 8<br>9 |
| Mut 2 | WT expression vector | GAACGATGCACAAGCTCCGGACAACAACAAGGAACAGCAAAATG<br>CATTTTGCTGTTCCTTGTTGTTGTCCGGAGCTTGTGCATCGTTC | 10<br>11 |
| Mut 3 | Mut 2 expression vector | GATGCACAAGCTCCGGACCACCACAAGGAACAGCAAAATG<br>CATTTTGCTGTTCCTTGTGGTGGTCCGGAGCTTGTGCATC | 12<br>13 |
| Mut 4 | Mut 6 expression vector | GCTGAACGATGCACAAGCTCCGAATGACAATGATAACGATAACAAGGAACAGCAAAATGCCTTC<br>GAAGGCATTTTGCTGTTCCTTGTTATCGTTATCATTGTCATTCGGAGCTTGTGCATCGTTCAGC | 14<br>15 |
| Mut 5 | Mut 7 expression vector | CAAAAAGCTGAACGATGCACAAGCTCCGAACGGAGACAACGGGGATAACAAGGAACAGCAAAATGCCTTCTATG<br>CATAGAAGGCATTTTGCTGTTCCTTGTTATCCCCGTTGTCTCCGTTCGGAGCTTGTGCATCGTTCAGCTTTTTG | 16<br>17 |
| Mut 6 | Mut 11 expression vector | GCACAAGCTCCGAATGACAACGATAACAAGGAACAGCAAAATG<br>CATTTTGCTGTTCCTTGTTATCGTTGTCATTCGGAGCTTGTGC | 18<br>19 |
| Mut 7 | Mut 11 expression vector | CGATGCACAAGCTCCGGGAGACAACGGGAACAAGGAACAGCAA<br>TTGCTGTTCCTTGTTCCCGTTGTCTCCCGGAGCTTGTGCATCG | 20<br>21 |
| Mut 8 | Mut 4 expression vector | GAACGATGCACAAGCTCCGCATGACCATGATCACGATCACAAGGAACAGCAAAATG<br>CATTTTGCTGTTCCTTGTGATCGTGATCATGGTCATGCGGAGCTTGTGCATCGTTC | 22<br>23 |
| Mut 9 | Mut 11 expression vector | GAACGATGCACAAGCTCCGCATGACCACCACCACAAGGAACAGCAAAATG<br>CATTTTGCTGTTCCTTGTGGTGGTGGTCATGCGGAGCTTGTGCATCGTTC | 24<br>25 |
| Mut 10 | Mut 6 expression vector | GAACGATGCACAAGCTCCGCATGACCACGATCACAAGGAACAGCAAAATG<br>CATTTTGCTGTTCCTTGTGATCGTGGTCATGCGGAGCTTGTGCATCGTTC | 26<br>27 |
| Mut 11 | WT expression vector | GATGCACAAGCTCCGAAAGACAACAAGAACAAGGAACAGCAAAATG<br>CATTTTGCTGTTCCTTGTTCTTGTTGTCTTTCGGAGCTTGTGCATC | 28<br>29 |
| Mut 12 | WT expression vector | GCTGAACGATGCACAAGCTCCGAAAAACAAGGAACAGCAAAATGCCTTCTATG<br>CATAGAAGGCATTTTGCTGTTCCTTGTTTTTCGGAGCTTGTGCATCGTTCAGC | 30<br>31 |
| Mut 13 | WT expression vector | GAACGATGCACAAGCTCCGGACAACAAGAACAAGGAACAGCAAAATG<br>CATTTTGCTGTTCCTTGTTCTTGTTGTCCGGAGCTTGTGCATCGTTC | 32<br>33 |

The obtained Mut 1 to 13 expression vectors were amplified and extracted according to a common procedure by transforming JM109 (manufacture by TaKaRa Bio, Inc.).

The analysis of the DNA sequence of each of the obtained Mut 1 to 13 expression vectors was performed using a DNA sequencer 3130x1 Genetic Analyzer (manufactured by Applied Biosystems). A sequencing PCR reaction for the expression vector was performed using Big Dye Terminator v.1.1 Cycle Sequenceing Kit (manufactured by Applied Biosystems) according to the attached protocol. The thus obtained sequencing PCR product was purified by a common procedure and used in a DNA sequence analysis.

Among the Mut 1 to 13 expression vectors obtained in this Example, DNA sequences encoding a protein to be expressed were as shown by SEQ ID NOS: 34 to 46.

3) Expression of Protein

Rosetta (DE3) (manufactured by Merck, Inc.) was transformed with each of the WT, and Mut 1 to 13 expression vectors obtained in the above 1) and 2), and transformants expressing the target proteins WT, and Mut 1 to 13, respectively, were obtained. The transformation method was performed according to the protocol of Merck, Inc.

The transformant expressing the target protein was inoculated into LB medium containing 50 mg/L carbenicillin, and cultured overnight at 30° C., whereby a preculture solution was obtained. The obtained preculture solution (10 mL) was inoculated into 500 mL of LB medium (containing 50 mg/L carbenicillin), and cultured at 30° C. and 130 rpm until the OD600 reached about 0.6 to 0.8. Isopropyl 1-thio-β-D-galactoside (IPTG) was added thereto so that a final concentration was 0.1 mM, and cultivation was further continued for 4 hours. After completion of the cultivation, the cells were collected by centrifugation.

4) Collection of Protein

The cells collected in the above 3) were suspended in 50 mL of a suspension buffer (50 mM imidazole, pH 8.0, 500 mM NaCl), and subjected to ultrasonic homogenization. The homogenized material was centrifuged and fractionated into a supernatant fraction and a precipitate fraction. The supernatant fraction was applied to a HisTrap HP 5 mL column (manufactured by GE health care, Japan) equilibrated with the suspension buffer, followed by washing with an equilibration buffer, and then, the target protein was eluted using an elution buffer (175 mM imidazole, pH 8.0, 500 mM NaCl). The eluted target protein was dialyzed to replace the buffer with desalted water. The target protein was concentrated to about 30 to 40 mg/mL by centrifugation using Amicon-Ultra 10K (Merck Millipore, Inc.). The target protein after concentration was prepared at 2 mg/mL using a PBS buffer.

After completion of purification, the target protein was subjected to Tricine SDS-PAGE (e-PAGEL R15S, manufactured by ATTO, Inc.), and a single band was confirmed at a molecular weight position of about 14000 Da. The target protein obtained using the WT expression vector was a protein having the amino acid sequence of SEQ ID NO: 47, and the target proteins obtained using the Mut 1 to 13 expression vectors were proteins having the amino acid sequences of SEQ ID NOS: 48 to 60, respectively.

The sequence near the ligation site sequence (first ligation element) of WT and the sequence near the mutated ligation element of each of Mut 1 to 13 are shown in Table 2. In the dimer of the C domain, the amino acid at the position represented by D58 is at the C terminus of the first domain, and the amino acid at the position represented by D1' is at the N terminus of the second domain. Further, the symbol "/ (slash)" indicates that the amino acid is deleted.

TABLE 2

| | Position of amino acid | | | | | | | | | |
|---|---|---|---|---|---|---|---|---|---|---|
| | D56 | D57 | D58 | D1' | D2' | D3' | D4' | D5' | D6' | D7' |
| Mut 1 | A | P | | A | D | N | | F | N | K |
| Mut 2 | A | P | | | D | N | | | N | K |
| Mut 3 | A | P | | | D | H | | | H | K |
| Mut 4 | A | P | N | D | N | D | N | D | N | K |
| Mut 5 | A | P | N | G | D | N | G | D | N | K |
| Mut 6 | A | P | N | | D | N | D | | N | K |
| Mut 7 | A | P | G | | D | N | G | | N | K |
| Mut 8 | A | P | H | D | H | N | H | D | H | K |
| Mut 9 | A | P | H | | D | H | H | | H | K |
| Mut 10 | A | P | H | | D | H | D | | H | K |
| WT | A | P | K | A | D | N | K | F | N | K |
| Mut 11 | A | P | K | | D | N | K | | N | K |
| Mut 12 | A | P | K | | | | | | N | K |
| Mut 13 | A | P | | | D | N | K | | N | K |

Example 1-1

<Evaluation of Resistance to Trypsin>

1) The resistance to trypsin which is a protease was evaluated by the following method.

The Mut 1 protein obtained in Preparation Example and trypsin were mixed and the resulting mixture was heated to 37° C. for 15 minutes. The mixing amounts are as follows.

Protein of Preparation Example 1 (2 mg/mL in a phosphate buffer): 10 μL
Dilution buffer (500 mM Tris-HCl, pH 8.0): 2 μL
Pure water: 6 μL
Trypsin solution (1 mg/mL): 2 μL Subsequently, 20 μL of a diluent for electrophoresis (200 mM Tris-HCl, pH 6.8, 200 mM DTT, 20% glycerol, 4% SDS, 0.012% bromophenol blue: 2× Sample buffer) was added to the obtained mixed solution. A 10 μL portion of the resulting mixture was used as a sample and subjected to electrophoresis using an SDS polyacrylamide gel. As a reference of comparison, the same amount of the mixed solution to which thermolysin was not added was subjected to electrophoresis on the same gel.

After the electrophoresis, the gel was stained, and the occurrence of degradation of the protein was evaluated by comparison based on the staining intensity before and after the trypsin treatment. The "staining intensity" refers to the position and intensity of the stained band obtained by electrophoresis.

As compared with before the trypsin treatment, a case where the protein was hardly degraded (the staining intensity was maintained at 90% or more) was evaluated as "A", a case where the protein was degraded a little (the staining intensity was maintained at 70% or more and less than 90%) was evaluated as "B", a case where the protein was degraded much (the staining intensity was maintained at 30% or more and less than 70%) was evaluated as "C", and a case where most of the protein was degraded (the staining intensity was maintained at less than 30%) was evaluated as "D".

The results are shown in Table 3.

2) The resistance to plasmin which is a protease was evaluated by the following method.

The evaluation was performed in the same manner as the evaluation of the resistance to trypsin except that the trypsin solution (1 mg/mL) was changed to a plasmin solution (10 mg/mL). The results are shown in Table 3.

<Evaluation of Ability to Adsorb Immunoglobulin (SBC)>

The Mut 1 protein (3 mg) obtained in Preparation Example was immobilized on porous acrylic beads (1 mL) activated with an epoxy group to form a separating agent, and an ability to bind to an immunoglobulin was evaluated.

The static adsorption capacity of the separating agent was evaluated according to a common procedure. The results are shown in Table 3.

Examples 1-2 to 1-10, and Comparative Examples 1-1 to 1-4

The evaluation of the resistance to the proteases and the evaluation of the ability to adsorb an immunoglobulin were performed in the same manner as in Example 1-1 except that in place of the Mut 1 protein, Mut 2 to 10 obtained in Preparation Example were used in Examples 1-2 to 1-10, respectively, WT was used in Comparative Example 1-1, and Mut 11 to 13 were used in Comparative Examples 1-2 to 1-4, respectively.

The results are shown in Table 3.

TABLE 3

| Protein | | Resistance to protease | | SBC (mg IgG/mL-R) |
|---|---|---|---|---|
| | | Trypsin | Plasmin | |
| Mut 1 | Example 1-1 | B | B | 25 |
| Mut 2 | Example 1-2 | A | B | 23 |
| Mut 3 | Example 1-3 | A | B | 23 |
| Mut 4 | Example 1-4 | B | B | 24 |
| Mut 5 | Example 1-5 | B | B | 25 |
| Mut 6 | Example 1-6 | B | B | 23 |
| Mut 7 | Example 1-7 | B | B | 25 |
| Mut 8 | Example 1-8 | B | C | 23 |
| Mut 9 | Example 1-9 | B | C | 21 |
| Mut 10 | Example 1-10 | B | C | 22 |
| WT | Comparative Example 1-1 | C | C | 28 |
| Mut 11 | Comparative Example 1-2 | D | D | 25 |
| Mut 12 | Comparative Example 1-3 | D | D | 19 |
| Mut 13 | Comparative Example 1-4 | C | D | 26 |

In Comparative Examples 1-1 to 1-4 in which the C-terminal lysine is not deleted or substituted, both of the resistance to trypsin and the resistance to plasmin are low, however, in Examples 1-1 to 1-10 in which the C-terminal lysine is deleted or substituted, the protein is modified so that at least either of the resistance to trypsin and the resistance to plasmin is enhanced. In Examples 1-2 and 1-3, the ligation site sequence (first ligation element) is composed of two amino acid residues and is short, and the resistance to trypsin is further improved.

Examples of Second Embodiment of the Invention

Preparation Example

1) Preparation of Wild-type Protein A Expression Plasmid

A DNA sequence (SEQ ID NO: 61) encoding a wild-type C domain dimer (WT), in which catatg (NdeI) was added on the 5' side and ctcgag (XhoI) was added on the 3' side, was chemically synthesized. The obtained DNA fragment was digested with the restriction enzymes NdeI and XhoI (both manufacture by Thermo Scientific), and the resulting material was purified and collected.

Incidentally, SEQ ID NO: 61 was determined by performing codon optimization for expression in *E. coli* based on the DNA sequence derived from *Staphylococcus aureus*.

As a protein expression vector, a vector pET22b (manufactured by Merck, Inc.) having a T7 promoter, and also having a 6× His tag and a stop codon downstream of the multicloning site was selected. pET22b was digested using the restriction enzymes NdeI and XhoI (both manufacture by Thermo Scientific), and the resulting material was purified and collected.

The DNA fragment of SEQ ID NO: 61 and the pET22b vector treated with the restriction enzymes were ligated using a DNA ligase (LigaFast Rapid DNA Ligation System, manufactured by Promega Corporation), whereby a WT expression vector was constructed.

By using the WT expression vector, *E. coli* JM109 (manufacture by TaKaRa Bio, Inc.) was transformed, and the plasmid DNA was amplified and extracted by a common procedure.

2) Preparation of Protein A Mutant (Mut) Expression Plasmid

An expression vector including each of the DNA sequences (SEQ ID NOS: 90 to 103) encoding Mut 1 to Mut 14, each of which is a protein having a mutation of deletion and/or substitution in part of the amino acid sequence of the wild-type C domain dimer was prepared. The Mut 1 to 14 expression vectors were prepared by the QuikChange method (QuikChange Lightning Site-Directed Mutagenesis Kit, manufactured by Agilent Technologies) using the combination of a template and a synthetic oligonucleotide primer set (SEQ ID NOS: 62 to 89) shown in Table 4. The QuikChange method was performed according to the protocol of Agilent Technologies.

TABLE 4

Table 4

| Mutant protein | Template | Sequence of synthetic oligonucleotide | SEQ ID NO |
|---|---|---|---|
| Mut 1 | WT expression vector | GATGCACAAGCTCCGAAAGACAACAAGAACAAGGAACAGCAAAATG | 62 |
| | | CATTTTGCTGTTCCTTGTTCTTGTTGTCTTTCGGAGCTTGTGCATC | 63 |
| Mut 2 | WT expression vector | GAACGATGCACAAGCTCCGGACAACAAGAACAAGGAACAGCAAAATG | 64 |
| | | CATTTTGCTGTTCCTTGTTCTTGTTGTCCGGAGCTTGTGCATTCGTTC | 65 |
| Mut 3 | WT expression vector | GAACGATGCACAAGCTCCGGACAACAACAAGGAACAGCAAAATG | 66 |
| | | CATTTTGCTGTTCCTTGTTGTTGTCCGGAGCTTGTGCATCGTTC | 67 |
| Mut 4 | Mut 3 expression vector | GATGCACAAGCTCCGGACCACCACAAGGAACAGCAAAATG | 68 |
| | | CATTTTGCTGTTCCTTGTGGTGGTCCGGAGCTTGTGCATC | 69 |
| Mut 5 | Mut 1 expression vector | GCACAAGCTCCGAATGACAACGATAACAAGGAACAGCAAAATG | 70 |
| | | CATTTTGCTGTTCCTTGTTATCGTTGTCATTCGGAGCTTGTGC | 71 |

TABLE 4-continued

Table 4

| Mutant protein | Template | Sequence of synthetic oligonucleotide | SEQ ID NO |
|---|---|---|---|
| Mut 6 | Mut 1 expression vector | CGATGCACAAGCTCCGGGAGACAACGGGAACAAGGAACAGCAA<br>TTGCTGTTCCTTGTTCCCGTTGTCTCCCGGAGCTTGTGCATCG | 72<br>73 |
| Mut 7 | Mut 1 expression vector | GAACGATGCACAAGCTCCGCATGACCACCACCACAAGGAACAGCAAAATG<br>CATTTTGCTGTTCCTTGTGGTGGTGGTCATGCGGAGCTTGTGCATCGTTC | 74<br>75 |
| Mut 8 | Mut 5 expression vector | GAACGATGCACAAGCTCCGCATGACCACGATCACAAGGAACAGCAAAATG<br>CATTTTGCTGTTCCTTGTGATCGTGGTCATGCGGAGCTTGTGCATCGTTC | 76<br>77 |
| Mut 9 | Mut 5 expression vector | GCTGAACGATGCACAAGCTCCGAATGACAATGATAACGATAACAAGGAACAGCAAAATGCCTTC<br>GAAGGCATTTTGCTGTTCCTTGTTATCGTTATCATTGTCATTCGGAGCTTGTGCATCGTTCAGC | 78<br>79 |
| Mut 10 | Mut 6 expression vector | CAAAAAGCTGAACGATGCACAAGCTCCGAACGGAGACAACGGGGATAACAAGGAACAGCAAAATGCCTTCTATG<br>CATAGAAGGCATTTTGCTGTTCCTTGTTATCCCCGTTGTCTCCGTTCGGAGCTTGTGCATCGTTCAGCTTTTTG | 80<br>81 |
| Mut 11 | Mut 9 expression vector | GAACGATGCACAAGCTCCGCATGACCATGATCACGATCACAAGGAACAGCAAAATG<br>CATTTTGCTGTTCCTTGTGATCGTGATCATGGTCATGCGGAGCTTGTGCATCGTTC | 82<br>83 |
| Mut 12 | WT expression vector | GCTGAACGATGCACAAGCTCCGAAAAAGTTCAACAAGGAACAGCAAAATGCC<br>GGCATTTTGCTGTTCCTTGTTGAACTTTTTCGGAGCTTGTGCATCGTTCAGC | 84<br>85 |
| Mut 13 | WT expression vector | GCTGAACGATGCACAAGCTCCGAAATTCAACAAGGAACAGCAAAATGCCTTC<br>GAAGGCATTTTGCTGTTCCTTGTTGAATTTCGGAGCTTGTGCATCGTTCAGC | 86<br>87 |
| Mut 14 | WT expression vector | GCTGAACGATGCACAAGCTCCGAAAAACAAGGAACAGCAAAATGCCTTCTATG<br>CATAGAAGGCATTTTGCTGTTCCTTGTTTTTCGGAGCTTGTGCATCGTTCAGC | 88<br>89 |

The obtained Mut 1 to 14 expression vectors were amplified and extracted according to a common procedure by transforming JM109 (manufacture by TaKaRa Bio, Inc.).

The analysis of the DNA sequence of each of the obtained Mut 1 to 14 expression vectors was performed using a DNA sequencer 3130x1 Genetic Analyzer (manufactured by Applied Biosystems). A sequencing PCR reaction for the expression vector was performed using Big Dye Terminator v.1.1 Cycle Sequenceing Kit (manufactured by Applied Biosystems) according to the attached protocol. The thus obtained sequencing PCR product was purified by a common procedure and used in a DNA sequence analysis.

Among the Mut 1 to 14 expression vectors obtained in this Example, DNA sequences encoding a protein to be expressed were as shown by SEQ ID NOS: 90 to 103.

3) Expression of Protein

Rosetta (DE3) (manufactured by Merck, Inc.) was transformed with each of the WT, and Mut 1 to 14 expression vectors obtained in the above 1) and 2), and transformants expressing the target proteins WT, and Mut 1 to 14, respectively, were obtained. The transformation method was performed according to the protocol of Merck, Inc.

The transformant expressing the target protein was inoculated into LB medium containing 50 mg/L carbenicillin, and cultured overnight at 30° C., whereby a preculture solution was obtained. The obtained preculture solution (10 mL) was inoculated into 500 mL of LB medium (containing 50 mg/L carbenicillin), and cultured at 30° C. and 130 rpm until the OD600 reached about 0.6 to 0.8. Isopropyl 1-thio-β-D-galactoside (IPTG) was added thereto so that the final concentration was 0.1 mM, and cultivation was further continued for 4 hours. After completion of the cultivation, the cells were collected by centrifugation.

4) Collection of Protein

The cells collected in the above 3) were suspended in 50 mL of a suspension buffer (50 mM imidazole, pH 8.0, 500 mM NaCl), and subjected to ultrasonic homogenization. The homogenized material was centrifuged and fractionated into a supernatant fraction and a precipitate fraction. The supernatant fraction was applied to a HisTrap HP 5 mL column (manufactured by GE health care, Japan) equilibrated with the suspension buffer, followed by washing with an equilibration buffer, and then, the target protein was eluted using an elution buffer (175 mM imidazole, pH 8.0, 500 mM NaCl). The eluted target protein was dialyzed to replace the buffer with desalted water. The target protein was concentrated to about 30 to 40 mg/mL by centrifugation using Amicon-Ultra 10K (Merck Millipore, Inc.). The target protein after concentration was prepared at 2 mg/mL using a PBS buffer.

After completion of purification, the target protein was subjected to Tricine SDS-PAGE (e-PAGEL R15S, manufactured by ATTO, Inc.), and a single band was confirmed at a molecular weight position of about 14000 Da. The target protein obtained using the WT expression vector was a protein having the amino acid sequence of SEQ ID NO: 104, and the target proteins obtained using the Mut 1 to 14 expression vectors were proteins having the amino acid sequences of SEQ ID NOS: 105 to 118, respectively.

The sequence near the ligation element (second ligation element) of WT and the sequence near the mutated ligation element (second ligation element) of each of Mut 1 to 14 are shown in Table 5. In the dimer of the C domain, the amino acid at the position represented by D58 is at the C terminus of the first domain, and the amino acid at the position represented by D1' is at the N terminus of the second domain. Further, the symbol "/ (slash)" indicates that the amino acid is deleted.

TABLE 5

| | Position of amino acid | | | | | | | | | |
|---|---|---|---|---|---|---|---|---|---|---|
| | D56 | D57 | D58 | D1' | D2' | D3' | D4' | D5' | D6' | D7' |
| Mut 11 | A | P | K | | D | N | K | | N | K |
| Mut 13 | A | P | | | D | N | K | | N | K |
| Mut 2 | A | P | | | D | N | | | N | K |
| Mut 3 | A | P | | | D | H | | | H | K |
| Mut 6 | A | P | N | | D | N | D | | N | K |
| Mut 7 | A | P | G | | D | N | G | | N | K |
| Mut 9 | A | P | H | | D | H | H | | H | K |
| Mut 10 | A | P | H | | D | H | D | | H | K |
| Mut 4 | A | P | N | D | N | D | N | D | N | K |
| Mut 5 | A | P | N | G | D | N | G | D | N | K |
| Mut 8 | A | P | H | D | H | N | H | D | H | K |
| WT | A | P | K | A | D | N | K | F | N | K |
| Mut 14 | A | P | K | | | | K | F | N | K |
| Mut 15 | A | P | K | | | | | F | N | K |
| Mut 12 | A | P | K | | | | | | N | K |

Example 2-1

<Evaluation of Resistance to Protease>

1) The resistance to thermolysin which is a protease was evaluated by the following method.

The Mut 1 protein obtained in Preparation Example and thermolysin were mixed and the resulting mixture was heated to 37° C. for 15 minutes. The mixing amounts are as follows.

Protein of Preparation Example 1 (2 mg/mL in a phosphate buffer): 10 µL
Dilution buffer (500 mM Tris-HCl, pH 8.0, 5 mM CaCl$_2$): 2 µL
Pure water: 6 µL
Thermolysin solution (1 mg/mL): 2 µL Subsequently, 20 µL of a diluent for electrophoresis (200 mM Tris-HCl, pH 6.8, 200 mM DTT, 20% glycerol, 4% SDS, 0.012% bromophenol blue: 2× Sample buffer) was added to the obtained mixed solution. A 10 µL portion of the resulting mixture was used as a sample and subjected to electrophoresis using an SDS polyacrylamide gel. As a reference of comparison, the same amount of the mixed solution to which thermolysin was not added was subjected to electrophoresis on the same gel.

After the electrophoresis, the gel was stained, and the occurrence of degradation of the protein was evaluated by comparison based on the staining intensity before and after the thermolysin treatment. The "staining intensity" refers to the position and intensity of the stained band obtained by electrophoresis.

As compared with before the thermolysin treatment, a case where the protein was hardly degraded (the staining intensity was maintained at 90% or more) was evaluated as "A", a case where the protein was degraded a little (the staining intensity was maintained at 70% or more and less than 90%) was evaluated as "B", a case where the protein was degraded much (the staining intensity was maintained at 30% or more and less than 70%) was evaluated as "C", and a case where most of the protein was degraded (the staining intensity was maintained at less than 30%) was evaluated as "D".

The results are shown in Table 6.

2) The resistance to trypsin which is a protease was evaluated by the following method.

The evaluation was performed in the same manner as the evaluation of the resistance to thermolysin except that the thermolysin solution (1 mg/mL) was changed to a trypsin solution (1 mg/mL). The results are shown in Table 6.

3) The resistance to plasmin which is a protease was evaluated by the following method.

The evaluation was performed in the same manner as the evaluation of the resistance to thermolysin except that the thermolysin solution (1 mg/mL) was changed to a plasmin solution (10 mg/mL). The results are shown in Table 6.

<Evaluation of Ability to Adsorb Immunoglobulin (SBC)>

The Mut 1 protein (3 mg) obtained in Preparation Example was immobilized on porous acrylic beads (1 mL) activated with an epoxy group to form an affinity separation agent, and an ability to bind to an immunoglobulin was evaluated. The static adsorption capacity of the separating agent was evaluated according to a common procedure.

The results are shown in Table 6.

Examples 2-2 to 2-11, and Comparative Examples 2-1 to 2-4

The evaluation of the resistance to the proteases and the evaluation of the ability to adsorb an immunoglobulin were performed in the same manner as in Example 2-1 except that in place of the Mut 1 protein, Mut 2 to 11 obtained in Preparation Example were used in Examples 2-2 to 2-11, respectively, WT was used in Comparative Example 2-1, and Mut 12 to 14 were used in Comparative Examples 2-2 to 2-4, respectively.

The results are shown in Table 6.

TABLE 6

| Protein | | Resistance to protease | | | SBC (mg IgG/ mL-R) |
|---|---|---|---|---|---|
| | | Thermolysin | Trypsin | Plasmin | |
| Mut 1 | Example 2-1 | B | D | D | 25 |
| Mut 2 | Example 2-2 | B | C | D | 26 |
| Mut 3 | Example 2-3 | B | A | B | 23 |
| Mut 4 | Example 2-4 | B | A | B | 23 |
| Mut 5 | Example 2-5 | B | B | B | 23 |
| Mut 6 | Example 2-6 | B | B | B | 25 |
| Mut 7 | Example 2-7 | B | B | C | 21 |
| Mut 8 | Example 2-8 | B | B | C | 22 |
| Mut 9 | Example 2-9 | B | B | B | 24 |
| Mut 10 | Example 2-10 | B | B | B | 25 |
| Mut 11 | Example 2-11 | B | B | C | 23 |
| WT | Comparative Example 2-1 | C | | | 28 |
| Mut 12 | Comparative Example 2-2 | C | | | 23 |
| Mut 13 | Comparative Example 2-3 | C | | | 23 |
| Mut 14 | Comparative Example 2-4 | B | | | 19 |

In Comparative Example 2-1 in which the ligation element (second ligation element) is not mutated, the resistance to thermolysin is low, however, in Examples 2-2 to 2-11, each of which has the mutated ligation element (mutated second ligation element), the resistance to thermolysin is high, and also the binding ability is maintained high. In Comparative Examples 2-2 and 2-3, although the hydrophobic amino acid at position 1 of the ligation element (second ligation element) has been deleted, it has a hydrophobic amino acid at position 5, and therefore, the resistance to thermolysin is low. In Comparative Example 2-4, the hydrophobic amino acids at positions 1 and 5 of the ligation element (second ligation element) have been deleted, and therefore, the resistance to thermolysin is high, however, the number of amino acids of the ligation element (second ligation element) is smaller than 1, and therefore, the binding ability is decreased.

While the present invention has been described in detail with respect to the specific embodiments, it will be apparent to those skilled in the art that various changes and modifications may be made without departing from the spirit and scope of the invention. This application is based on Japanese Patent Application (No. 2015-021577) filed on Feb. 5, 2015 and Japanese Patent Application (No. 2015-021578) filed on Feb. 5, 2015, and the entire contents of which are incorporated herein by reference.

INDUSTRIAL APPLICABILITY

According to the present invention, a protein which has resistance to a protease, particularly, a serine protease or thermolysin, and has an ability to bind to an immunoglobulin can be provided, and therefore, the protein of the present invention can be used when producing an affinity ligand which has excellent ability to bind to an immunoglobulin or an affinity separation agent which has excellent durability.

REFERENCE SIGNS LIST 1 domain
2 first or second ligation element
3 support surface
4 tag for immobilization

The invention claimed is:

1. A protein having affinity for an immunoglobulin, which is a protein comprising two or more domains derived from any of B, C, and Z domains of Protein A represented by SEQ ID NOS: 4 to 6, wherein the amino acid sequence of at least one domain of the two or more domains comprises one or more lysines, and when the C-terminal lysine of each domain and a sequence at positions 1 to 5 in the amino acid sequence of each domain are defined as a ligation site sequence, among the lysines in the amino acid sequence only the C-terminal lysine and lysine at position 4 in at least one of the ligation site sequences are deleted or substituted.

2. A protein having affinity for an immunoglobulin, which is a protein comprising two or more domains derived from any of B, C, and Z domains of Protein A represented by SEQ ID NOS: 4 to 6, wherein the amino acid sequence of at least one domain of the two or more domains comprises one or more lysines, and among the lysines in the amino acid sequence only the lysine at position 4 is deleted or substituted and the C-terminal lysine is substituted.

3. The protein according to claim 2, wherein the lysine at position 4 is deleted.

4. The protein according to claim 2, wherein at least one lysine of the lysine at position 4 and the C-terminal lysine is substituted with a hydrophilic amino acid.

5. A protein having affinity for an immunoglobulin, which is a protein comprising two or more domains derived from any of B, C, and Z domains of Protein A represented by SEQ ID NOS: 4 to 6, wherein the amino acid sequence of at least one domain of the two or more domains comprises one or more lysines, and among the lysines in the amino acid sequence only the lysine at position 4 is deleted and the C-terminal lysine is deleted or substituted.

6. The protein according to claim 5, wherein the C-terminal lysine is deleted.

7. The protein according to claim 5, wherein the C-terminal lysine is substituted with a hydrophilic amino acid.

* * * * *

```
                       SEQUENCE LISTING

<160> NUMBER OF SEQ ID NOS: 118

<210> SEQ ID NO 1
  <211> LENGTH: 56
  <212> TYPE: PRT
  <213> ORGANISM: Staphylococcus aureus

<400> SEQUENCE: 1

Ala Gln His Asp Glu Ala Gln Gln Asn Ala Phe Tyr Gln Val Leu Asn
  1               5                   10                  15

Met Pro Asn Leu Asn Ala Asp Gln Arg Asn Gly Phe Ile Gln Ser Leu
                  20                  25                  30

Lys Asp Asp Pro Ser Gln Ser Ala Asn Val Leu Gly Glu Ala Gln Lys
              35                  40                  45

Leu Asn Asp Ser Gln Ala Pro Lys
          50                  55

<210> SEQ ID NO 2
  <211> LENGTH: 61
  <212> TYPE: PRT
  <213> ORGANISM: Staphylococcus aureus

<400> SEQUENCE: 2

Ala Asp Ala Gln Gln Asn Asn Phe Asn Lys Asp Gln Gln Ser Ala Phe
  1               5                   10                  15

Tyr Glu Ile Leu Asn Met Pro Asn Leu Asn Glu Ala Gln Arg Asn Gly
                  20                  25                  30

Phe Ile Gln Ser Leu Lys Asp Asp Pro Ser Gln Ser Thr Asn Val Leu
              35                  40                  45

Gly Glu Ala Lys Lys Leu Asn Glu Ser Gln Ala Pro Lys
          50                  55                  60

<210> SEQ ID NO 3
  <211> LENGTH: 58
  <212> TYPE: PRT
  <213> ORGANISM: Staphylococcus aureus

<400> SEQUENCE: 3

Ala Asp Asn Asn Phe Asn Lys Glu Gln Gln Asn Ala Phe Tyr Glu Ile
  1               5                   10                  15

Leu Asn Met Pro Asn Leu Asn Glu Glu Gln Arg Asn Gly Phe Ile Gln
                  20                  25                  30

Ser Leu Lys Asp Asp Pro Ser Gln Ser Ala Asn Leu Leu Ser Glu Ala
              35                  40                  45
```

Lys Lys Leu Asn Glu Ser Gln Ala Pro Lys
        50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 6
<211> LENGTH: 58
<212> TYPE: PRT
<213> ORGANISM: Staphylococcus aureus

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 7
<211> LENGTH: 360
<212> TYPE: DNA
<213> ORGANISM: Staphylococcus aureus

<400> SEQUENCE: 7
catatggcgg acaacaagtt taacaaagaa caacagaacg ccttttacga aatcctgcac    60
ctgccgaacc tgacggaaga acaacgcaac ggtttttattc agagcctgaa agatgacccg   120
agcgtgtcta aggaaatcct ggcggaagcc aaaaagctga cgatgcaca agctccgaaa   180 gcagacaaca agttcaacaa ggaacagcaa aatgccttct atgaaattct gcatctgccg   240

-continued aacctgaccg aagaacagcg taatggcttc attcaaagcc tgaaggacga cccgagtgtt    300
tccaaagaaa ttctggccga agccaaaaag ctgaatgatg cacaggctcc gaaactcgag    360

<210> SEQ ID NO 8
<211> LENGTH: 53
<212> TYPE: DNA
<213> ORGANISM: Artificial Sequence
<220> FEATURE:
<223> OTHER INFORMATION: primer

<400> SEQUENCE: 8
gctgaacgat gcacaagctc cggcagacaa cttcaacaag gaacagcaaa atg          53

<210> SEQ ID NO 9
<211> LENGTH: 53
<212> TYPE: DNA
<213> ORGANISM: Artificial Sequence
<220> FEATURE:
<223> OTHER INFORMATION: primer

<400> SEQUENCE: 9
cattttgctg ttccttgttg aagttgtctg ccggagcttg tgcatcgttc agc          53

<210> SEQ ID NO 10
<211> LENGTH: 44
<212> TYPE: DNA
<213> ORGANISM: Artificial Sequence
<220> FEATURE:
<223> OTHER INFORMATION: primer

<400> SEQUENCE: 10
gaacgatgca caagctccgg acaacaacaa ggaacagcaa aatg                    44

<210> SEQ ID NO 11
<211> LENGTH: 44
<212> TYPE: DNA
<213> ORGANISM: Artificial Sequence
<220> FEATURE:
<223> OTHER INFORMATION: primer

<400> SEQUENCE: 11
cattttgctg ttccttgttg ttgtccggag cttgtgcatc gttc                    44

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
gatgcacaag ctccggacca ccacaaggaa cagcaaaatg                         40

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
cattttgctg ttccttgtgg tggtccggag cttgtgcatc                         40

<210> SEQ ID NO 14

```
<211> LENGTH: 64
<212> TYPE: DNA
<213> ORGANISM: Artificial Sequence
<220> FEATURE:
<223> OTHER INFORMATION: primer

<400> SEQUENCE: 14
gctgaacgat gcacaagctc cgaatgacaa tgataacgat aacaaggaac agcaaaatgc    60
cttc                                                                64

<210> SEQ ID NO 15
<211> LENGTH: 64
<212> TYPE: DNA
<213> ORGANISM: Artificial Sequence
<220> FEATURE:
<223> OTHER INFORMATION: primer

<400> SEQUENCE: 15
gaaggcattt tgctgttcct tgttatcgtt atcattgtca ttcggagctt gtgcatcgtt    60
cagc                                                                64

<210> SEQ ID NO 16
<211> LENGTH: 74
<212> TYPE: DNA
<213> ORGANISM: Artificial Sequence
<220> FEATURE:
<223> OTHER INFORMATION: primer

<400> SEQUENCE: 16
caaaaagctg aacgatgcac aagctccgaa cggagacaac ggggataaca aggaacagca    60
aaatgccttc tatg                                                     74

<210> SEQ ID NO 17
<211> LENGTH: 74
<212> TYPE: DNA
<213> ORGANISM: Artificial Sequence
<220> FEATURE:
<223> OTHER INFORMATION: primer

<400> SEQUENCE: 17
catagaaggc attttgctgt tccttgttat ccccgttgtc tccgttcgga gcttgtgcat    60
cgttcagctt tttg                                                     74

<210> SEQ ID NO 18
<211> LENGTH: 43
<212> TYPE: DNA
<213> ORGANISM: Artificial Sequence
<220> FEATURE:
<223> OTHER INFORMATION: primer

<400> SEQUENCE: 18
gcacaagctc cgaatgacaa cgataacaag gaacagcaaa atg                     43

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
cattttgctg ttccttgtta tcgttgtcat tcggagcttg tgc                     43
```

<210> SEQ ID NO 20
<211> LENGTH: 43
<212> TYPE: DNA
<213> ORGANISM: Artificial Sequence
<220> FEATURE:
<223> OTHER INFORMATION: primer

<400> SEQUENCE: 20
cgatgcacaa gctccgggag acaacgggaa caaggaacag caa    43

<210> SEQ ID NO 21
<211> LENGTH: 43
<212> TYPE: DNA
<213> ORGANISM: Artificial Sequence
<220> FEATURE:
<223> OTHER INFORMATION: primer

<400> SEQUENCE: 21
ttgctgttcc ttgttcccgt tgtctcccgg agcttgtgca tcg    43

<210> SEQ ID NO 22
<211> LENGTH: 56
<212> TYPE: DNA
<213> ORGANISM: Artificial Sequence
<220> FEATURE:
<223> OTHER INFORMATION: primer

<400> SEQUENCE: 22
gaacgatgca caagctccgc atgaccatga tcacgatcac aaggaacagc aaaatg    56

<210> SEQ ID NO 23
<211> LENGTH: 56
<212> TYPE: DNA
<213> ORGANISM: Artificial Sequence
<220> FEATURE:
<223> OTHER INFORMATION: primer

<400> SEQUENCE: 23
cattttgctg ttccttgtga tcgtgatcat ggtcatgcgg agcttgtgca tcgttc    56

<210> SEQ ID NO 24
<211> LENGTH: 50
<212> TYPE: DNA
<213> ORGANISM: Artificial Sequence
<220> FEATURE:
<223> OTHER INFORMATION: primer

<400> SEQUENCE: 24
gaacgatgca caagctccgc atgaccacca ccacaaggaa cagcaaaatg    50

<210> SEQ ID NO 25
<211> LENGTH: 50
<212> TYPE: DNA
<213> ORGANISM: Artificial Sequence
<220> FEATURE:
<223> OTHER INFORMATION: primer

<400> SEQUENCE: 25
cattttgctg ttccttgtgg tggtggtcat gcggagcttg tgcatcgttc    50

<210> SEQ ID NO 26
<211> LENGTH: 50
<212> TYPE: DNA
<213> ORGANISM: Artificial Sequence
<220> FEATURE:
<223> OTHER INFORMATION: primer

<400> SEQUENCE: 26
gaacgatgca caagctccgc atgaccacga tcacaaggaa cagcaaaatg        50

<210> SEQ ID NO 27
<211> LENGTH: 50
<212> TYPE: DNA
<213> ORGANISM: Artificial Sequence
<220> FEATURE:
<223> OTHER INFORMATION: primer

<400> SEQUENCE: 27
cattttgctg ttccttgtga tcgtggtcat gcggagcttg tgcatcgttc        50

<210> SEQ ID NO 28
<211> LENGTH: 46
<212> TYPE: DNA
<213> ORGANISM: Artificial Sequence
<220> FEATURE:
<223> OTHER INFORMATION: primer

<400> SEQUENCE: 28
gatgcacaag ctccgaaaga caacaagaac aaggaacagc aaaatg            46

<210> SEQ ID NO 29
<211> LENGTH: 46
<212> TYPE: DNA
<213> ORGANISM: Artificial Sequence
<220> FEATURE:
<223> OTHER INFORMATION: primer

<400> SEQUENCE: 29
cattttgctg ttccttgttc ttgttgtctt tcggagcttg tgcatc            46

<210> SEQ ID NO 30
<211> LENGTH: 53
<212> TYPE: DNA
<213> ORGANISM: Artificial Sequence
<220> FEATURE:
<223> OTHER INFORMATION: primer

<400> SEQUENCE: 30
gctgaacgat gcacaagctc cgaaaaacaa ggaacagcaa aatgccttct atg    53

<210> SEQ ID NO 31
<211> LENGTH: 53
<212> TYPE: DNA
<213> ORGANISM: Artificial Sequence
<220> FEATURE:
<223> OTHER INFORMATION: primer

<400> SEQUENCE: 31
catagaaggc attttgctgt tccttgtttt tcggagcttg tgcatcgttc agc    53

<210> SEQ ID NO 32
<211> LENGTH: 47
<212> TYPE: DNA
<213> ORGANISM: Artificial Sequence
<220> FEATURE:
<223> OTHER INFORMATION: primer

<400> SEQUENCE: 32
gaacgatgca caagctccgg acaacaagaa caaggaacag caaaatg           47

<210> SEQ ID NO 33
<211> LENGTH: 47

```
<212> TYPE: DNA
<213> ORGANISM: Artificial Sequence
<220> FEATURE:
<223> OTHER INFORMATION: primer

<400> SEQUENCE: 33
cattttgctg ttccttgttc ttgttgtccg gagcttgtgc atcgttc         47

<210> SEQ ID NO 34
<211> LENGTH: 366
<212> TYPE: DNA
<213> ORGANISM: Staphylococcus aureus

<400> SEQUENCE: 34
gcggacaaca agtttaacaa agaacaacag aacgccttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc ggcagacaac   180
ttcaacaagg aacagcaaaa tgccttctat gaaattctgc atctgccgaa cctgaccgaa   240
gaacagcgta atggcttcat tcaaagcctg aaggacgacc cgagtgtttc caaagaaatt   300
ctggccgaag ccaaaaagct gaatgatgca caggctccga actcgagca ccaccaccac    360 caccac                                                              366

<210> SEQ ID NO 35
<211> LENGTH: 360
<212> TYPE: DNA
<213> ORGANISM: Staphylococcus aureus

<400> SEQUENCE: 35
gcggacaaca agtttaacaa agaacaacag aacgccttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc ggacaacaac   180
aaggaacagc aaaatgcctt ctatgaaatt ctgcatctgc cgaacctgac cgaagaacag   240
cgtaatggct tcattcaaag cctgaaggac gacccgagtg tttccaaaga aattctggcc   300
gaagccaaaa agctgaatga tgcacaggct ccgaaactcg agcaccacca ccaccaccac   360

<210> SEQ ID NO 36
<211> LENGTH: 360
<212> TYPE: DNA
<213> ORGANISM: Staphylococcus aureus

<400> SEQUENCE: 36
gcggacaaca agtttaacaa agaacaacag aacgccttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc ggaccaccac   180
aaggaacagc aaaatgcctt ctatgaaatt ctgcatctgc cgaacctgac cgaagaacag   240
cgtaatggct tcattcaaag cctgaaggac gacccgagtg tttccaaaga aattctggcc   300
gaagccaaaa agctgaatga tgcacaggct ccgaaactcg agcaccacca ccaccaccac   360

<210> SEQ ID NO 37
<211> LENGTH: 372
<212> TYPE: DNA
<213> ORGANISM: Staphylococcus aureus

<400> SEQUENCE: 37
```

```
gcggacaaca agtttaacaa agaacaacag aacgcctttt acgaaatcct gcacctgccg      60
aacctgacgg aagaacaacg caacggtttt attcagagcc tgaaagatga cccgagcgtg     120
tctaaggaaa tcctggcgga agccaaaaag ctgaacgatg cacaagctcc gaatgacaat     180
gataacgata acaaggaaca gcaaaatgcc ttctatgaaa ttctgcatct gccgaacctg     240
accgaagaac agcgtaatgg cttcattcaa agcctgaagg acgacccgag tgtttccaaa     300
gaaattctgg ccgaagccaa aaagctgaat gatgcacagg ctccgaaact cgagcaccac     360
caccaccacc ac                                                         372
```

<210> SEQ ID NO 38
<211> LENGTH: 372
<212> TYPE: DNA
<213> ORGANISM: Staphylococcus aureus

<400> SEQUENCE: 38

```
gcggacaaca agtttaacaa agaacaacag aacgcctttt acgaaatcct gcacctgccg      60
aacctgacgg aagaacaacg caacggtttt attcagagcc tgaaagatga cccgagcgtg     120
tctaaggaaa tcctggcgga agccaaaaag ctgaacgatg cacaagctcc gaacggagac     180 aacgggata acaaggaaca gcaaaatgcc ttctatgaaa ttctgcatct gccgaacctg     240
accgaagaac agcgtaatgg cttcattcaa agcctgaagg acgacccgag tgtttccaaa     300
gaaattctgg ccgaagccaa aaagctgaat gatgcacagg ctccgaaact cgagcaccac     360
caccaccacc ac                                                         372
```

<210> SEQ ID NO 39
<211> LENGTH: 366
<212> TYPE: DNA
<213> ORGANISM: Staphylococcus aureus

<400> SEQUENCE: 39

```
gcggacaaca agtttaacaa agaacaacag aacgcctttt acgaaatcct gcacctgccg      60
aacctgacgg aagaacaacg caacggtttt attcagagcc tgaaagatga cccgagcgtg     120
tctaaggaaa tcctggcgga agccaaaaag ctgaacgatg cacaagctcc gaatgacaac     180
gataacaagg aacagcaaaa tgccttctat gaaattctgc atctgccgaa cctgaccgaa     240
gaacagcgta atggcttcat tcaaagcctg aaggacgacc cgagtgtttc caaagaaatt     300
ctggccgaag ccaaaaagct gaatgatgca caggctccga aactcgagca ccaccaccac     360
caccac                                                                 366
```

<210> SEQ ID NO 40
<211> LENGTH: 366
<212> TYPE: DNA
<213> ORGANISM: Staphylococcus aureus

<400> SEQUENCE: 40

```
gcggacaaca agtttaacaa agaacaacag aacgcctttt acgaaatcct gcacctgccg      60
aacctgacgg aagaacaacg caacggtttt attcagagcc tgaaagatga cccgagcgtg     120
tctaaggaaa tcctggcgga agccaaaaag ctgaacgatg cacaagctcc gggagacaac     180
gggaacaagg aacagcaaaa tgccttctat gaaattctgc atctgccgaa cctgaccgaa     240
gaacagcgta atggcttcat tcaaagcctg aaggacgacc cgagtgtttc caaagaaatt     300
ctggccgaag ccaaaaagct gaatgatgca caggctccga aactcgagca ccaccaccac     360
caccac                                                                 366
```

```
<210> SEQ ID NO 41
<211> LENGTH: 372
<212> TYPE: DNA
<213> ORGANISM: Staphylococcus aureus

<400> SEQUENCE: 41
gcggacaaca agtttaacaa agaacaacag aacgcctttt acgaaatcct gcacctgccg     60
aacctgacgg aagaacaacg caacggtttt attcagagcc tgaaagatga cccgagcgtg    120
tctaaggaaa tcctggcgga agccaaaaag ctgaacgatg cacaagctcc gcatgaccat    180
gatcacgatc acaaggaaca gcaaaatgcc ttctatgaaa ttctgcatct gccgaacctg    240
accgaagaac agcgtaatgg cttcattcaa agcctgaagg acgacccgag tgtttccaaa    300
gaaattctgg ccgaagccaa aaagctgaat gatgcacagg ctccgaaact cgagcaccac    360
caccaccacc ac                                                        372

<210> SEQ ID NO 42
<211> LENGTH: 366
<212> TYPE: DNA
<213> ORGANISM: Staphylococcus aureus

<400> SEQUENCE: 42
gcggacaaca agtttaacaa agaacaacag aacgcctttt acgaaatcct gcacctgccg     60
aacctgacgg aagaacaacg caacggtttt attcagagcc tgaaagatga cccgagcgtg    120
tctaaggaaa tcctggcgga agccaaaaag ctgaacgatg cacaagctcc gcatgaccac    180
caccacaagg aacagcaaaa tgccttctat gaaattctgc atctgccgaa cctgaccgaa    240
gaacagcgta atggcttcat tcaaagcctg aaggacgacc cgagtgtttc caaagaaatt    300
ctggccgaag ccaaaaagct gaatgatgca caggctccga aactcgagca ccaccaccac    360
caccac                                                               366

<210> SEQ ID NO 43
<211> LENGTH: 366
<212> TYPE: DNA
<213> ORGANISM: Staphylococcus aureus

<400> SEQUENCE: 43
gcggacaaca agtttaacaa agaacaacag aacgcctttt acgaaatcct gcacctgccg     60
aacctgacgg aagaacaacg caacggtttt attcagagcc tgaaagatga cccgagcgtg    120
tctaaggaaa tcctggcgga agccaaaaag ctgaacgatg cacaagctcc gcatgaccac    180
gatcacaagg aacagcaaaa tgccttctat gaaattctgc atctgccgaa cctgaccgaa    240
gaacagcgta atggcttcat tcaaagcctg aaggacgacc cgagtgtttc caaagaaatt    300
ctggccgaag ccaaaaagct gaatgatgca caggctccga aactcgagca ccaccaccac    360
caccac                                                               366

<210> SEQ ID NO 44
<211> LENGTH: 366
<212> TYPE: DNA
<213> ORGANISM: Staphylococcus aureus

<400> SEQUENCE: 44
gcggacaaca agtttaacaa agaacaacag aacgcctttt acgaaatcct gcacctgccg     60
aacctgacgg aagaacaacg caacggtttt attcagagcc tgaaagatga cccgagcgtg    120
```

```
tctaaggaaa tcctggcgga agccaaaaag ctgaacgatg cacaagctcc gaaagacaac      180
aagaacaagg aacagcaaaa tgccttctat gaaattctgc atctgccgaa cctgaccgaa      240
gaacagcgta atggcttcat tcaaagcctg aaggacgacc cgagtgtttc aaagaaatt       300 ctggccgaag ccaaaaagct gaatgatgca caggctccga actcgagca ccaccaccac       360 caccac                                                                 366

<210> SEQ ID NO 45
<211> LENGTH: 357
<212> TYPE: DNA
<213> ORGANISM: Staphylococcus aureus

<400> SEQUENCE: 45
gcggacaaca gtttaacaa agaacaacag aacgcctttt acgaaatcct gcacctgccg       60
aacctgacgg aagaacaacg caacggtttt attcagagcc tgaaagatga cccgagcgtg      120
tctaaggaaa tcctggcgga agccaaaaag ctgaacgatg cacaagctcc gaaaaacaag      180
gaacagcaaa atgccttcta tgaaattctg catctgccga acctgaccga agaacagcgt      240
aatggcttca ttcaaagcct gaaggacgac ccgagtgttt ccaaagaaat tctggccgaa      300
gccaaaaagc tgaatgatgc acaggctccg aaactcgagc accaccacca ccaccac        357

<210> SEQ ID NO 46
<211> LENGTH: 363
<212> TYPE: DNA
<213> ORGANISM: Staphylococcus aureus

<400> SEQUENCE: 46
gcggacaaca gtttaacaa agaacaacag aacgcctttt acgaaatcct gcacctgccg       60
aacctgacgg aagaacaacg caacggtttt attcagagcc tgaaagatga cccgagcgtg      120
tctaaggaaa tcctggcgga agccaaaaag ctgaacgatg cacaagctcc ggacaacaag      180
aacaaggaac agcaaaatgc cttctatgaa attctgcatc tgccgaacct gaccgaagaa      240
cagcgtaatg gcttcattca aagcctgaag gacgacccga gtgtttccaa agaaattctg      300
gccgaagcca aaaagctgaa tgatgcacag gctccgaaac tcgagcacca ccaccaccac      360
cac                                                                    363

<210> SEQ ID NO 47
<211> LENGTH: 124
<212> TYPE: PRT
<213> ORGANISM: Staphylococcus aureus

<400> SEQUENCE: 47

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Gly Phe Ile Gln Ser Leu Lys Asp Asp Pro
            85                  90                  95

Ser Val Ser Lys Glu Ile Leu Ala Glu Ala Lys Lys Leu Asn Asp Ala
```

```
                   100                 105                 110
Gln Ala Pro Lys Leu Glu His His His His His His
            115                 120

<210> SEQ ID NO 48
<211> LENGTH: 122
<212> TYPE: PRT
<213> ORGANISM: Staphylococcus aureus

<400> SEQUENCE: 48

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Ala Asp Asn Phe Asn Lys Glu
    50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 49
<211> LENGTH: 120
<212> TYPE: PRT
<213> ORGANISM: Staphylococcus aureus

<400> SEQUENCE: 49

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp Asn Lys Glu Gln Gln
    50                  55                  60

Asn Ala Phe Tyr Glu Ile Leu His Leu Pro Asn Leu Thr Glu Glu Gln
65                  70                  75                  80

Arg Asn Gly Phe Ile Gln Ser Leu Lys Asp Asp Pro Ser Val Ser Lys
                85                  90                  95

Glu Ile Leu Ala Glu Ala Lys Lys Leu Asn Asp Ala Gln Ala Pro Lys
            100                 105                 110

Leu Glu His His His His His His
        115                 120

<210> SEQ ID NO 50
<211> LENGTH: 120
<212> TYPE: PRT
<213> ORGANISM: Staphylococcus aureus

<400> SEQUENCE: 50

Ala Asp Asn Lys Phe Asn Lys Glu Gln Gln Asn Ala Phe Tyr Glu Ile
1               5                   10                  15
```

```
Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp His His Lys Glu Gln Gln
 50                  55                  60

Asn Ala Phe Tyr Glu Ile Leu His Leu Pro Asn Leu Thr Glu Glu Gln
 65                  70                  75                  80

Arg Asn Gly Phe Ile Gln Ser Leu Lys Asp Asp Pro Ser Val Ser Lys
                85                  90                  95

Glu Ile Leu Ala Glu Ala Lys Lys Leu Asn Asp Ala Gln Ala Pro Lys
            100                 105                 110

Leu Glu His His His His His His
        115                 120

<210> SEQ ID NO 51
<211> LENGTH: 124
<212> TYPE: PRT
<213> ORGANISM: Staphylococcus aureus

<400> SEQUENCE: 51

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asn Asp Asn Asp Asn
 50                  55                  60

Lys Glu Gln Gln Asn Ala Phe Tyr Glu Ile Leu His Leu Pro Asn Leu
 65                  70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Leu Glu His His His His His His
        115                 120

<210> SEQ ID NO 52
<211> LENGTH: 124
<212> TYPE: PRT
<213> ORGANISM: Staphylococcus aureus

<400> SEQUENCE: 52

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asn Gly Asp Asn Gly Asp Asn
 50                  55                  60

Lys Glu Gln Gln Asn Ala Phe Tyr Glu Ile Leu His Leu Pro Asn Leu
 65                  70                  75                  80

Thr Glu Glu Gln Arg Asn Gly Phe Ile Gln Ser Leu Lys Asp Asp Pro
                85                  90                  95
```

```
Ser Val Ser Lys Glu Ile Leu Ala Glu Ala Lys Lys Leu Asn Asp Ala
            100                 105                 110

Gln Ala Pro Lys Leu Glu His His His His His His
        115                 120
```

<210> SEQ ID NO 53
<211> LENGTH: 122
<212> TYPE: PRT
<213> ORGANISM: Staphylococcus aureus

<400> SEQUENCE: 53

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asn Asp Asn Asp Asn Lys Glu
    50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120
```

<210> SEQ ID NO 54
<211> LENGTH: 122
<212> TYPE: PRT
<213> ORGANISM: Staphylococcus aureus

<400> SEQUENCE: 54

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Gly Asp Asn Gly Asn Lys Glu
    50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120
```

<210> SEQ ID NO 55
<211> LENGTH: 124
<212> TYPE: PRT
<213> ORGANISM: Staphylococcus aureus

<400> SEQUENCE: 55

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro His Asp His Asp His Asp His
50                  55                  60

Lys Glu Gln Gln Asn Ala Phe Tyr Glu Ile Leu His Leu Pro Asn Leu
65                  70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Leu Glu His His His His His
            115                 120

<210> SEQ ID NO 56
<211> LENGTH: 122
<212> TYPE: PRT
<213> ORGANISM: Staphylococcus aureus

<400> SEQUENCE: 56

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro His Asp His His His Lys Glu
50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
            115                 120

<210> SEQ ID NO 57
<211> LENGTH: 122
<212> TYPE: PRT
<213> ORGANISM: Staphylococcus aureus

<400> SEQUENCE: 57

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro His Asp His Asp His Lys Glu
            50                  55                  60

Gln Gln Asn Ala Phe Tyr Glu Ile Leu His Leu Pro Asn Leu Thr Glu
65                  70                  75                  80
```

```
Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 58
<211> LENGTH: 122
<212> TYPE: PRT
<213> ORGANISM: Staphylococcus aureus

<400> SEQUENCE: 58

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Asp Asn Lys Asn Lys Glu
        50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 59
<211> LENGTH: 119
<212> TYPE: PRT
<213> ORGANISM: Staphylococcus aureus

<400> SEQUENCE: 59

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Asn Lys Glu Gln Gln Asn
        50                  55                  60

Ala Phe Tyr Glu Ile Leu His Leu Pro Asn Leu Thr Glu Glu Gln Arg
65                  70                  75                  80

Asn Gly Phe Ile Gln Ser Leu Lys Asp Asp Pro Ser Val Ser Lys Glu
                85                  90                  95

Ile Leu Ala Glu Ala Lys Lys Leu Asn Asp Ala Gln Ala Pro Lys Leu
            100                 105                 110

Glu His His His His His His
        115

<210> SEQ ID NO 60
<211> LENGTH: 121
<212> TYPE: PRT
<213> ORGANISM: Staphylococcus aureus
```

<400> SEQUENCE: 60

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp Asn Lys Asn Lys Glu Gln
    50                  55                  60

Gln Asn Ala Phe Tyr Glu Ile Leu His Leu Pro Asn Leu Thr Glu Glu
65                  70                  75                  80

Gln Arg Asn Gly Phe Ile Gln Ser Leu Lys Asp Asp Pro Ser Val Ser
                85                  90                  95

Lys Glu Ile Leu Ala Glu Ala Lys Lys Leu Asn Asp Ala Gln Ala Pro
            100                 105                 110

Lys Leu Glu His His His His His His
        115                 120

<210> SEQ ID NO 61
<211> LENGTH: 360
<212> TYPE: DNA
<213> ORGANISM: Staphylococcus aureus

<400> SEQUENCE: 61
catatggcgg acaacaagtt taacaaagaa caacagaacg ccttttacga aatcctgcac      60
ctgccgaacc tgacggaaga acaacgcaac ggtttttattc agagcctgaa agatgacccg    120
agcgtgtcta aggaaatcct ggcggaagcc aaaaagctga acgatgcaca agctccgaaa    180
gcagacaaca agttcaacaa ggaacagcaa aatgccttct atgaaattct gcatctgccg    240
aacctgaccg aagaacagcg taatggcttc attcaaagcc tgaaggacga cccgagtgtt    300
tccaaagaaa ttctggccga agccaaaaag ctgaatgatg cacaggctcc gaaactcgag    360

<210> SEQ ID NO 62
<211> LENGTH: 46
<212> TYPE: DNA
<213> ORGANISM: Artificial Sequence
<220> FEATURE:
<223> OTHER INFORMATION: primer

<400> SEQUENCE: 62
gatgcacaag ctccgaaaga caacaagaac aaggaacagc aaaatg                    46

<210> SEQ ID NO 63
<211> LENGTH: 46
<212> TYPE: DNA
<213> ORGANISM: Artificial Sequence
<220> FEATURE:
<223> OTHER INFORMATION: primer

<400> SEQUENCE: 63
cattttgctg ttccttgttc ttgttgtctt tcggagcttg tgcatc                    46

<210> SEQ ID NO 64
<211> LENGTH: 47
<212> TYPE: DNA
<213> ORGANISM: Artificial Sequence
<220> FEATURE:
<223> OTHER INFORMATION: primer

<400> SEQUENCE: 64
gaacgatgca caagctccgg acaacaagaa caaggaacag caaaatg         47

<210> SEQ ID NO 65
<211> LENGTH: 47
<212> TYPE: DNA
<213> ORGANISM: Artificial Sequence
<220> FEATURE:
<223> OTHER INFORMATION: primer

<400> SEQUENCE: 65
cattttgctg ttccttgttc ttgttgtccg gagcttgtgc atcgttc         47

<210> SEQ ID NO 66
<211> LENGTH: 44
<212> TYPE: DNA
<213> ORGANISM: Artificial Sequence
<220> FEATURE:
<223> OTHER INFORMATION: primer

<400> SEQUENCE: 66
gaacgatgca caagctccgg acaacaacaa ggaacagcaa aatg            44

<210> SEQ ID NO 67
<211> LENGTH: 44
<212> TYPE: DNA
<213> ORGANISM: Artificial Sequence
<220> FEATURE:
<223> OTHER INFORMATION: primer

<400> SEQUENCE: 67
cattttgctg ttccttgttg ttgtccggag cttgtgcatc gttc            44

<210> SEQ ID NO 68
<211> LENGTH: 40
<212> TYPE: DNA
<213> ORGANISM: Artificial Sequence
<220> FEATURE:
<223> OTHER INFORMATION: primer

<400> SEQUENCE: 68
gatgcacaag ctccggacca ccacaaggaa cagcaaaatg                 40

<210> SEQ ID NO 69
<211> LENGTH: 40
<212> TYPE: DNA
<213> ORGANISM: Artificial Sequence
<220> FEATURE:
<223> OTHER INFORMATION: primer

<400> SEQUENCE: 69
cattttgctg ttccttgtgg tggtccggag cttgtgcatc                 40

<210> SEQ ID NO 70
<211> LENGTH: 43
<212> TYPE: DNA
<213> ORGANISM: Artificial Sequence
<220> FEATURE:
<223> OTHER INFORMATION: primer

<400> SEQUENCE: 70
gcacaagctc cgaatgacaa cgataacaag gaacagcaaa atg             43

<210> SEQ ID NO 71
<211> LENGTH: 43
<212> TYPE: DNA

```
<213> ORGANISM: Artificial Sequence
<220> FEATURE:
<223> OTHER INFORMATION: primer

<400> SEQUENCE: 71
cattttgctg ttccttgtta tcgttgtcat tcggagcttg tgc                43

<210> SEQ ID NO 72
<211> LENGTH: 43
<212> TYPE: DNA
<213> ORGANISM: Artificial Sequence
<220> FEATURE:
<223> OTHER INFORMATION: primer

<400> SEQUENCE: 72
cgatgcacaa gctccgggag acaacgggaa caaggaacag caa                43

<210> SEQ ID NO 73
<211> LENGTH: 43
<212> TYPE: DNA
<213> ORGANISM: Artificial Sequence
<220> FEATURE:
<223> OTHER INFORMATION: primer

<400> SEQUENCE: 73
ttgctgttcc ttgttcccgt tgtctcccgg agcttgtgca tcg                43

<210> SEQ ID NO 74
<211> LENGTH: 50
<212> TYPE: DNA
<213> ORGANISM: Artificial Sequence
<220> FEATURE:
<223> OTHER INFORMATION: primer

<400> SEQUENCE: 74
gaacgatgca caagctccgc atgaccacca ccacaaggaa cagcaaaatg           50

<210> SEQ ID NO 75
<211> LENGTH: 50
<212> TYPE: DNA
<213> ORGANISM: Artificial Sequence
<220> FEATURE:
<223> OTHER INFORMATION: primer

<400> SEQUENCE: 75
cattttgctg ttccttgtgg tggtggtcat gcggagcttg tgcatcgttc           50

<210> SEQ ID NO 76
<211> LENGTH: 50
<212> TYPE: DNA
<213> ORGANISM: Artificial Sequence
<220> FEATURE:
<223> OTHER INFORMATION: primer

<400> SEQUENCE: 76
gaacgatgca caagctccgc atgaccacga tcacaaggaa cagcaaaatg           50

<210> SEQ ID NO 77
<211> LENGTH: 50
<212> TYPE: DNA
<213> ORGANISM: Artificial Sequence
<220> FEATURE:
<223> OTHER INFORMATION: primer

<400> SEQUENCE: 77
cattttgctg ttccttgtga tcgtggtcat gcggagcttg tgcatcgttc           50
```

<210> SEQ ID NO 78
<211> LENGTH: 64
<212> TYPE: DNA
<213> ORGANISM: Artificial Sequence
<220> FEATURE:
<223> OTHER INFORMATION: primer

<400> SEQUENCE: 78
gctgaacgat gcacaagctc cgaatgacaa tgataacgat aacaaggaac agcaaaatgc    60
cttc                                                                64

<210> SEQ ID NO 79
<211> LENGTH: 64
<212> TYPE: DNA
<213> ORGANISM: Artificial Sequence
<220> FEATURE:
<223> OTHER INFORMATION: primer

<400> SEQUENCE: 79
gaaggcattt tgctgttcct tgttatcgtt atcattgtca ttcggagctt gtgcatcgtt    60
cagc                                                                64

<210> SEQ ID NO 80
<211> LENGTH: 74
<212> TYPE: DNA
<213> ORGANISM: Artificial Sequence
<220> FEATURE:
<223> OTHER INFORMATION: primer

<400> SEQUENCE: 80
caaaaagctg aacgatgcac aagctccgaa cggagacaac ggggataaca aggaacagca    60
aaatgccttc tatg                                                     74

<210> SEQ ID NO 81
<211> LENGTH: 74
<212> TYPE: DNA
<213> ORGANISM: Artificial Sequence
<220> FEATURE:
<223> OTHER INFORMATION: primer

<400> SEQUENCE: 81
catagaaggc attttgctgt tccttgttat ccccgttgtc tccgttcgga gcttgtgcat    60
cgttcagctt tttg                                                     74

<210> SEQ ID NO 82
<211> LENGTH: 56
<212> TYPE: DNA
<213> ORGANISM: Artificial Sequence
<220> FEATURE:
<223> OTHER INFORMATION: primer

<400> SEQUENCE: 82
gaacgatgca caagctccgc atgaccatga tcacgatcac aaggaacagc aaaatg        56

<210> SEQ ID NO 83
<211> LENGTH: 56
<212> TYPE: DNA
<213> ORGANISM: Artificial Sequence
<220> FEATURE:
<223> OTHER INFORMATION: primer

<400> SEQUENCE: 83
cattttgctg ttccttgtga tcgtgatcat ggtcatgcgg agcttgtgca tcgttc        56

<210> SEQ ID NO 84
<211> LENGTH: 52
<212> TYPE: DNA
<213> ORGANISM: Artificial Sequence
<220> FEATURE:
<223> OTHER INFORMATION: primer

<400> SEQUENCE: 84
gctgaacgat gcacaagctc cgaaaaagtt caacaaggaa cagcaaaatg cc        52

<210> SEQ ID NO 85
<211> LENGTH: 52
<212> TYPE: DNA
<213> ORGANISM: Artificial Sequence
<220> FEATURE:
<223> OTHER INFORMATION: primer

<400> SEQUENCE: 85
ggcattttgc tgttccttgt tgaacttttt cggagcttgt gcatcgttca gc        52

<210> SEQ ID NO 86
<211> LENGTH: 52
<212> TYPE: DNA
<213> ORGANISM: Artificial Sequence
<220> FEATURE:
<223> OTHER INFORMATION: primer

<400> SEQUENCE: 86
gctgaacgat gcacaagctc cgaaattcaa caaggaacag caaaatgcct tc        52

<210> SEQ ID NO 87
<211> LENGTH: 52
<212> TYPE: DNA
<213> ORGANISM: Artificial Sequence
<220> FEATURE:
<223> OTHER INFORMATION: primer

<400> SEQUENCE: 87
gaaggcattt tgctgttcct tgttgaattt cggagcttgt gcatcgttca gc        52

<210> SEQ ID NO 88
<211> LENGTH: 53
<212> TYPE: DNA
<213> ORGANISM: Artificial Sequence
<220> FEATURE:
<223> OTHER INFORMATION: primer

<400> SEQUENCE: 88
gctgaacgat gcacaagctc cgaaaaacaa ggaacagcaa aatgccttct atg        53

<210> SEQ ID NO 89
<211> LENGTH: 53
<212> TYPE: DNA
<213> ORGANISM: Artificial Sequence
<220> FEATURE:
<223> OTHER INFORMATION: primer

<400> SEQUENCE: 89
catagaaggc attttgctgt tccttgtttt tcggagcttg tgcatcgttc agc        53

<210> SEQ ID NO 90
<211> LENGTH: 366
<212> TYPE: DNA
<213> ORGANISM: Staphylococcus aureus

<400> SEQUENCE: 90

```
gcggacaaca agtttaacaa agaacaacag aacgcctttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc gaaagacaac   180
aagaacaagg aacagcaaaa tgccttctat gaaattctgc atctgccgaa cctgaccgaa   240
gaacagcgta atggcttcat tcaaagcctg aaggacgacc cgagtgtttc caagaaaatt   300
ctggccgaag ccaaaaagct gaatgatgca caggctccga actcgagca ccaccaccac   360
caccac                                                              366
```

<210> SEQ ID NO 91
<211> LENGTH: 363
<212> TYPE: DNA
<213> ORGANISM: Staphylococcus aureus

<400> SEQUENCE: 91

```
gcggacaaca agtttaacaa agaacaacag aacgcctttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc ggacaacaag   180
aacaaggaac agcaaaatgc cttctatgaa attctgcatc tgccgaacct gaccgaagaa   240
cagcgtaatg gcttcattca aagcctgaag gacgacccga gtgtttccaa gaaaattctg   300
gccgaagcca aaaagctgaa tgatgcacag gctccgaaac tcgagcacca ccaccaccac   360
cac                                                                 363
```

<210> SEQ ID NO 92
<211> LENGTH: 360
<212> TYPE: DNA
<213> ORGANISM: Staphylococcus aureus

<400> SEQUENCE: 92

```
gcggacaaca agtttaacaa agaacaacag aacgcctttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc ggacaacaac   180
aaggaacagc aaaatgcctt ctatgaaatt ctgcatctgc cgaacctgac cgaagaacag   240
cgtaatggct tcattcaaag cctgaaggac gacccgagtg tttccaaaga aattctggcc   300
gaagccaaaa agctgaatga tgcacaggct ccgaaactcg agcaccacca ccaccaccac   360
```

<210> SEQ ID NO 93
<211> LENGTH: 360
<212> TYPE: DNA
<213> ORGANISM: Staphylococcus aureus

<400> SEQUENCE: 93

```
gcggacaaca agtttaacaa agaacaacag aacgcctttt acgaaatcct gcacctgccg    60
aacctgacgg aagaacaacg caacggtttt attcagagcc tgaaagatga cccgagcgtg   120
tctaaggaaa tcctggcgga agccaaaaag ctgaacgatg cacaagctcc ggaccaccac   180
aaggaacagc aaaatgcctt ctatgaaatt ctgcatctgc cgaacctgac cgaagaacag   240
cgtaatggct tcattcaaag cctgaaggac gacccgagtg tttccaaaga aattctggcc   300
gaagccaaaa agctgaatga tgcacaggct ccgaaactcg agcaccacca ccaccaccac   360
```

<210> SEQ ID NO 94
<211> LENGTH: 366
<212> TYPE: DNA
<213> ORGANISM: Staphylococcus aureus

<400> SEQUENCE: 94

| | | |
|---|---|---|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gaatgacaac | 180 |
| gataacaagg aacagcaaaa tgccttctat gaaattctgc atctgccgaa cctgaccgaa | 240 |
| gaacagcgta atggcttcat tcaaagcctg aaggacgacc cgagtgtttc caaagaaatt | 300 |
| ctggccgaag ccaaaaagct gaatgatgca caggctccga aactcgagca ccaccaccac | 360 |
| caccac | 366 |

<210> SEQ ID NO 95
<211> LENGTH: 366
<212> TYPE: DNA
<213> ORGANISM: Staphylococcus aureus

<400> SEQUENCE: 95

| | | |
|---|---|---|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gggagacaac | 180 |
| gggaacaagg aacagcaaaa tgccttctat gaaattctgc atctgccgaa cctgaccgaa | 240 |
| gaacagcgta atggcttcat tcaaagcctg aaggacgacc cgagtgtttc caaagaaatt | 300 |
| ctggccgaag ccaaaaagct gaatgatgca caggctccga aactcgagca ccaccaccac | 360 |
| caccac | 366 |

<210> SEQ ID NO 96
<211> LENGTH: 366
<212> TYPE: DNA
<213> ORGANISM: Staphylococcus aureus

<400> SEQUENCE: 96

| | | |
|---|---|---|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gcatgaccac | 180 |
| caccacaagg aacagcaaaa tgccttctat gaaattctgc atctgccgaa cctgaccgaa | 240 |
| gaacagcgta atggcttcat tcaaagcctg aaggacgacc cgagtgtttc caaagaaatt | 300 |
| ctggccgaag ccaaaaagct gaatgatgca caggctccga aactcgagca ccaccaccac | 360 |
| caccac | 366 |

<210> SEQ ID NO 97
<211> LENGTH: 366
<212> TYPE: DNA
<213> ORGANISM: Staphylococcus aureus

<400> SEQUENCE: 97

| | | |
|---|---|---|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gcatgaccac | 180 | gatcacaagg aacagcaaaa tgccttctat gaaattctgc atctgccgaa cctgaccgaa    240 gaacagcgta atggcttcat tcaaagcctg aaggacgacc cgagtgtttc caaagaaatt    300 ctggccgaag ccaaaaagct gaatgatgca caggctccga aactcgagca ccaccaccac    360 caccac                                                                366

<210> SEQ ID NO 98
<211> LENGTH: 372
<212> TYPE: DNA
<213> ORGANISM: Staphylococcus aureus

<400> SEQUENCE: 98
gcggacaaca agtttaacaa agaacaacag aacgcctttt acgaaatcct gcacctgccg    60
aacctgacgg aagaacaacg caacggtttt attcagagcc tgaaagatga cccgagcgtg    120
tctaaggaaa tcctggcgga agccaaaaag ctgaacgatg cacaagctcc gaatgacaat    180
gataacgata acaaggaaca gcaaaatgcc ttctatgaaa ttctgcatct gccgaacctg    240
accgaagaac agcgtaatgg cttcattcaa agcctgaagg acgacccgag tgtttccaaa    300
gaaattctgg ccgaagccaa aaagctgaat gatgcacagg ctccgaaact cgagcaccac    360
caccaccacc ac                                                         372

<210> SEQ ID NO 99
<211> LENGTH: 372
<212> TYPE: DNA
<213> ORGANISM: Staphylococcus aureus

<400> SEQUENCE: 99
gcggacaaca agtttaacaa agaacaacag aacgcctttt acgaaatcct gcacctgccg    60
aacctgacgg aagaacaacg caacggtttt attcagagcc tgaaagatga cccgagcgtg    120
tctaaggaaa tcctggcgga agccaaaaag ctgaacgatg cacaagctcc gaacggagac    180 aacgggata acaaggaaca gcaaaatgcc ttctatgaaa ttctgcatct gccgaacctg    240
accgaagaac agcgtaatgg cttcattcaa agcctgaagg acgacccgag tgtttccaaa    300
gaaattctgg ccgaagccaa aaagctgaat gatgcacagg ctccgaaact cgagcaccac    360
caccaccacc ac                                                         372

<210> SEQ ID NO 100
<211> LENGTH: 372
<212> TYPE: DNA
<213> ORGANISM: Staphylococcus aureus

<400> SEQUENCE: 100
gcggacaaca agtttaacaa agaacaacag aacgcctttt acgaaatcct gcacctgccg    60
aacctgacgg aagaacaacg caacggtttt attcagagcc tgaaagatga cccgagcgtg    120
tctaaggaaa tcctggcgga agccaaaaag ctgaacgatg cacaagctcc gcatgaccat    180
gatcacgatc acaaggaaca gcaaaatgcc ttctatgaaa ttctgcatct gccgaacctg    240
accgaagaac agcgtaatgg cttcattcaa agcctgaagg acgacccgag tgtttccaaa    300
gaaattctgg ccgaagccaa aaagctgaat gatgcacagg ctccgaaact cgagcaccac    360
caccaccacc ac                                                         372

<210> SEQ ID NO 101
<211> LENGTH: 363
<212> TYPE: DNA

<213> ORGANISM: Staphylococcus aureus

<400> SEQUENCE: 101

| | |
|---|---:|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gaaaaagttc | 180 |
| aacaaggaac agcaaaatgc cttctatgaa attctgcatc tgccgaacct gaccgaagaa | 240 |
| cagcgtaatg gcttcattca aagcctgaag gacgacccga gtgtttccaa agaaattctg | 300 |
| gccgaagcca aaaagctgaa tgatgcacag gctccgaaac tcgagcacca ccaccaccac | 360 |
| cac | 363 |

<210> SEQ ID NO 102
<211> LENGTH: 360
<212> TYPE: DNA
<213> ORGANISM: Staphylococcus aureus

<400> SEQUENCE: 102

| | |
|---|---:|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gaaattcaac | 180 |
| aaggaacagc aaaatgcctt ctatgaaatt ctgcatctgc cgaacctgac cgaagaacag | 240 |
| cgtaatggct tcattcaaag cctgaaggac gacccgagtg tttccaaaga aattctggcc | 300 |
| gaagccaaaa agctgaatga tgcacaggct ccgaaactcg agcaccacca ccaccaccac | 360 |

<210> SEQ ID NO 103
<211> LENGTH: 357
<212> TYPE: DNA
<213> ORGANISM: Staphylococcus aureus

<400> SEQUENCE: 103

| | |
|---|---:|
| gcggacaaca agtttaacaa agaacaacag aacgcctttt acgaaatcct gcacctgccg | 60 |
| aacctgacgg aagaacaacg caacggtttt attcagagcc tgaaagatga cccgagcgtg | 120 |
| tctaaggaaa tcctggcgga agccaaaaag ctgaacgatg cacaagctcc gaaaaacaag | 180 |
| gaacagcaaa atgccttcta tgaaattctg catctgccga acctgaccga gaacagcgt | 240 |
| aatggcttca ttcaaagcct gaaggacgac ccgagtgttt ccaaagaaat tctggccgaa | 300 |
| gccaaaaagc tgaatgatgc acaggctccg aaactcgagc accaccacca ccaccac | 357 |

<210> SEQ ID NO 104
<211> LENGTH: 124
<212> TYPE: PRT
<213> ORGANISM: Staphylococcus aureus

<400> SEQUENCE: 104

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu 65                70                75                80

Thr Glu Glu Gln Arg Asn Gly Phe Ile Gln Ser Leu Lys Asp Asp Pro
                    85                  90                  95

Ser Val Ser Lys Glu Ile Leu Ala Glu Ala Lys Lys Leu Asn Asp Ala
            100                 105                 110

Gln Ala Pro Lys Leu Glu His His His His His His
        115                 120

<210> SEQ ID NO 105
<211> LENGTH: 122
<212> TYPE: PRT
<213> ORGANISM: Staphylococcus aureus

<400> SEQUENCE: 105

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Asp Asn Lys Asn Lys Glu
    50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 106
<211> LENGTH: 121
<212> TYPE: PRT
<213> ORGANISM: Staphylococcus aureus

<400> SEQUENCE: 106

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp Asn Lys Asn Lys Glu Gln
    50                  55                  60

Gln Asn Ala Phe Tyr Glu Ile Leu His Leu Pro Asn Leu Thr Glu Glu
65                  70                  75                  80

Gln Arg Asn Gly Phe Ile Gln Ser Leu Lys Asp Asp Pro Ser Val Ser
                85                  90                  95

Lys Glu Ile Leu Ala Glu Ala Lys Lys Leu Asn Asp Ala Gln Ala Pro
            100                 105                 110

Lys Leu Glu His His His His His His
        115                 120

<210> SEQ ID NO 107
<211> LENGTH: 120
<212> TYPE: PRT

-continued

<213> ORGANISM: Staphylococcus aureus

<400> SEQUENCE: 107

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp Asn Asn Lys Glu Gln Gln
50                  55                  60

Asn Ala Phe Tyr Glu Ile Leu His Leu Pro Asn Leu Thr Glu Glu Gln
65                  70                  75                  80

Arg Asn Gly Phe Ile Gln Ser Leu Lys Asp Asp Pro Ser Val Ser Lys
                85                  90                  95

Glu Ile Leu Ala Glu Ala Lys Lys Leu Asn Asp Ala Gln Ala Pro Lys
            100                 105                 110

Leu Glu His His His His His His
            115                 120

<210> SEQ ID NO 108
<211> LENGTH: 120
<212> TYPE: PRT
<213> ORGANISM: Staphylococcus aureus

<400> SEQUENCE: 108

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asp His Lys Glu Gln Gln
50                  55                  60

Asn Ala Phe Tyr Glu Ile Leu His Leu Pro Asn Leu Thr Glu Glu Gln
65                  70                  75                  80

Arg Asn Gly Phe Ile Gln Ser Leu Lys Asp Asp Pro Ser Val Ser Lys
                85                  90                  95

Glu Ile Leu Ala Glu Ala Lys Lys Leu Asn Asp Ala Gln Ala Pro Lys
            100                 105                 110

Leu Glu His His His His His His
            115                 120

<210> SEQ ID NO 109
<211> LENGTH: 122
<212> TYPE: PRT
<213> ORGANISM: Staphylococcus aureus

<400> SEQUENCE: 109

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asn Asp Asn Asp Asn Lys Glu
50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 110
<211> LENGTH: 122
<212> TYPE: PRT
<213> ORGANISM: Staphylococcus aureus

<400> SEQUENCE: 110

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Gly Asp Asn Gly Asn Lys Glu
    50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 111
<211> LENGTH: 122
<212> TYPE: PRT
<213> ORGANISM: Staphylococcus aureus

<400> SEQUENCE: 111

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro His Asp His His Lys Glu
    50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His His
        115                 120

<210> SEQ ID NO 112

```
<211> LENGTH: 122
<212> TYPE: PRT
<213> ORGANISM: Staphylococcus aureus

<400> SEQUENCE: 112

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro His Asp His Asp His Lys Glu
50                  55                  60

Gln Gln Asn Ala Phe Tyr Glu Ile Leu His Leu Pro Asn Leu Thr Glu
65                  70                  75                  80

Glu Gln Arg Asn Gly Phe Ile Gln Ser Leu Lys Asp Asp Pro Ser Val
                85                  90                  95

Ser Lys Glu Ile Leu Ala Glu Ala Lys Lys Leu Asn Asp Ala Gln Ala
            100                 105                 110

Pro Lys Leu Glu His His His His His
        115                 120

<210> SEQ ID NO 113
<211> LENGTH: 124
<212> TYPE: PRT
<213> ORGANISM: Staphylococcus aureus

<400> SEQUENCE: 113

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Asn Asp Asn Asp Asn Asp Asn
50                  55                  60

Lys Glu Gln Gln Asn Ala Phe Tyr Glu Ile Leu His Leu Pro Asn Leu
65                  70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Leu Glu His His His His His
        115                 120

<210> SEQ ID NO 114
<211> LENGTH: 124
<212> TYPE: PRT
<213> ORGANISM: Staphylococcus aureus

<400> SEQUENCE: 114

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45
```

```
Lys Lys Leu Asn Asp Ala Gln Ala Pro Asn Gly Asp Asn Gly Asp Asn
 50                  55                  60
Lys Glu Gln Gln Asn Ala Phe Tyr Glu Ile Leu His Leu Pro Asn Leu
 65                  70                  75                  80
Thr Glu Glu Gln Arg Asn Gly Phe Ile Gln Ser Leu Lys Asp Asp Pro
                 85                  90                  95
Ser Val Ser Lys Glu Ile Leu Ala Glu Ala Lys Lys Leu Asn Asp Ala
            100                 105                 110
Gln Ala Pro Lys Leu Glu His His His His His His
            115                 120
```

<210> SEQ ID NO 115
<211> LENGTH: 124
<212> TYPE: PRT
<213> ORGANISM: Staphylococcus aureus

<400> SEQUENCE: 115

```
Ala Asp Asn Lys Phe Asn Lys Glu Gln Gln Asn Ala Phe Tyr Glu Ile
 1               5                  10                  15
Leu His Leu Pro Asn Leu Thr Glu Glu Gln Arg Asn Gly Phe Ile Gln
                20                  25                  30
Ser Leu Lys Asp Asp Pro Ser Val Ser Lys Glu Ile Leu Ala Glu Ala
             35                  40                  45
Lys Lys Leu Asn Asp Ala Gln Ala Pro His Asp His Asp His Asp His
 50                  55                  60
Lys Glu Gln Gln Asn Ala Phe Tyr Glu Ile Leu His Leu Pro Asn Leu
 65                  70                  75                  80
Thr Glu Glu Gln Arg Asn Gly Phe Ile Gln Ser Leu Lys Asp Asp Pro
                 85                  90                  95
Ser Val Ser Lys Glu Ile Leu Ala Glu Ala Lys Lys Leu Asn Asp Ala
            100                 105                 110
Gln Ala Pro Lys Leu Glu His His His His His
            115                 120
```

<210> SEQ ID NO 116
<211> LENGTH: 121
<212> TYPE: PRT
<213> ORGANISM: Staphylococcus aureus

<400> SEQUENCE: 116

```
Ala Asp Asn Lys Phe Asn Lys Glu Gln Gln Asn Ala Phe Tyr Glu Ile
 1               5                  10                  15
Leu His Leu Pro Asn Leu Thr Glu Glu Gln Arg Asn Gly Phe Ile Gln
                20                  25                  30
Ser Leu Lys Asp Asp Pro Ser Val Ser Lys Glu Ile Leu Ala Glu Ala
             35                  40                  45
Lys Lys Leu Asn Asp Ala Gln Ala Pro Lys Lys Phe Asn Lys Glu Gln
 50                  55                  60
Gln Asn Ala Phe Tyr Glu Ile Leu His Leu Pro Asn Leu Thr Glu Glu
 65                  70                  75                  80
Gln Arg Asn Gly Phe Ile Gln Ser Leu Lys Asp Asp Pro Ser Val Ser
                 85                  90                  95
Lys Glu Ile Leu Ala Glu Ala Lys Lys Leu Asn Asp Ala Gln Ala Pro
            100                 105                 110
Lys Leu Glu His His His His His
            115                 120
```

```
<210> SEQ ID NO 117
<211> LENGTH: 120
<212> TYPE: PRT
<213> ORGANISM: Staphylococcus aureus

<400> SEQUENCE: 117

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Phe Asn Lys Glu Gln Gln
    50                  55                  60

Asn Ala Phe Tyr Glu Ile Leu His Leu Pro Asn Leu Thr Glu Glu Gln
65                  70                  75                  80

Arg Asn Gly Phe Ile Gln Ser Leu Lys Asp Asp Pro Ser Val Ser Lys
                85                  90                  95

Glu Ile Leu Ala Glu Ala Lys Lys Leu Asn Asp Ala Gln Ala Pro Lys
            100                 105                 110

Leu Glu His His His His His His
        115                 120

<210> SEQ ID NO 118
<211> LENGTH: 119
<212> TYPE: PRT
<213> ORGANISM: Staphylococcus aureus

<400> SEQUENCE: 118

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Asn Lys Glu Gln Gln Asn
    50                  55                  60

Ala Phe Tyr Glu Ile Leu His Leu Pro Asn Leu Thr Glu Glu Gln Arg
65                  70                  75                  80

Asn Gly Phe Ile Gln Ser Leu Lys Asp Asp Pro Ser Val Ser Lys Glu
                85                  90                  95

Ile Leu Ala Glu Ala Lys Lys Leu Asn Asp Ala Gln Ala Pro Lys Leu
            100                 105                 110

Glu His His His His His His
        115
```